US007855193B2

(12) United States Patent
Saha et al.

(10) Patent No.: US 7,855,193 B2
(45) Date of Patent: Dec. 21, 2010

(54) S1P RECEPTOR MODULATING COMPOUNDS AND USE THEREOF

(75) Inventors: Ashis K. Saha, Stow, MA (US); Nili Schutz, Tel-Aviv (IL); Xiang Yu, Acton, MA (US); Dilara McCauley, Cambridge, MA (US); Mercedes Lobera, Concord, MA (US); Yael Marantz, Kadima (IL); Jian Lin, Walpole, MA (US); Srinivasa R. Cheruku, Lexington, MA (US); Pini Orbach, Needham, MA (US); Anurag Sharadendu, Bedford, MA (US); Robert Christian Penland, Watertown, MA (US); Kimberley Gannon, Watertown, MA (US); Sharon Shacham, Newton, MA (US); Silvia Noiman, Herzliyya (IL); Oren Becker, Mevaseret Zion (IL)

(73) Assignee: EPIX Pharmaceuticals, Inc., Lexington, MA (US)

( * ) Notice: Subject to any disclaimer, the term of this patent is extended or adjusted under 35 U.S.C. 154(b) by 325 days.

(21) Appl. No.: 11/491,766

(22) Filed: Jul. 24, 2006

(65) Prior Publication Data

US 2008/0064677 A9    Mar. 13, 2008

Related U.S. Application Data

(60) Provisional application No. 60/784,549, filed on Mar. 21, 2006, provisional application No. 60/753,806, filed on Dec. 22, 2005, provisional application No. 60/739,466, filed on Nov. 23, 2005.

(51) Int. Cl.
    A61K 31/397    (2006.01)
    A61K 31/5377   (2006.01)
    A61K 31/4525   (2006.01)
    A61K 31/4025   (2006.01)
    A61K 31/343    (2006.01)
    C07D 411/06    (2006.01)
    C07D 405/06    (2006.01)
    C07D 205/04    (2006.01)
    C07D 307/80    (2006.01)

(52) U.S. Cl. .............................. 514/210.19; 514/233.5; 514/320; 514/422; 514/469; 544/153; 546/196; 548/517; 548/953; 549/467

(58) Field of Classification Search ............ 514/210.19, 514/233.5, 320, 422, 469; 544/153; 546/196; 548/517, 953; 549/467
See application file for complete search history.

(56) References Cited

U.S. PATENT DOCUMENTS

| 3,329,781 A | 7/1967 | Wiser |
| 4,767,896 A | 8/1988 | Nigg et al. |
| 5,145,865 A | 9/1992 | Fujii et al. |
| 5,614,531 A | 3/1997 | Juraszyk et al. |
| 5,880,284 A | 3/1999 | Himmelsbach et al. |
| 6,384,061 B1 | 5/2002 | Lee et al. |
| 6,411,326 B1 | 6/2002 | Tabata |
| 2002/0156074 A1* | 10/2002 | Barvian et al. ........... 514/227.8 |
| 2002/0183519 A1 | 12/2002 | Nar et al. |
| 2005/0014725 A1 | 1/2005 | Mi et al. |
| 2005/0113283 A1 | 5/2005 | Solow-Cordero et al. |
| 2006/0135786 A1 | 6/2006 | Saha et al. |
| 2007/0173487 A1 | 7/2007 | Saha et al. |
| 2008/0015177 A1 | 1/2008 | Saha et al. |
| 2008/0027036 A1* | 1/2008 | Burli et al. ............. 514/210.18 |
| 2008/0064677 A9 | 3/2008 | Saha et al. |

FOREIGN PATENT DOCUMENTS

| EP | 1 553 075 A1 | 7/2005 |
| JP | 10-204059 | 8/1998 |
| JP | 10-204059 A | 8/1998 |
| WO | 02064616 A2 | 8/2002 |
| WO | 03061567 A2 | 7/2003 |
| WO | 03062252 A1 | 7/2003 |
| WO | 03105771 A2 | 12/2003 |
| WO | 2004048383 A1 | 6/2004 |
| WO | 2004062663 A1 | 7/2004 |
| WO | 2004113330 A1 | 12/2004 |
| WO | 2005020882 A3 | 3/2005 |
| WO | 2006064757 A1 | 6/2006 |
| WO | 2007061458 A2 | 5/2007 |
| WO | 2007109334 A2 | 9/2007 |
| WO | WO 2007/109330 A3 | 9/2007 |
| WO | WO 2009/038759 A2 | 3/2009 |

OTHER PUBLICATIONS

Traynor et al., 1995, "Modulation by μ-opioid agonists of guanosine-5'-O-(3-[35S]thio)triphosphate binding to membranes from human neuroblastoma SH-SY5Y cells," Molecular Pharmacology, 47, 848-854.

Zemann et al., 2006, "Sphingosine kinase type 2 is essential for lymphopenia induced by the immunomodulatory drug FTY720," Blood, 107(4), 1454-1458.

Pan et al., 2006, "A monoselective sphingosine-1-phospate receptor-1 agonist preents allograft rejection in a stringent rat heart transplantation model," Chemistry & Biology, 13, 1227-1234.

Abdel-Rahman, T.M., 1998, "Synthesis and Antimicrobial Activity of Some new Thiophene-2-Sulphonyl, Amino Acids and Their Peptide Derivatives," Mans.Sci.Bull. (A Chem.) vol. 25 (1), Jun. 1998.

\* cited by examiner

*Primary Examiner*—Joseph R Kosack
(74) *Attorney, Agent, or Firm*—McDonnell Boehnen Hulbert & Berghoff

(57) ABSTRACT

The present invention relates to compounds of the general formula (I) that have activity as S1P receptor modulating agents and the use of such compounds to treat diseases associated with inappropriate S1P receptor activity. The compounds may be used as immunomodulators, e.g., for treating or preventing diseases such as autoimmune and related immune disorders including systemic lupus erythematosus, inflammatory bowel diseases such as Crohn's disease and ulcerative colitis, type I diabetes, uveitis, psoriasis, myasthenia gravis, rheumatoid arthritis, non-glomerular nephrosis, hepatitis, Behçet's disease, glomerulonephritis, chronic thrombocytopenic purpura, hemolytic anemia, hepatitis and Wegner's granuloma; and for treating other conditions.

11 Claims, No Drawings

S1P RECEPTOR MODULATING COMPOUNDS AND USE THEREOF

RELATED APPLICATIONS

This application claims the benefit of priority under 35 U.S.C. 119(e) to U.S. Provisional Application No. 60/784,549, filed on Mar. 21, 2006, the entire contents of which is incorporated herein by reference. This application also claims the benefit of priority under 35 U.S.C. 119(e) to U.S. Provisional Application No. 60/753,806, filed Dec. 22, 2005, and U.S. Provisional Application No. 60/739,466 filed Nov. 23, 2005.

FIELD OF THE INVENTION

The present invention relates to compounds that have activity as S1P receptor modulating agents and the use of such compounds to treat diseases associated with inappropriate S1P receptor activity.

BACKGROUND OF THE INVENTION

Sphingosine-1-phosphate (S1P) has been demonstrated to induce many cellular effects, is including those that result in platelet aggregation, cell proliferation, cell morphology, tumor cell invasion, endothelial cell chemotaxis and endothelial cell in vitro angiogenesis. S1P receptors are therefore good targets for therapeutic applications such as wound healing and tumor growth inhibition. S1P signals cells in part via a set of G protein-coupled receptors named S1P1, S1P2, S1P3, S1P4, and S1P5 (formerly called EDG-1, EDG-5, EDG-3, EDG-6, and EDG-8, respectively). These receptors share 50-55% amino acid and cluster identity with three other receptors (LPA1, LPA2, and LPA3 (formerly EDG-2, EDG-4 and EDG-7)) for the structurally-related lysophosphatidic acid (LPA).

A conformational shift is induced in the G-Protein Coupled Receptor (GPCR) when the ligand binds to that receptor, causing GDP to be replaced by GTP on the α-subunit of the associated G-proteins and subsequent release of the G-proteins into the cytoplasm. The α-subunit then dissociates from the βγ-subunit, and each subunit can then associate with effector proteins, which activate second messengers leading to a cellular response. Eventually the GTP on the G-proteins is hydrolyzed to GDP, and the subunits of the G-proteins re-associate with each other and then with the receptor. Amplification plays a major role in the general GPCR pathway. The binding of one ligand to one receptor leads to the activation of many G-proteins, each capable of associating with many effector proteins, leading to an amplified cellular response.

S1P receptors make good drug targets, because individual receptors are both tissue- and response-specific. Tissue specificity of the S1P receptors is important, because development of an agonist or antagonist selective for one receptor localizes the cellular response to tissues containing that receptor, limiting unwanted side effects. Response specificity of the S1P receptors is also important because it allows for development of agonists or antagonists that initiate or suppress certain cellular responses without affecting other things. For example, the response specificity of the S1P receptors could allow for an S1P mimetic that initiates platelet aggregation without affecting cell morphology.

S1P is formed as a metabolite of sphingosine in its reaction with sphingosine kinase, and is abundantly stored in platelet aggregates where high levels of sphingosine kinase exist and sphingosine lyase is lacking. S1P is released during platelet aggregation, accumulates in serum and is also found in malignant ascites. S1P biodegradation most likely proceeds via hydrolysis by ectophosphohydrolases, specifically the sphingosine 1-phosphate phosphohydrolases.

SUMMARY OF THE INVENTION

The present invention relates to the use of new compositions which include S1P modulators, e.g., agonists, partial agonists, inverse agonists and antagonists, for treating, preventing or curing various S1P receptor-related conditions. The invention features compounds which are S1P receptor modulators; in an embodiment, such compounds include those having the formula

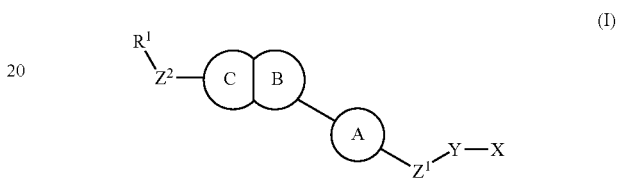

and pharmaceutically acceptable salts thereof.

In formula I, A may be an aryl or heteroaryl group, optionally substituted with one, two or three substituents which may include halogen, hydroxyl, $SR^2$, $S(O)_2R^2$, $S(O)_2NR^2$, $NHS(O)_2R^2$, $COR^2$, $CO_2R^2$, cyano, amino, $C_{1-5}$ alkylamino/arylamino/heteroarylamino, alkyl, $C_{1-5}$ alkylthio, $C_{1-5}$ alkoxy, halogen-substituted $C_{1-6}$ alkyl, and halogen-substituted $C_{1-5}$ alkoxy. Optionally two adjacent substituents of A may, taken with $Z^1$ and the ring A to which they are attached, form a fused ring that may optionally contain one or more hetero atoms. $R^2$ may be selected independently from hydrogen, hydroxyl, amino, alkylamino/arylamino, $C_{1-6}$ alkyl, $C_{1-5}$ alkoxy, $C_{1-5}$ alkylthio, halogen-substituted $C_{1-6}$ alkyl and halogen-substituted $C_{1-5}$ alkoxy; or aryl/heteroaryl. A may desirably be a $C_{5-6}$ cyclic ring (alicyclic or aromatic) optionally having one or more heteroatoms.

B and C are an at least partially aromatic bicyclic ring system, e.g., bicycloaryl, bicycloheteroaryl, dihydrobicyclic or tetrahydrobicyclic aryl and heteroaryl. The bicyclic ring system may be substituted with 1 to 5 substituents, e.g., $C_{1-6}$ alkyl, $C_{1-5}$ alkylthio, $C_{1-5}$ alkoxy, halogen, hydroxyl, cyano, halogen-substituted $C_{1-6}$alkyl and halogen-substituted $C_{1-5}$ alkoxy.

$Z^1$ and $Z^2$ may be independently selected from O, $NR^3$, S, S(O), $S(O)_2$, $S(O)_2NR^3$, $(CR^4R^5)_n$, C=O, C=S, C=N—$R^3$, or a direct bond. $R^3$ may be hydrogen, hydroxyl, $C_{1-6}$ alkyl, $C_{1-5}$ alkoxy, $C_{1-5}$ alkylthio, halogen-substituted $C_{1-6}$ alkyl and halogen-substituted $C_{1-5}$ alkoxy; aryl or heteroaryl. $R^4$ and $R^5$ may independently be hydrogen, halogen, hydroxyl, cyano, $C_{1-6}$ alkyl, $C_{1-5}$ alkoxy, $C_{1-5}$ alkylthio, halogen-substituted $C_{1-6}$ alkyl and halogen-substituted $C_{1-5}$ alkoxy; aryl or heteroaryl or together form "C=O"; n may be 0, 1, 2 or 3. In an embodiment where $Z^2$ is a direct bond, $R_3$ may be a $C_3$-$C_6$ ring optionally containing a heteroatom.

$R^1$ may be $C_{1-6}$ alkyl, $C_{2-6}$ alkenyl, $C_{2-6}$ alkynyl, $C_{3-6}$ cycloalkyl, $C_{1-5}$ alkoxy, $C_{1-5}$ alkylamino, aryl or heteroaryl. $R^1$ may optionally be substituted with, e.g., hydroxyl, halogen, cyano, amino, alkylamino, aryl amino, heteroarylamino groups, and the aryl and heteroaryl groups may optionally be substituted with 1-5 substituents, e.g., hydroxyl, halogen, cyano, $C_{1-6}$ alkyl, $C_{1-5}$ alkylthio, $C_{1-5}$ alkoxy, $C_{3-6}$ cycloalkyl.

X may be $WC(O)OR^{6a}$, $WP(O)R^{6b} R^{6c}$, $WS(O)_2OH$, $WCONHSO_3H$ or 1H-tetrazol-5-yl. W may be a direct bond, oxygen or $C_{1-4}$ alkyl with substituents independently selected from the group consisting of: halogen, hydroxyl, cyano, amino, alkylamino, arylamino, heteroarylamino groups, $C_{1-4}$ alkoxy and; $R^{6a}$ may be hydrogen or $C_{1-4}$alkyl; $R^{6b}$ and $R^{6c}$ may be hydrogen, hydroxyl, $C_{1-4}$alkyl or halogen substituted $C_{1-4}$alkyl.

Y may be a residue of formula (a) where the left and right asterisks indicate the point of attachment:

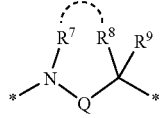
(a)

wherein Q may be a direct bond, C=O, C=S, $SO_2$, C=ONR or $(CR^{10}R^{11})_m$; m may be 0, 1, 2 or 3; $R^7$ and $R^8$ may be independently hydrogen, halogen, amino, $C_{1-5}$ alkylamino, hydroxyl, cyano, $C_{1-6}$ alkyl, $C_{1-6}$ hydroxyalkyl (e.g., hydroxy-terminated alkyl), $C_{1-5}$ alkylthio, $C_{1-5}$ alkoxy, halogen-substituted $C_{1-6}$ alkyl and halogen-substituted $C_{1-5}$ alkoxy; or $R^7$ and $R^8$ may be joined together with the atoms to which they are attached to form a 4 to 7-membered ring, optionally having a hetero atom. $R^9$ may be hydrogen, halogen, hydroxyl, cyano, $C_{1-6}$ alkyl, $C_{1-5}$ alkylthio, $C_{1-5}$ alkoxy, halogen-substituted $C_{1-6}$ alkyl or halogen-substituted $C_{1-5}$ alkoxy; $R^{10}$ and $R^{11}$ may individually be hydrogen, halogen, hydroxyl, cyano, $C_{1-6}$ alkyl, $C_{1-5}$ alkoxy, $C_{1-5}$ alkylthio, halogen-substituted $C_{1-6}$ alkyl or halogen-substituted $C_{1-5}$ alkoxy.

In another embodiment, the invention includes compounds of formula (II):

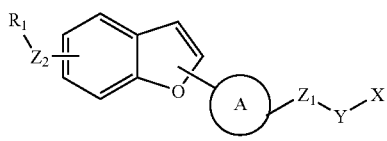
(II)

wherein A may be an aryl or heteroaryl group; X is —C(O)OR$^{6a}$, where $R^{6a}$ is hydrogen or $C_{1-4}$alkyl; Y is a residue of formula (a)

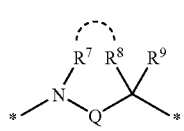
(a)

wherein Q is $(CR^{10}R^{11})_m$; m is 0, 1, 2, 3 or 4; $R^7$ and $R^8$ may independently be hydrogen, hydroxyl, lower alkyl; or $R^7$ and $R^8$, taken with the atoms to which they are attached, form a ring; $R^9$ is selected from, e.g., hydrogen, halogen, hydroxyl, or cyano; and $Z^1$ and $Z^2$ are independently O or $(CR^4R^5)_n$, where $R^4$ and $R^5$ are independently hydrogen, halogen, hydroxyl, cyano, $C_{1-6}$ alkyl, $C_{1-5}$ alkoxy; n is 0, 1, 2 or 3; and $R^1$ is selected from, e.g., $C_{1-6}$ alkyl, $C_{2-6}$ alkenyl, $C_{2-6}$ alkynyl, $C_{3-6}$ cycloalkyl, $C_{1-5}$ alkoxy, $C_{1-5}$ alkylamino, aryl or heteroaryl; or a pharmaceutically acceptable salts thereof The aryl or heteroaryl group may be substituted with one, two or three substituents such as halogen, hydroxyl, S, $S(O)_2$ $R^2$, $S(O)_2NR^2$, $NHS(O)_2R^2$, $COR^2$, $CO_2R^2$, cyano, amino, $C_{1-5}$ alkylamino/arylamino/heteroarylamino, $C_{1-6}$ alkyl, $C_{1-5}$ alkylthio, $C_{1-5}$ alkoxy, halogen-substituted $C_{1-6}$ alkyl, or halogen-substituted $C_{1-5}$ alkoxy (where $R^2$ is, e.g., of hydrogen, hydroxyl, amino, alkylamino/arylamino, $C_{1-6}$ alkyl, $C_{1-5}$ alkoxy, $C_{1-5}$ alkylthio, halogen-substituted $C_{1-6}$ alkyl and halogen-substituted $C_{1-5}$ alkoxy; or aryl/heteroaryl; or optionally, two adjacent substituents on A may, taken with $Z^1$ and the ring to which they are attached, form an is alicyclic or heterocyclic ring. $R^2$ may be selected from hydrogen, hydroxyl, amino, alkylamino/arylamino, $C_{1-6}$ alkyl, $C_{1-5}$ alkoxy, $C_{1-5}$ alkylthio, halogen-substituted $C_{1-6}$ alkyl and halogen-substituted $C_{1-5}$ alkoxy; or aryl/heteroaryl.

The benzofuranyl ring may be substituted with 1 to 5 substituents, e.g., of $C_{1-6}$ alkyl, $C_{1-5}$ alkylthio, $C_{1-5}$ alkoxy, halogen, hydroxyl, cyano, halogen-substituted $C_{1-6}$alkyl or halogen-substituted $C_{1-5}$ alkoxy. $R^1$ may be $C_{1-6}$ alkyl, $C_{2-6}$ alkenyl, $C_{2-6}$ alkynyl, $C_{3-6}$ cycloalkyl, $C_{1-5}$ alkoxy, $C_{1-5}$ alkylamino, aryl or heteroaryl; $R_1$ may optionally substituted with, e.g., hydroxyl, halogen, cyano, amino, alkylamino, arylamino, or heteroarylamino groups. (The aryl and heteroaryl groups may be substituted with one to five substituents such as hydroxyl, halogen, cyano, $C_{1-6}$ alkyl, $C_{1-5}$ alkylthio, $C_{1-5}$ alkoxy, and $C_{3-6}$ cycloalkyl.

The present invention relates, in one embodiment, to compounds according to Formula I. Preferably A is a substituted or unsubstituted aryl or heteroaryl group, which may be one illustrated below, where $R^{12}$ is hydrogen or $C_{1-6}$alkyl; and the left and right asterisks indicate the point of attachment in formula (I);

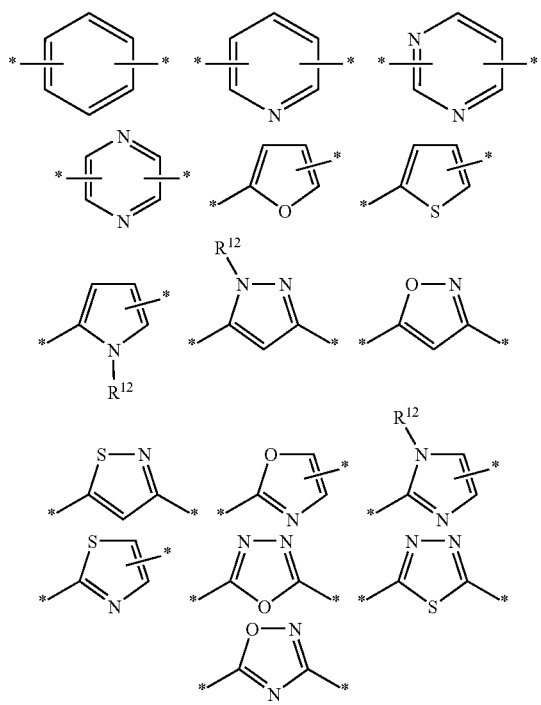

$R^{12}$ may be hydrogen, hydroxyl, amino, alkylamino or arylamino, $C_{1-6}$ alkyl, $C_{1-5}$ alkoxy, $C_{1-5}$ alkylthio, halogen-substituted $C_{1-6}$ alkyl and halogen-substituted $C_{1-5}$ alkoxy; aryl or heteroaryl; more preferably hydrogen.

B and C preferably are substituted or unsubstituted aryl or heteroaryl, e.g.,

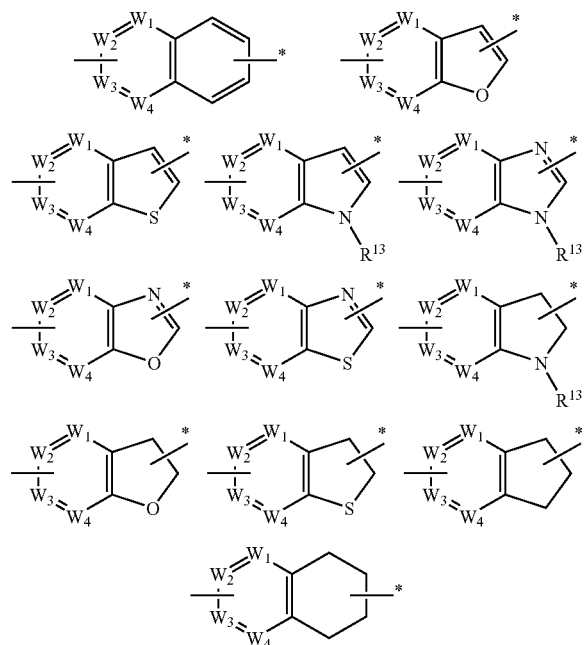

In the groups shown in the two tables directly above, the asterisks indicate that the group depicted may be attached to the molecule as shown, or "inverted". The groups depicted immediately above this text may desirably be present in the molecule in the orientation illustrated.

wherein $R^{12}$ is hydrogen or $C_{1-6}$ alkyl; and the left and right asterisks indicate the point of attachment in formula (I); $W_1$, $W_2$, $W_3$ or $W_4$ may be C, N, C—OH, C—OR$^{13}$ or C—R$^{13}$; $R^{13}$ is hydrogen or $C_{1-6}$alkyl, $C_{1-5}$alkylthio, $C_{1-5}$alkoxy, halogen, hydroxyl, cyano, halogen-substituted $C_{1-6}$alkyl and halogen-substituted $C_{1-5}$alkoxy.

$Z^1$ and $Z^2$ are preferably $CH_2$, O, S or a direct bond. $R^3$ is preferably methyl. $R^4$ and $R^5$ are preferably hydrogen or methyl. n is preferably 1 or 2. X may be combined with Y, e.g.,

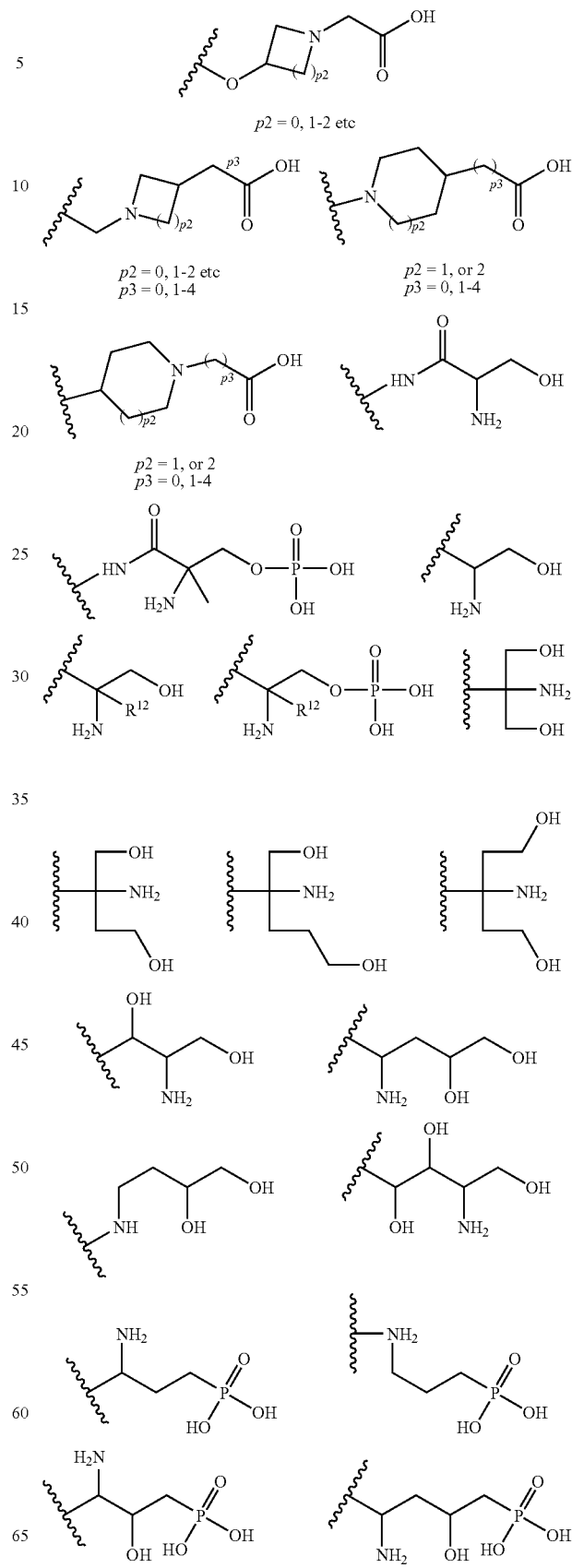

-continued

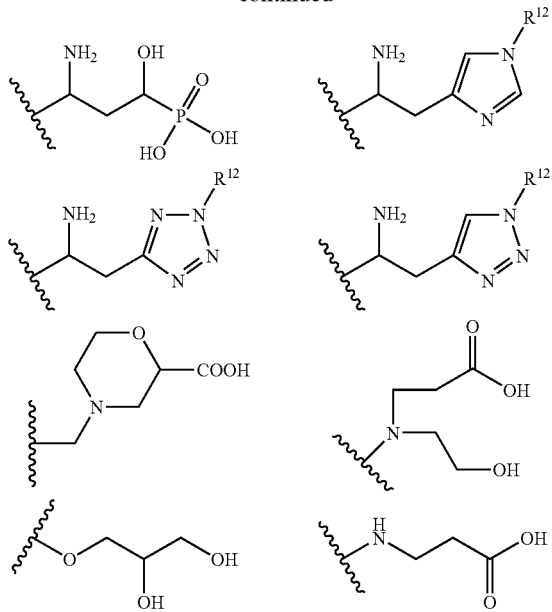

Optionally, two adjacent substituents on the ring A with $Z^1$ to form a fused ring, that may contain one or more hetero atoms, and wherein X may be combined with Y, e.g.,

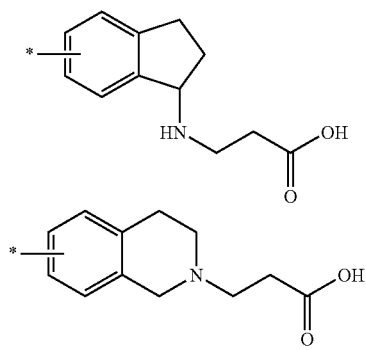

In one aspect, the present invention provides methods for modulating S1P-1 receptor mediated biological activity. The present invention also provides methods for using S1P-1 modulators (i.e., agonists or antagonists) in treating or preventing diseases such as ovarian cancer, peritoneal cancer, endometrial cancer, cervical cancer, breast cancer, colorectal cancer, uterine cancer, stomach cancer, small intestine cancer, thyroid cancer, lung cancer, kidney cancer, pancreas cancer and prostrate cancer; acute lung diseases, adult respiratory distress syndrome ("ARDS"), acute inflammatory exacerbation of chronic lung diseases such as asthma, surface epithelial cell injury such as transcorneal freezing or cutaneous burns, and cardiovascular diseases such as ischemia in a subject in need of such treatment or prevention.

In another aspect, the invention provides methods for using S1P-1 modulators in treating or preventing disorders such as, but not limited to, vasoconstriction in cerebral arteries, autoimmune and related immune disorders including systemic lupus erythematosus, inflammatory bowel diseases such as Crohn's disease and ulcerative colitis, type I diabetes, uveitis, psoriasis, myasthenia gravis, rheumatoid arthritis, non-glomerular nephrosis, hepatitis, Behcet's disease, glomerulonephritis, chronic thrombocytopenic purpura, hemolytic anemia, hepatitis and Wegner's granuloma.

In still another aspect, the invention provides methods for using S1P-1 modulators to treat or prevent a disease or disorder in a subject, comprising administering to a subject in need of such treatment or prevention a therapeutically effective amount of an S1P-1 modulator, e.g., an agonist, that stimulates the immune system. In certain embodiments, the subject is afflicted by an infectious agent. In other embodiments, the subject is immunocompromised.

In still another aspect, the present invention provides a method of modulating an S1P-1 receptor-mediated biological activity in a cell. A cell expressing the S1P-1 receptor is contacted with an amount of an S1P-1 receptor modulator sufficient to modulate the S1P-1 receptor mediated biological activity.

In yet another aspect, the present invention provides a method for modulating an S1P-1 receptor mediated biological activity in a subject. In such a method, an amount of a modulator of the S1P-1 receptor effective to modulate an S1P-1 receptor-mediated biological activity is administered to the subject.

In yet another aspect, the present invention provides a method for treating, preventing or ameliorating an S1P-1 receptor mediated condition in a subject. In such a method, an amount of a modulator of the S1P-1 receptor effective to modulate an S1P-1 receptor-mediated biological activity is administered to the subject. The S1P-1 receptor mediated condition may be, e.g., transplant rejection (solid organ transplant and islet cells); transplant rejection (tissue); cancer; autoimmune/inflammatory diseases; rheumatoid arthritis; lupus; insulin dependent diabetes (Type I); non-insulin dependent diabetes (Type II); multiple sclerosis; psoriasis; ulcerative colitis; inflammatory bowel disease; Crohn's disease; acute and chronic lymphocytic leukemias and lymphomas.

DETAILED DESCRIPTION OF THE INVENTION

The features and other details of the invention will now be more particularly described. It will be understood that particular embodiments described herein are shown by way of illustration and not as limitations of the invention. The principal features of this invention can be employed in various embodiments without departing from the scope of the invention. All parts and percentages are by weight unless otherwise specified.

DEFINITIONS

For convenience, certain terms used in the specification and examples are collected here.

"Treating", includes any effect, e.g., lessening, reducing, modulating, or eliminating, that results in the improvement of the condition, disease, disorder, etc.

"Alkyl" includes saturated aliphatic groups, e.g., straight-chain alkyl groups such as methyl, ethyl, propyl, butyl, pentyl, hexyl, heptyl, octyl, nonyl, and decyl; branched-chain alkyl groups (e.g., isopropyl, tert-butyl, and isobutyl); cycloalkyl (alicyclic) groups like cyclopropyl, cyclopentyl, cyclohexyl, cycloheptyl, and cyclooctyl); alkyl-substituted cycloalkyl groups; and cycloalkyl-substituted alkyl groups.

"Alkyl" groups may also optionally include heteroatoms, i.e., where oxygen, nitrogen, sulfur or phosphorous atoms replaces one or more hydrocarbon backbone carbon atoms, particularly where the substitution does not adversely impact the efficacy of the resulting compound.

Straight or branched alkyl groups may have six or fewer carbon atoms in their backbone (e.g., $C_1$-$C_6$ for straight chain, $C_3$-$C_6$ for branched chain), and more preferably four or fewer. Preferred cycloalkyl groups have from three to eight carbon atoms in their ring structure, and more preferably five or six carbons in the ring structure. "$C_1$-$C_6$" includes alkyl groups containing one to six carbon atoms.

"Substituted alkyls" refers to alkyl moieties having substituents replacing a hydrogen on one or more carbons of the hydrocarbon backbone. Such substituents can include alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylam inocarbonyl, dialkylam inocarbonyl, alkylthiocarbonyl, alkoxyl, phosphate, phosphonato, phosphinato, cyano, amino, acylamino, amidino, imino, sulfhydryl, alkylthio, thiocarboxylate, sulfates, alkylsulfinyl, sulfonato, sulfamoyl, sulfonamido, nitro, trifluoromethyl, cyano, azido, or heterocyclyl.

"Aryl" includes groups with aromaticity, including 5- and 6-membered unconjugated (i.e., single-ring) aromatic groups that may include from zero to four heteroatoms, as well as conjugated (i.e., multicyclic) systems having at least one ring that is aromatic. Examples of aryl groups include benzene, phenyl, tolyl and the like. Multicyclic aryl groups include tricyclic and bicyclic systems, e.g., naphthalene, benzoxazole, benzodioxazole, benzothiazole, benzoimidazole, benzothiophene, methylenedioxyphenyl, quinoline, isoquinoline, napthridine, indole, benzofuran, purine, benzofuran, deazapurine, indolizine, tetralin, and methylenedioxyphenyl.

Aryl groups having heteroatoms in the ring structure may also be referred to as "aryl heterocycles", "heterocycles," "heteroaryls" or "heteroaromatics"; e.g., pyrrole, furan, thiophene, thiazole, isothiazole, imidazole, triazole, tetrazole, pyrazole, oxazole, isooxazole, pyridine, pyrazine, pyridazine, and pyrimidine. The aromatic ring can be substituted at one or more ring positions with, for example, halogen, hydroxyl, alkoxy, alkylcarbonyloxy, arylcarbonyloxy, alkoxycarbonyloxy, aryloxycarbonyloxy, carboxylate, alkylcarbonyl, alkylam inocarbonyl, aralkylam inocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, cyano, amino, acylamino, amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

An "alkylaryl" or an "aralkyl" moiety is an alkyl substituted with an aryl group (e.g., phenylmethyl (benzyl)).

"Alkenyl" includes unsaturated aliphatic groups analogous in length and possible substitution to the alkyls described above, but that contain at least one double bond. For example, the term "alkenyl" includes straight-chain alkenyl groups (e.g., ethenyl, propenyl, butenyl, pentenyl, hexenyl, heptenyl, octenyl, nonenyl, and decenyl), branched-chain alkenyl groups, cycloalkenyl groups such as cyclopropenyl, cyclopentenyl, cyclohexenyl, cycloheptenyl, and cyclooctenyl; alkyl or alkenyl-substituted cycloalkenyl groups, and cycloalkyl or cycloalkenyl-substituted alkenyl groups.

"Alkenyl" groups may also optionally include heteroatoms, i.e., where oxygen, nitrogen, sulfur or phosphorous atoms replaces one or more hydrocarbon backbone carbon atoms, particularly where the substitution does not adversely impact the efficacy of the resulting compound.

Straight or branched alkenyl groups may have six or fewer carbon atoms in their backbone (e.g., $C_2$-$C_6$ for straight chain, $C_3$-$C_6$ for branched chain.) Preferred cycloalkenyl groups have from three to eight carbon atoms in their ring structure, and more preferably have five or six carbons in the ring structure. The term "$C_2$-$C_6$" includes alkenyl groups containing two to six carbon atoms.

"Substituted alkenyls" refers to alkenyl moieties having substituents replacing a hydrogen on one or more hydrocarbon backbone carbon atoms. Such substituents can include alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino, acylamino, amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, or heterocyclyl.

"Alkynyl" includes unsaturated aliphatic groups analogous in length and possible substitution to the alkyls described above, but which contain at least one triple bond. For example, "alkynyl" includes straight-chain alkynyl groups (e.g., ethynyl, propynyl, butynyl, pentynyl, hexynyl, heptynyl, octynyl, nonynyl, decynyl), branched-chain alkynyl groups, and cycloalkyl or cycloalkenyl substituted alkynyl groups.

"Alkynyl" groups may also optionally include heteroatoms, i.e., where oxygen, nitrogen, sulfur or phosphorous atoms replaces one or more hydrocarbon backbone carbon atoms, particularly where the substitution does not adversely impact the efficacy of the resulting compound Straight or branched chain alkynyls group may have six or fewer carbon atoms in their backbone (e.g., $C_2$-$C_6$ for straight chain, $C_3$-$C_6$ for branched chain). The term "$C_2$-$C_6$" includes alkynyl groups containing two to six carbon atoms.

"Substituted alkynyls" refers to alkynyl moieties having substituents replacing a hydrogen on one or more hydrocarbon backbone carbon atoms. Such substituents can include alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, or heterocyclyl.

Unless the number of carbons is otherwise specified, "lower alkyl" includes an alkyl group, as defined above, but having from one to ten, more preferably from one to six, carbon atoms in its backbone structure. "Lower alkenyl" and "lower alkynyl" have chain lengths of, for example, 2-5 carbon atoms.

"Acyl" includes compounds and moieties which contain the acyl radical ($CH_3CO$—) or a carbonyl group. "Substituted acyl" includes acyl groups where one or more of the hydrogen atoms are replaced by for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

"Acylamino" includes moieties wherein an acyl moiety is bonded to an amino group. For example, the term includes alkylcarbonylamino, arylcarbonylamino, carbamoyl and ureido groups. "Alkylamino" includes moieties wherein an alkyl moiety is bonded to an amino group; "dialkylamino", "arylamino", "diarylamino", and "alkylarylamino" are analogously named. In some embodiments, "amino" may include acylamino and/or alkylamino groups.

"Alkoxyalkyl", "alkylaminoalkyl" and "thioalkoxyalkyl" include alkyl groups, as described above, which further include oxygen, nitrogen or sulfur atoms replacing one or more hydrocarbon backbone carbon atoms, e.g., oxygen, nitrogen or sulfur atoms.

"Alkoxy" includes alkyl, alkenyl, and alkynyl groups covalently linked to an oxygen atom. Examples of alkoxy groups include methoxy, ethoxy, isopropyloxy, propoxy, butoxy, and pentoxy groups. Examples of "substituted alkoxy" groups include halogenated alkoxy groups. Substituted alkoxy groups can include alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino, acylamino, amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, or heterocyclyl substituents. Examples of halogen-substituted alkoxy groups include fluoromethoxy, difluoromethoxy, trifluoromethoxy, chloromethoxy, dichloromethoxy, and trichloromethoxy.

The terms "heterocyclyl" or "heterocyclic group" include closed ring structures, e.g., 3- to 10-, or 4- to 7-membered rings which include one or more heteroatoms. Heterocyclyl groups can be saturated or unsaturated and include pyrrolidine, oxolane, thiolane, piperidine, piperizine, morpholine, lactones, lactams such as azetidinones and pyrrolidinones, sultams, sultones, and the like.

Heterocyclic rings may be substituted at one or more positions with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino, acylamino, amidino, imino, sulfhydryl, alkylthio, arylthio, thiocarboxylate, sulfates, sulfonato, sulfamoyl, sulfonamido, nitro, trifluoromethyl, cyano, azido, heterocyclyl, or an aromatic or heteroaromatic moiety.

The term "thiocarbonyl" or "thiocarboxy" includes compounds and moieties which contain a carbon connected with a double bond to a sulfur atom.

The term "ether" includes compounds or moieties which contain an oxygen bonded to two different carbon atoms or heteroatoms. For example, the term includes "alkoxyalkyl" which refers to an alkyl, alkenyl, or alkynyl group covalently bonded to an oxygen atom which is covalently bonded to another alkyl group.

The term "ester" includes compounds and moieties which contain a carbon or a heteroatom bound to an oxygen atom which is bonded to the carbon of a carbonyl group. The term "ester" includes alkoxycarboxy groups such as methoxycarbonyl, ethoxycarbonyl, propoxycarbonyl, butoxycarbonyl, pentoxycarbonyl, etc. The alkyl, alkenyl, or alkynyl groups are as defined above.

The term "thioether" includes compounds and moieties which contain a sulfur atom bonded to two different carbon or heteroatoms. Examples of thioethers include, but are not limited to alkthioalkyls, alkthioalkenyls, and alkthioalkynyls. The term "alkthioalkyls" include compounds with an alkyl, alkenyl, or alkynyl group bonded to a sulfur atom which is bonded to an alkyl group. Similarly, the term "alkthioalkenyls" and alkthioalkynyls" refer to compounds or moieties wherein an alkyl, alkenyl, or alkynyl group is bonded to a sulfur atom which is covalently bonded to an alkynyl group.

The term "hydroxy" or "hydroxyl" includes groups with an —OH or —O$^-$.

The term "halogen" includes fluorine, bromine, chlorine, iodine, etc. The term "perhalogenated" generally refers to a moiety wherein all hydrogens are replaced by halogen atoms.

"Heteroatom" includes atoms of any element other than carbon or hydrogen. Examples of heteroatoms include nitrogen, oxygen, sulfur and phosphorus.

"At least partially aromatic bicyclic ring system", means a bicyclic ring system where either or both of the rings forming the bicycle are aromatic.

It will be noted that the structure of some of the compounds of the invention includes asymmetric carbon atoms. It is to be understood accordingly that the isomers arising from such asymmetry (e.g., all enantiomers and diastereomers) are included within the scope of the invention, unless indicated otherwise. Such isomers can be obtained in substantially pure form by classical separation techniques and by stereochemically controlled synthesis. Furthermore, the structures and other compounds and moieties discussed in this application also include all tautomers thereof. Alkenes can include either the E- or Z-geometry, where appropriate.

"Combination therapy" (or "co-therapy") includes the administration of a S1P receptor modulator of the invention and at least a second agent as part of a specific treatment regimen intended to provide the beneficial effect from the co-action of these therapeutic agents. The beneficial effect of the combination includes, but is not limited to, pharmacokinetic or pharmacodynamic co-action resulting from the combination of therapeutic agents. Administration of these therapeutic agents in combination typically is carried out over a defined time period (usually minutes, hours, days or weeks depending upon the combination selected). "Combination therapy" may, but generally is not, intended to encompass the administration of two or more of these therapeutic agents as part of separate monotherapy regimens that incidentally and arbitrarily result in the combinations of the present invention. "Combination therapy" is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single capsule having a fixed ratio of each therapeutic agent or in multiple, single capsules for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. The sequence in which the therapeutic agents are administered is not narrowly critical. "Combination therapy" also can embrace the administration of the therapeutic agents as described above in further combination with other biologically active ingredients and non-drug therapies (e.g., surgery or radiation treatment.) Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

An "anionic group," as used herein, refers to a group that is negatively charged at physiological pH. Preferred anionic groups include carboxylate, sulfate, sulfonate, sulfinate, sulfamate, tetrazolyl, phosphate, phosphonate, phosphinate, or phosphorothioate or functional equivalents thereof. "Functional equivalents" of anionic groups are intended to include bioisosteres, e.g., bioisosteres of a carboxylate group. Bioisosteres encompass both classical bioisosteric equivalents and non-classical bioisosteric equivalents. Classical and non-classical bioisosteres are known in the art (see, e.g., Silverman, R. B. *The Organic Chemistry of Drug Design and Drug Action*, Academic Press, Inc.: San Diego, Calif., 1992, pp.19-23). A particularly preferred anionic group is a carboxylate.

The term "heterocyclic group" is intended to include closed ring structures in which one or more of the atoms in the ring is an element other than carbon, for example, nitrogen, or oxygen or sulfur. Heterocyclic groups can be saturated or unsaturated and heterocyclic groups such as pyrrole and furan can have aromatic character. They include fused ring structures such as quinoline and isoquinoline. Other examples of heterocyclic groups include pyridine and purine. Heterocyclic groups can also be substituted at one or more constituent atoms with, for example, a halogen, a lower alkyl, a lower alkenyl, a lower alkoxy, a lower alkylthio, a lower alkylamino, a lower alkylcarboxyl, a nitro, a hydroxyl, —$CF_3$, —CN, or the like.

An "S1P-modulating agent" includes compound or compositions capable of inducing a detectable change in S1P receptor activity in vivo or in vitro, e.g., at least 10% increase or decrease in S1P activity as measured by a given assay such as the bioassay described hereinbelow.

"$EC_{50}$ of an agent" included that concentration of an agent at which a given activity, including binding of sphingosine or other ligand of an S1P receptor and/or a functional activity of a S1P receptor (e.g., a signaling activity), is 50% maximal for that S1P receptor. Stated differently, the $EC_{50}$ is the concentration of agent that gives 50% activation, when 100% activation is set at the amount of activity of the S1P receptor which does not increase with the addition of more ligand/agonist and 0% activation is set at the amount of activity in the assay in the absence of added ligand/agonist.

"Purified" and like terms relate to the isolation of a molecule or compound in a form that is substantially free of contaminants normally associated with the molecule or compound in a native or natural environment.

An "effective amount" includes an amount sufficient to produce a selected effect. For example, an effective amount of an S1P receptor antagonist is an amount that decreases the cell signaling activity of the S1P receptor.

"Immunomodulation" includes effects on the functioning of the immune system, and includes both the enhancement of an immune response as well as suppression of the immune response.

The compounds of the invention and the other pharmacologically active agent may be is administered to a patient simultaneously, sequentially or in combination. It will be appreciated that when using a combination of the invention, the compound of the invention and the other pharmacologically active agent may be in the same pharmaceutically acceptable carrier and therefore administered simultaneously. They may be in separate pharmaceutical carriers such as conventional oral dosage forms which are taken simultaneously. The term "combination" further refers to the case where the compounds are provided in separate dosage forms and are administered sequentially.

The compounds of the invention may be administered to patients (animals and humans) in need of such treatment in dosages that will provide optimal pharmaceutical efficacy. It will be appreciated that the dose required for use in any particular application will vary from patient to patient, not only with the particular compound or composition selected, but also with the route of administration, the nature of the condition being treated, the age and condition of the patient, concurrent medication or special diets then being followed by the patient, and other factors which those skilled in the art will recognize, with the appropriate dosage ultimately being at the discretion of the attendant physician.

An appropriate dosage level will generally be about 0.001 to 50 mg per kg patient body weight per day, which may be administered in single or multiple doses. Preferably, the dosage level will be about 0.01 to about 25 mg/kg per day; more preferably about 0.05 to about 10 mg/kg per day. For example, in the treatment or prevention of a disorder of the central nervous system, a suitable dosage level is about 0.001 to 10 mg/kg per day, preferably about 0.005 to 5 mg/kg per day, and especially about 0.01 to 1 mg/kg per day. The compounds may be administered on a regimen of 1 to 4 times per day, preferably once or twice per day.

It will be appreciated that the amount of the compound of the invention required for use in any treatment will vary not only with the particular compounds or composition selected but also with the route of administration, the nature of the condition being treated, and the age and condition of the patient, and will ultimately be at the discretion of the attendant physician.

The compositions and combination therapies of the invention may be administered in combination with a variety of pharmaceutical excipients, including stabilizing agents, carriers and/or encapsulation formulations as described herein.

Aqueous compositions of the present invention comprise an effective amount of the compounds of the invention, dissolved or dispersed in a pharmaceutically acceptable carrier or aqueous medium.

"Pharmaceutically or pharmacologically acceptable" include molecular entities and compositions that do not produce an adverse, allergic or other untoward reaction when administered to an animal, or a human, as appropriate. "Pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

For human administration, preparations should meet sterility, pyrogenicity, general safety and purity standards as required by FDA Office of Biologics standards.

The compositions and combination therapies of the invention will then generally be formulated for parenteral administration, e.g., formulated for injection via the intravenous, intramuscular, subcutaneous, intralesional, or even intraperitoneal routes. The preparation of an aqueous composition that contains a composition of the invention or an active component or ingredient will be known to those of skill in the art in light of the present disclosure. Typically, such compositions can be prepared as injectables, either as liquid solutions or suspensions; solid forms suitable for using to prepare solutions or suspensions upon the addition of a liquid prior to injection can also be prepared; and the preparations can also be emulsified.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi.

Solutions of active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

Therapeutic or pharmacological compositions of the present invention will generally comprise an effective amount of the component(s) of the combination therapy, dissolved or dispersed in a pharmaceutically acceptable medium. Pharmaceutically acceptable media or carriers include any and all solvents, dispersion media, coatings, antibacterial and antifungal agents, isotonic and absorption delaying agents and the like. The use of such media and agents for pharmaceutical active substances is well known in the art. Supplementary active ingredients can also be incorporated into the therapeutic compositions of the present invention.

The preparation of pharmaceutical or pharmacological compositions will be known to those of skill in the art in light of the present disclosure. Typically, such compositions may be prepared as injectables, either as liquid solutions or suspensions; solid forms suitable for solution in, or suspension in, liquid prior to injection; as tablets or other solids for oral administration; as time release capsules; or in any other form currently used, including cremes, lotions, mouthwashes, inhalants and the like.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The preparation of more, or highly, concentrated solutions for intramuscular injection is also contemplated. In this regard, the use of DMSO as solvent is preferred as this will result in extremely rapid penetration, delivering high concentrations of the active compound(s) or agent(s) to a small area.

The use of sterile formulations, such as saline-based washes, by surgeons, physicians or health care workers to cleanse a particular area in the operating field may also be particularly useful. Therapeutic formulations in accordance with the present invention may also be reconstituted in the form of mouthwashes, or in conjunction with antifungal reagents. Inhalant forms are also envisioned. The therapeutic formulations of the invention may also be prepared in forms suitable for topical administration, such as in cremes and lotions.

Suitable preservatives for use in such a solution include benzalkonium chloride, benzethonium chloride, chlorobutanol, thimerosal and the like. Suitable buffers include boric acid, sodium and potassium bicarbonate, sodium and potassium borates, sodium and potassium carbonate, sodium acetate, sodium biphosphate and the like, in amounts sufficient to maintain the pH at between about pH 6 and pH 8, and preferably, between about pH 7 and pH 7.5. Suitable tonicity agents are dextran 40, dextran 70, dextrose, glycerin, potassium chloride, propylene glycol, sodium chloride, and the like, such that the sodium chloride equivalent of the ophthalmic solution is in the range 0.9 plus or minus 0.2%. Suitable antioxidants and stabilizers include sodium bisulfite, sodium metabisulfite, sodium thiosulfite, thiourea and the like. Suitable wetting and clarifying agents include polysorbate 80, polysorbate 20, poloxamer 282 and tyloxapol. Suitable viscosity-increasing agents include dextran 40, dextran 70, gelatin, glycerin, hydroxyethylcellulose, hydroxmethylpropylcellulose, lanolin, methylcellulose, petrolatum, polyethylene glycol, polyvinyl alcohol, polyvinylpyrrolidone, carboxymethylcellulose and the like.

Upon formulation, therapeutics will be administered in a manner compatible with the dosage formulation, and in such amount as is pharmacologically effective. The formulations are easily administered in a variety of dosage forms, such as the type of injectable solutions described above, but drug release capsules and the like can also be employed.

In this context, the quantity of active ingredient and volume of composition to be administered depends on the host animal to be treated. Precise amounts of active compound required for administration depend on the judgment of the practitioner and are peculiar to each individual.

A minimal volume of a composition required to disperse the active compounds is typically utilized. Suitable regimes for administration are also variable, but would be typified by initially administering the compound and monitoring the results and then giving further controlled doses at further intervals. For example, for parenteral administration, a suitably buffered, and if necessary, isotonic aqueous solution would be prepared and used for intravenous, intramuscular, subcutaneous or even intraperitoneal administration. One dosage could be dissolved in 1 ml of isotonic NaCl solution and either added to 1000 ml of hypodermolysis fluid or injected at the proposed site of infusion, (see for example, *Remington's Pharmaceutical Sciences* 15th Edition, pages 1035-1038 and 1570-1580).

In certain embodiments, active compounds may be administered orally. This is contemplated for agents which are generally resistant, or have been rendered resistant, to proteolysis by digestive enzymes. Such compounds are contemplated to include chemically designed or modified agents; dextrorotatory peptides; and peptide and liposomal formulations in time release capsules to avoid peptidase and lipase degradation.

The carrier can also be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze drying techniques which yield a powder of the active ingredient plus any additional desired ingredient from a previously sterile-filtered solution thereof.

The preparation of more, or highly, concentrated solutions for direct injection is also contemplated, where the use of DMSO as solvent is envisioned to result in extremely rapid penetration, delivering high concentrations of the active agents to a small area.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure.

In addition to the compounds formulated for parenteral administration, such as intravenous or intramuscular injection, other pharmaceutically acceptable forms include, e.g., tablets or other solids for oral administration; liposomal formulations; time-release capsules; and any other form currently used, including cremes.

Additional formulations suitable for other modes of administration include suppositories. For suppositories, traditional binders and carriers may include, for example, polyalkylene glycols or triglycerides; such suppositories may be formed from mixtures containing the active ingredient in the range of 0.5% to 10%, preferably 1%-2%.

Oral formulations include such normally employed excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders.

In certain defined embodiments, oral pharmaceutical compositions will comprise an inert diluent or assimilable edible carrier, or they may be enclosed in hard or soft shell gelatin capsule, or they may be compressed into tablets, or they may be incorporated directly with the food of the diet. For oral therapeutic administration, the active compounds may be incorporated with excipients and used in the form of ingestible tablets, buccal tables, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 75% of the weight of the unit, or preferably between 25-60%. The amount of active compounds in such therapeutically useful compositions is such that a suitable dosage will be obtained.

The tablets, troches, pills, capsules and the like may also contain the following: a binder, as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup of elixir may contain the active compounds sucrose as a sweetening agent methyl and propylparabens as preservatives, a dye and flavoring, such as cherry or orange flavor.

The pharmaceutical compositions of this invention may be used in the form of a pharmaceutical preparation, for example, in solid, semisolid or liquid form, which contains one or more of the compound of the invention, as an active ingredient, in admixture with an organic or inorganic carrier or excipient suitable for external, enteral or parenteral applications. The active ingredient may be compounded, for example, with the non-toxic, pharmaceutically acceptable carriers for tablets, pellets, capsules, suppositories, solutions, emulsions, suspensions, and any other form suitable for use. The carriers which can be used are water, glucose, lactose, gum acacia, gelatin, mannitol, starch paste, magnesium trisilicate, talc, corn starch, keratin, colloidal silica, potato starch, urea and other carriers suitable for use in manufacturing preparations, in solid, semisolid, or liquid form, and in addition auxiliary, stabilizing, thickening and coloring agents and perfumes may be used. The active object compound is included in the pharmaceutical composition in an amount sufficient to produce the desired effect upon the process or condition of the disease.

For preparing solid compositions such as tablets, the principal active ingredient is mixed with a pharmaceutical carrier, e.g., conventional tableting ingredients such as corn starch, lactose, sucrose, sorbitol, talc, stearic acid, magnesium stearate, dicalcium phosphate or gums, and other pharmaceutical diluents, e.g., water, to form a solid preformulation composition containing a homogeneous mixture of a compound of the invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the compositions of the invention may be incorporated for administration orally or by injection include aqueous solution, suitably flavored syrups, aqueous or oil suspensions, and emulsions with acceptable oils such as cottonseed oil, sesame oil, coconut oil or peanut oil, or with a solubilizing or emulsifying agent suitable for intravenous use, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. Preferably the compositions are administered by the oral or nasal respiratory route for local or systemic effect. Compositions in preferably sterile pharmaceutically acceptable solvents may be nebulized by use of inert gases. Nebulized solutions may be breathed directly from the nebulizing device or the nebulizing device may be attached to a face mask, tent or intermittent positive pressure breathing machine. Solution, suspension or powder compositions may be administered, preferably orally or nasally, from devices which deliver the formulation in an appropriate manner.

For treating clinical conditions and diseases noted above, the compound of this invention may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques.

The compounds of the present invention are high affinity agonists (or antagonists) at various S1P receptors. The compounds of the invention are also expected to evoke lymphopenia when introduced into rodents, non human primate or humans. Thus the compounds of the invention can be used as immune modulators, and are useful in treating or preventing pathologies mediated by lymphocyte actions, including acute or chronic rejection of tissue grafts such as organ transplants, and autoimmune diseases. Autoimmune diseases that may be treated with compounds of the invention include: systemic lupus erythematosus, multiple sclerosis, Behcet's disease, glomerulonephritis, rheumatoid arthritis, inflammatory bowel diseases such as Crohn's disease and ulcerative colitis, type I diabetes, uveitis, psoriasis, myasthenia gravis, Hashimoto's thyroiditis, autoimmune hemolytic anemia, autoimmune thrombocytopenic purpura, hepatitis and Wegner's granuloma.

The compounds of the invention are useful also in treating inflammatory disorders, including atopic asthma, inflammatory glomerular injury and ischemia-reperfusion injury.

Lysophospholipids, S1P and lysophosphatidic acid (LPA), stimulate cellular proliferation and affect numerous cellular functions by signaling through G protein-coupled endothelial differentiation gene-encoded (S1P) receptors. Accordingly, the S1P receptor modulators of the invention are anticipated to have utility in immunomodulation, e.g., in anti-angiogenesis therapy, such as in neoplastic disease treatment.

In one embodiment of the invention, a pharmaceutical composition comprising one or more of the S1P receptor agonists of the present invention is administered to a mammalian species, including humans, to enhance wound repair, improve neuronal function or enhance an immune response of that species. It has also been reported that S1P inhibits fibrosis in various organs. Accordingly, the S1P receptor agonists of the invention can be used to prevent/treat diseases associated with organ fibrosis, such as pulmonary fibrosis, interstitial pneumonia, chronic hepatitis, hepatic cirrhosis, chronic renal insufficiency or kidney glomerular sclerosis. In one embodiment, a composition comprising an S1P receptor agonist of the present invention is used to treat wounds, including burns, cuts, lacerations, surgical incisions, bed sores, and slow-healing ulcers such as those seen in diabetics.

In addition, S1P modulating compounds of the invention are believed to mobilize lymphocytes and increase their homing to secondary lymphoid tissues. Thus the present compounds can be used to direct lymphocytes away from transplanted organs, e.g., allografts, or healthy cells, e.g., pancreatic islets as in type I diabetes, myelin sheathing (multiple sclerosis), or other tissues that may be subjected to an undesirable immunoresponse, and thus decrease damage to such tissues from the immune system.

In another embodiment, the S1P receptor-modulating compounds of the invention are administered to a subject to treat or prevent a disorder of abnormal cell growth and differentiation. These disorders include Alzheimer's disease, aberrant corpus luteum formation, osteoporosis, anovulation, Parkinson's disease, and cancer. In one embodiment, an S1P antagonist is administered to a patient to treat a disease associated with abnormal growth.

In one embodiment, the compounds of the invention are used as immunomodulators to alter immune system activities and prevent damage to healthy tissue that would otherwise occur in autoimmune diseases and in organ transplantation. In particular, the compounds can be administered to patients as part of the treatment associated with organ transplantation, including pancreas, pancreatic islets, kidney, heart and lung transplantations. The S1P modulators can be administered alone or in combination with known immunosuppressants such as cyclosporine, tacrolimus, rapamycin, azathioprine, cyclophosphamide, methotrexate and corticosteroids such as cortisone, des-oxymetasone, betametasone, desametasone, flunisolide, prednisolone, prednisone, amcinomide, desonide, methylprednisolone, triamcinolone, and alclometasone.

S1P also acts as a survival factor in many cell types. In particular, compounds of the invention having S1P antagonistic activity are anticipated to be useful in protecting cells and tissues from hypoxic conditions. In accordance with one embodiment, compounds of the invention are administered to a patient judged to be or actually in need of treatment, to treat cells and tissues exposed to hypoxic conditions, including injury sustained as a result of ischemia. In accordance with one embodiment, compounds of the invention that show S1P receptor antagonist activity can be used to treat ischemia reperfusion type injury. Interference with the supply of oxygenated blood to tissues is defined as ischemia. The effects of ischemia are known to be progressive, so that over time cellular vitality continues to deteriorate and tissues become necrotic. Total persistent ischemia, with limited oxygen perfusion of tissues, results in cell death and eventually in coagulation-induced necrosis despite reperfusion with arterial blood. Evidence indicates that a significant proportion of the injury associated with ischemia is a consequence of the events associated with reperfusion of ischemic tissues, hence the term reperfusion injury.

Pharmaceutical compositions comprising the compounds of the invention may be administered to an individual in need by any number of routes, including topical, oral, intravenous, intramuscular, intra-arterial, intramedullary, intrathecal, intraventricular, transdermal, subcutaneous, intraperitoneal, intranasal, enteral, topical, sublingual, or rectal means. The oral route is typically employed for most conditions requiring the compounds of the invention. Preference is given to intravenous injection or infusion for the acute treatments. For maintenance regimens the oral or parenteral, e.g., intramuscular or subcutaneous, route is preferred. In accordance with one embodiment a composition is provided that comprises a compound of invention and albumin, e.g., a compound of the present invention, a pharmaceutically acceptable carrier and 0.1-1.0% albumin. Albumin functions as a buffer and improves the solubility of the compounds.

The invention also provides a pharmaceutical pack or kit comprising one or more containers filled with one or more of the ingredients of the pharmaceutical compositions of the invention. In accordance with one embodiment, a kit is provided for treating a patient in need of immunomodulation, including instructions for use of the kit. In this embodiment the kit comprises one or more of the S1P modulators of the invention, and may also include one or more known immunosuppressants. These pharmaceuticals can be packaged in a variety of containers, e.g., vials, tubes, microtiter well plates, bottles, and the like. Other reagents can be included in separate containers and provided with the kit; e.g., positive control samples, negative control samples, buffers, cell culture media, etc. Preferably, the kits will also include instructions for use.

The activity of compounds of the invention may be determined by using an assay for detecting S1P receptor activity (such as the [γ-35 S]GTP binding assay) and assaying for activity in the presence of S1P and the test compound. More particularly, in the method described by Traynor et al., 1995, *Mol. Pharmacol.* 47: 848-854, incorporated herein by reference, G-protein coupling to membranes can be evaluated by measuring the binding of labeled GTP.

For example, samples comprising membranes isolated from cells expressing an S1P polypeptide can be incubated in a buffer promoting binding of the polypeptide to ligand (i.e. S1P), in the presence of radiolabeled GTP and unlabeled GDP (e.g., in 20 mM HEPES, pH 7.4, 100 mM NaCl, and 10 mM $MgCl_2$, 80 pM $^{35}$S-GTP$_\gamma$S and 3 μM GDP), with and without a candidate modulator. The assay mixture is incubated for a suitable period of time to permit binding to and activation of the receptor (e.g., 60 minutes at 30° C.), after which time unbound labeled GTP is removed (e.g., by filtration onto GF/B filters). Bound, labeled GTP can be measured by liquid scintillation counting. A decrease of 10% or more in labeled GTP binding as measured by scintillation counting in a sample containing a candidate modulator, relative to a sample without the modulator, indicates that the candidate modulator is an inhibitor of S1P receptor activity.

A similar GTP-binding assay can be performed without the presence of the ligand (S1P) to identify agents that act as agonists. In this case, ligand-stimulated GTP binding is used as a standard. An agent is considered an agonist if it induces at least 50% of the level of GTP binding induced by S1P when the agent is present at 10 μm or less, and preferably will induce a level which is the same as or higher than that induced by the ligand.

GTPase activity can be measured by incubating cell membrane extracts containing an S1P receptor with $\gamma^{32}$P-GTP. Active GTPase will release the label as inorganic phosphate, which can be detected by separation of free inorganic phosphate in a 5% suspension of activated charcoal in 20 mM $H_3PO_4$, followed by scintillation counting. Controls would include assays using membrane extracts isolated from cells not expressing an S1P receptor (e.g., mock-transfected cells), in order to exclude possible non-specific effects of the candidate modulator. In order to assay for the effect of a candidate modulator on S1P-regulated GTPase activity, cell membrane samples can be incubated with the ligand (S1P), with and without the modulator, and a GTPase assay can be performed as described above. A change (increase or decrease) of 10% or more in the level of GTP binding or GTPase activity relative to samples without modulator is indicative of S1P modulation by a candidate modulator.

Identified S1P receptor agonists and antagonists can be used to treat a variety of human diseases and disorders, including, but not limited to the treatment of infections such as bacterial, fungal, protozoan and viral infections, particularly infections caused by HIV-1 or HIV-2; pain; cancers; diabetes, obesity; anorexia; bulimia; asthma; Parkinson's disease; acute heart failure; hypotension; hypertension; urinary retention; osteoporosis; angina pectoris; myocardial infarction; stroke; ulcers; asthma; allergy; benign prostatic hypertrophy; migraine; vomiting; psychotic and neurological disorders, including anxiety, schizophrenia, manic depression, depression, delirium, dementia, and severe mental retardation.

Pain is a complex subjective sensation reflecting real or potential tissue damage and the affective response to it. Acute pain is a physiological signal indicating a potential or actual injury. Chronic pain can either be somatogenetic (organic) or psychogenic. Chronic pain is frequently accompanied or followed by vegetative signs, which often result in depression.

Somatogenetic pain may be of nociceptive origin, inflammatory or neuropathic. Nociceptive pain is judged to be commensurate with ongoing activation of somatic or visceral pain-sensitive nerve fibers. Neuropathic pain results from dysfunction in the nervous system; it is believed to be sustained by aberrant somatosensory processes in the peripheral nervous system, the CNS, or both. Chronic pain results in individual suffering and social economic costs of tremendous extent. Existing pharmacological pain therapies are widely unsatisfying both in terms of efficacy and of safety.

In one embodiment, S1P modulators of the present invention are used as immunomodulators to suppress the immune system and prevent damage to healthy tissue that would otherwise occur in autoimmune diseases and in organ transplantation. The compounds can be administered to patients as part of the treatment associated with organ transplantation, including pancreas, pancreatic islets, kidney, heart and lung transplantations. The S1P modulators can be administered alone or in combination with known immunosuppressants such as cyclosporine, tacrolimus, azatioprine, desoxymetasone, cyclophosphamide, cortisone, betametasone, FK 506 (a fungal macrolide immunosuppressant), desametasone, flunisolide, prednisolone, prednisone, amcinomide desonide, methylprednisolone, triamcinolone, alclometasone and methotrexate.

The dosage to be used is, of course, dependent on the specific disorder to be treated, as well as additional factors including the age, weight, general state of health, severity of the symptoms, frequency of the treatment and whether additional pharmaceuticals accompany the treatment. The dosages are in general administered several times per day and preferably one to three times per day. The amounts of the individual active compounds are easily determined by routine procedures known to those of ordinary skill in the art S1P also acts as a survival factor in many cell types. S1P receptor modulators are anticipated to have activity in protecting cells and tissues from hypoxic conditions. In accordance with one embodiment compounds of the invention are administered to treat cells and tissues exposed to hypoxic conditions, including injury sustained as a result of ischemia. In accordance with one embodiment, the S1P modulators having antagonistic activity can be used to treat ischemia reperfusion type injury. Interference with the supply of oxygenated blood to tissues is defined as ischemia. The effects of ischemia are known to be progressive, such that over time cellular vitality continues to deteriorate and tissues become necrotic. Total persistent ischemia, with limited oxygen perfusion of tissues, results in cell death and eventually in coagulation-induced necrosis despite reperfusion with arterial blood.

The compounds of the invention and the other pharmacologically active agent may be administered to a patient simultaneously, sequentially or in combination. It will be appreciated that when using a combination of the invention, the compound of the invention and the other pharmacologically active agent may be in the same pharmaceutically acceptable carrier and therefore administered simultaneously. They may be in separate pharmaceutical carriers such as conventional oral dosage forms which are taken simultaneously. The term "combination" further refers to the case where the compounds are provided in separate dosage forms and are administered sequentially.

The compounds of the invention may be administered to patients (animals and humans) in need of such treatment in dosages that will provide optimal pharmaceutical efficacy. It will be appreciated that the dose required for use in any particular application will vary from patient to patient, not only with the particular compound or composition selected, but also with the route of administration, the nature of the condition being treated, the age and condition of the patient, concurrent medication or special diets then being followed by the patient, and other factors which those skilled in the art will recognize, with the appropriate dosage ultimately being at the discretion of the attendant physician.

An appropriate dosage level will generally be about 0.001 to 50 mg per kg patient body weight per day, which may be administered in single or multiple doses. Preferably, the dosage level will be about 0.01 to about 25 mg/kg per day; more preferably about 0.05 to about 10 mg/kg per day. For example, in the treatment or prevention of a disorder of the central nervous system, a suitable dosage level is about 0.001 to 10 mg/kg per day, preferably about 0.005 to 5 mg/kg per day, and especially about 0.01 to 1 mg/kg per day. The compounds may be administered on a regimen of 1 to 4 times per day, preferably once or twice per day.

It will be appreciated that the amount of the compound of the invention required for use in any treatment will vary not only with the particular compounds or composition selected but also with the route of administration, the nature of the condition being treated, and the age and condition of the patient, and will ultimately be at the discretion of the attendant physician.

The compositions and combination therapies of the invention may be administered in combination with a variety of pharmaceutical excipients, including stabilizing agents, carriers and/or encapsulation formulations as described herein.

Aqueous compositions of the present invention comprise an effective amount of the compounds of the invention, dissolved or dispersed in a pharmaceutically acceptable carrier or aqueous medium.

"Pharmaceutically or pharmacologically acceptable" include molecular entities and compositions that do not produce an adverse, allergic or other untoward reaction when administered to an animal, or a human, as appropriate. "Pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

For human administration, preparations should meet sterility, pyrogenicity, general safety and purity standards as required by FDA Office of Biologics standards.

The compositions and combination therapies of the invention will then generally be formulated for parenteral administration, e.g., formulated for injection via the intravenous, intramuscular, subcutaneous, intralesional, or even intraperitoneal routes. The preparation of an aqueous composition that contains a composition of the invention or an active component or ingredient will be known to those of skill in the art in light of the present disclosure. Typically, such compositions can be prepared as injectables, either as liquid solutions or suspensions; solid forms suitable for using to prepare solutions or suspensions upon the addition of a liquid prior to injection can also be prepared; and the preparations can also be emulsified.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi.

Solutions of active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

Therapeutic or pharmacological compositions of the present invention will generally comprise an effective amount of the component(s) of the combination therapy, dissolved or dispersed in a pharmaceutically acceptable medium. Pharmaceutically acceptable media or carriers include any and all solvents, dispersion media, coatings, antibacterial and antifungal agents, isotonic and absorption delaying agents and the like. The use of such media and agents for pharmaceutical active substances is well known in the art. Supplementary active ingredients can also be incorporated into the therapeutic compositions of the present invention.

The preparation of pharmaceutical or pharmacological compositions will be known to those of skill in the art in light of the present disclosure. Typically, such compositions may be prepared as injectables, either as liquid solutions or suspensions; solid forms suitable for solution in, or suspension in, liquid prior to injection; as tablets or other solids for oral administration; as time release capsules; or in any other form currently used, including cremes, lotions, mouthwashes, inhalants and the like.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The preparation of more, or highly, concentrated solutions for intramuscular injection is also contemplated. In this regard, the use of DMSO as solvent is preferred as this will result in extremely rapid penetration, delivering high concentrations of the active compound(s) or agent(s) to a small area.

The use of sterile formulations, such as saline-based washes, by surgeons, physicians or health care workers to cleanse a particular area in the operating field may also be particularly useful. Therapeutic formulations in accordance with the present invention may also be reconstituted in the form of mouthwashes, or in conjunction with antifungal reagents. Inhalant forms are also envisioned. The therapeutic formulations of the invention may also be prepared in forms suitable for topical administration, such as in cremes and lotions.

Suitable preservatives for use in such a solution include benzalkonium chloride, benzethonium chloride, chlorobutanol, thimerosal and the like. Suitable buffers include boric acid, sodium and potassium bicarbonate, sodium and potassium borates, sodium and potassium carbonate, sodium acetate, sodium biphosphate and the like, in amounts sufficient to maintain the pH at between about pH 6 and pH 8, and preferably, between about pH 7 and pH 7.5. Suitable tonicity agents are dextran 40, dextran 70, dextrose, glycerin, potassium chloride, propylene glycol, sodium chloride, and the like, such that the sodium chloride equivalent of the ophthalmic solution is in the range 0.9 plus or minus 0.2%. Suitable antioxidants and stabilizers include sodium bisulfite, sodium metabisulfite, sodium thiosulfite, thiourea and the like. Suitable wetting and clarifying agents include polysorbate 80, polysorbate 20, poloxamer 282 and tyloxapol. Suitable viscosity-increasing agents include dextran 40, dextran 70, gelatin, glycerin, hydroxyethylcellulose, hydroxmethylpropylcellulose, lanolin, methylcellulose, petrolatum, polyethylene glycol, polyvinyl alcohol, polyvinylpyrrolidone, carboxymethylcellulose and the like.

Upon formulation, therapeutics will be administered in a manner compatible with the dosage formulation, and in such amount as is pharmacologically effective. The formulations are easily administered in a variety of dosage forms, such as the type of injectable solutions described above, but drug release capsules and the like can also be employed.

In this context, the quantity of active ingredient and volume of composition to be administered depends on the host animal to be treated. Precise amounts of active compound required for administration depend on the judgment of the practitioner and are peculiar to each individual.

A minimal volume of a composition required to disperse the active compounds is typically utilized. Suitable regimes for administration are also variable, but would be typified by initially administering the compound and monitoring the results and then giving further controlled doses at further intervals. For example, for parenteral administration, a suitably buffered, and if necessary, isotonic aqueous solution would be prepared and used for intravenous, intramuscular, subcutaneous or even intraperitoneal administration. One dosage could be dissolved in 1 ml of isotonic NaCl solution and either added to 1000 ml of hypodermolysis fluid or injected at the proposed site of infusion, (see for example, *Remington's Pharmaceutical Sciences* 15th Edition, pages 1035-1038 and 1570-1580).

In certain embodiments, active compounds may be administered orally. This is contemplated for agents which are generally resistant, or have been rendered resistant, to proteolysis by digestive enzymes. Such compounds are contemplated to include chemically designed or modified agents; dextrorotatory peptides; and peptide and liposomal formulations in time release capsules to avoid peptidase and lipase degradation.

Pharmaceutically acceptable salts include acid addition salts and which are formed with inorganic acids such as, for example, hydrochloric, hydrobromic, boric, phosphoric, sulfuric acids or phosphoric acids, or such organic acids as acetic, oxalic, tartaric, maleic, fumaric, citric, succinic, mesylic, mandelic, succinic, benzoic, ascorbic, methanesulphonic, a-keto glutaric, a-glycerophosphoric, glucose-1-phosphoric acids and the like. Salts formed with the free carboxyl groups can also be derived from inorganic bases such as, for example, sodium, potassium, ammonium, calcium, magnesium, or ferric hydroxides, and such organic bases as isopropylamine, trimethylamine, histidine, procaine and the like. Other examples of pharmaceutically acceptable salts include quaternary derivatives, and internal salts such as N-oxides.

The carrier can also be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze drying techniques which yield a powder of the active ingredient plus any additional desired ingredient from a previously sterile-filtered solution thereof.

The preparation of more, or highly, concentrated solutions for direct injection is also contemplated, where the use of DMSO as solvent is envisioned to result in extremely rapid penetration, delivering high concentrations of the active agents to a small area.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure.

In addition to the compounds formulated for parenteral administration, such as intravenous or intramuscular injection, other pharmaceutically acceptable forms include, e.g., tablets or other solids for oral administration; liposomal formulations; time-release capsules; and any other form currently used, including cremes.

Additional formulations suitable for other modes of administration include suppositories. For suppositories, traditional binders and carriers may include, for example, polyalkylene glycols or triglycerides; such suppositories may be formed from mixtures containing the active ingredient in the range of 0.5% to 10%, preferably 1%-2%.

Oral formulations include such normally employed excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders.

In certain defined embodiments, oral pharmaceutical compositions will comprise an inert diluent or assimilable edible carrier, or they may be enclosed in hard or soft shell gelatin capsule, or they may be compressed into tablets, or they may be incorporated directly with the food of the diet. For oral therapeutic administration, the active compounds may be incorporated with excipients and used in the form of ingestible tablets, buccal tables, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 75% of the weight of the unit, or preferably between 25-60%. The amount of active compounds in such therapeutically useful compositions is such that a suitable dosage will be obtained.

The tablets, troches, pills, capsules and the like may also contain the following: a binder, as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup of elixir may contain the active compounds sucrose as a sweetening agent methyl and propylparabens as preservatives, a dye and flavoring, such as cherry or orange flavor.

The pharmaceutical compositions of this invention may be used in the form of a pharmaceutical preparation, for example, in solid, semisolid or liquid form, which contains one or more of the compound of the invention, as an active ingredient, in admixture with an organic or inorganic carrier or excipient suitable for external, enteral or parenteral applications. The active ingredient may be compounded, for example, with the usual non-toxic, pharmaceutically acceptable carriers for tablets, pellets, capsules, suppositories, solutions, emulsions, suspensions, and any other form suitable for use. The carriers which can be used are water, glucose, lactose, gum acacia, gelatin, mannitol, starch paste, magnesium trisilicate, talc, corn starch, keratin, colloidal silica, potato starch, urea and other carriers suitable for use in manufacturing preparations, in solid, semisolid, or liquid form, and in addition auxiliary, stabilizing, thickening and coloring agents and perfumes may be used. The active object compound is included in the pharmaceutical composition in an amount sufficient to produce the desired effect upon the process or condition of the disease.

For preparing solid compositions such as tablets, the principal active ingredient is mixed with a pharmaceutical carrier, e.g., conventional tableting ingredients such as corn starch, lactose, sucrose, sorbitol, talc, stearic acid, magnesium stearate, dicalcium phosphate or gums, and other pharmaceutical diluents, e.g., water, to form a solid preformulation composition containing a homogeneous mixture of a compound of the invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the compositions of the invention may be incorporated for administration orally or by injection include aqueous solution, suitably flavored syrups, aqueous or oil suspensions, and emulsions with acceptable oils such as cottonseed oil, sesame oil, coconut oil or peanut oil, or with a solubilizing or emulsifying agent suitable for intravenous use, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. Preferably the compositions are administered by the oral or nasal respiratory route for local or systemic effect. Compositions in preferably sterile pharmaceutically acceptable solvents may be nebulized by use of inert gases. Nebulized solutions may be breathed directly from the nebulizing device or the nebulizing device may be attached to a face mask, tent or intermittent positive pressure breathing machine. Solution, suspension or powder compositions may be administered, preferably orally or nasally, from devices which deliver the formulation in an appropriate manner.

For treating clinical conditions and diseases noted above, the compound of this invention may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques.

The following examples are given for the purpose of illustrating the invention, but not for limiting the scope or spirit of the invention.

Compounds of the invention may be prepared as described in the following schemes.

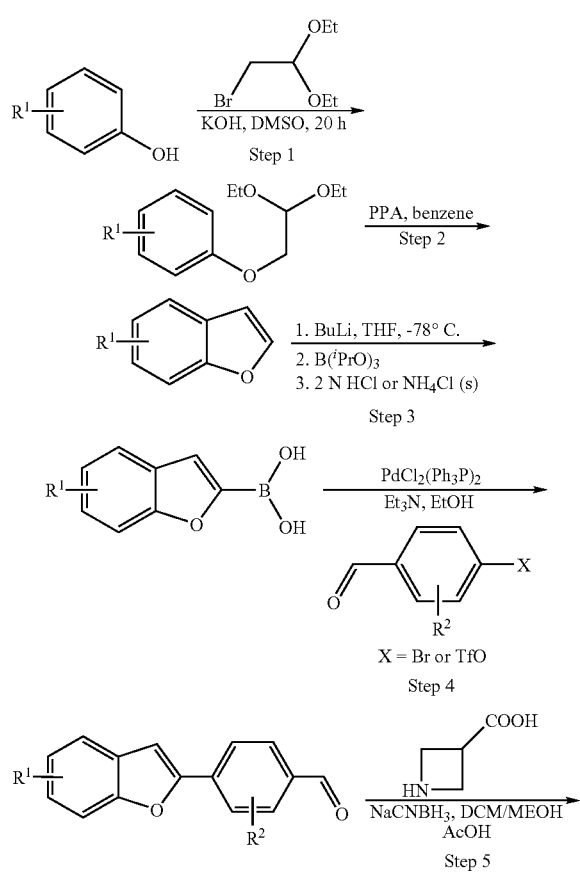

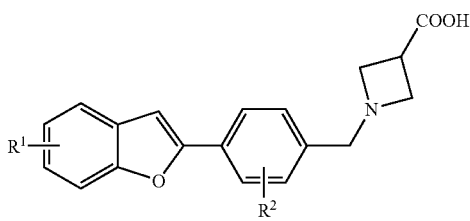

Scheme 2

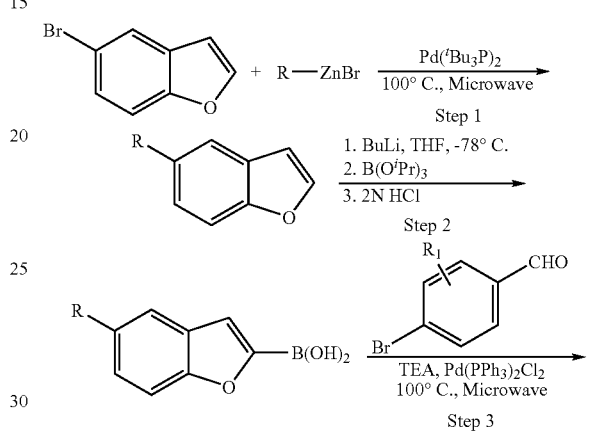

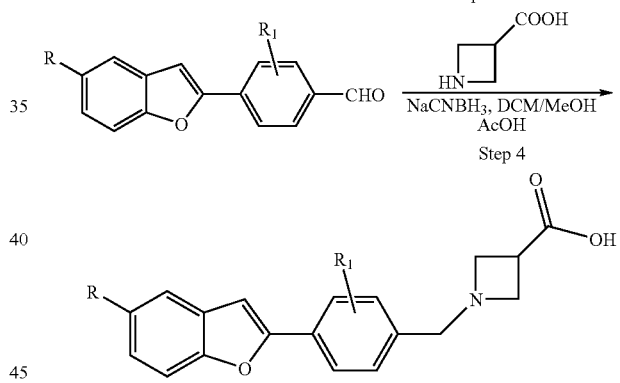

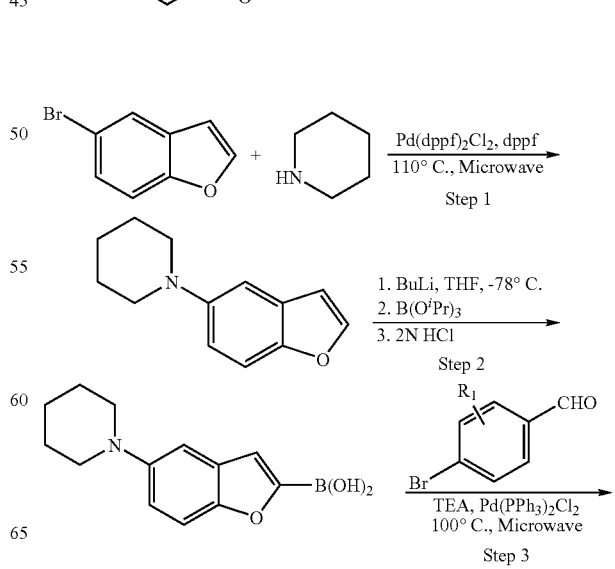

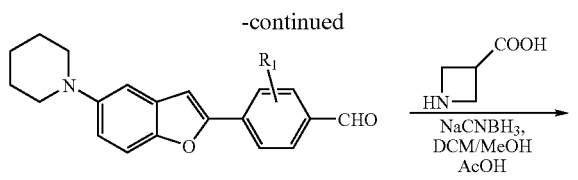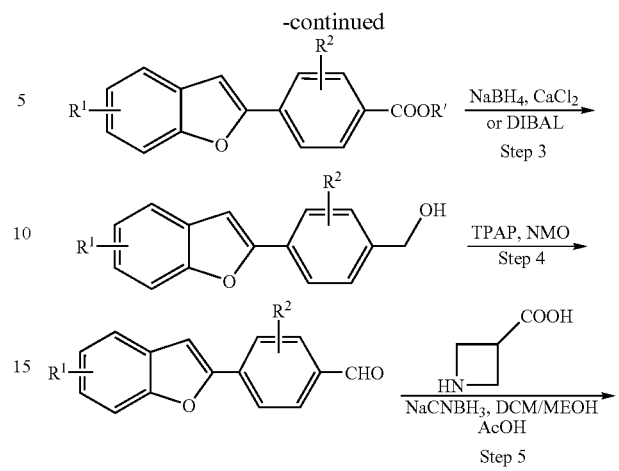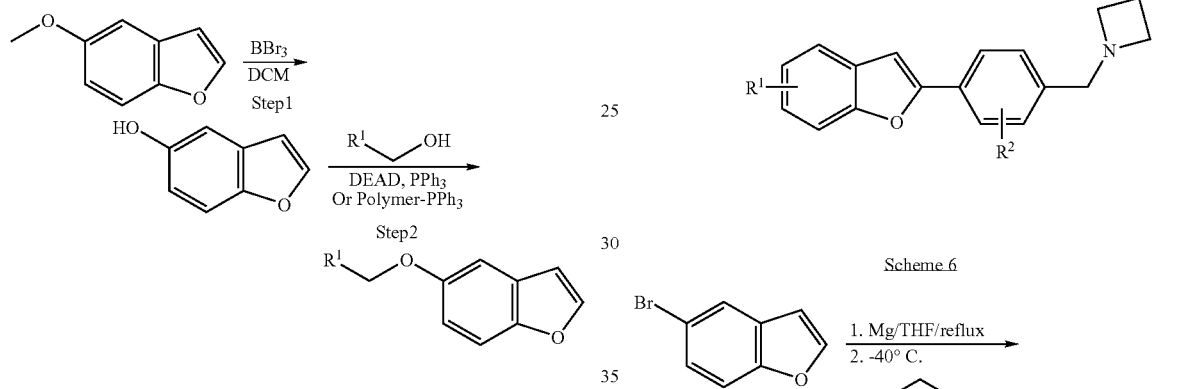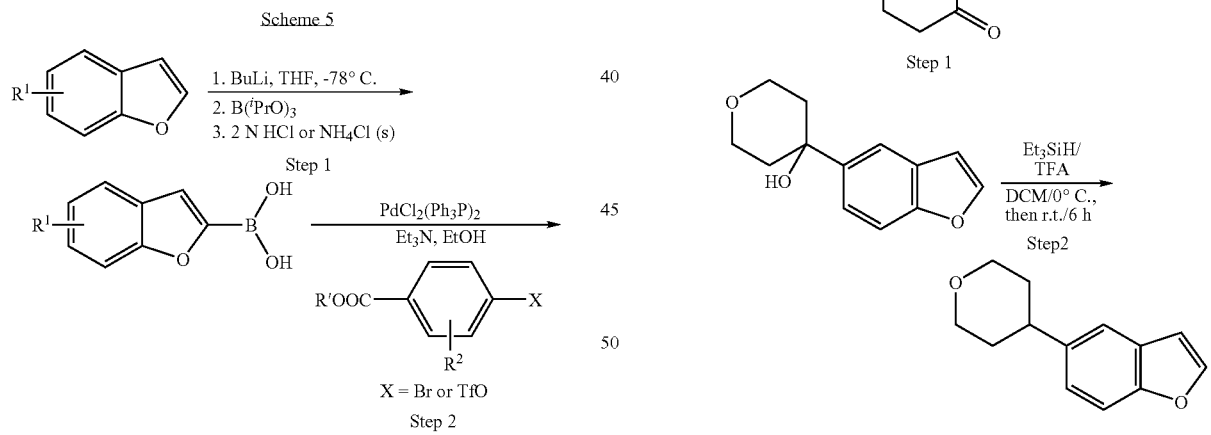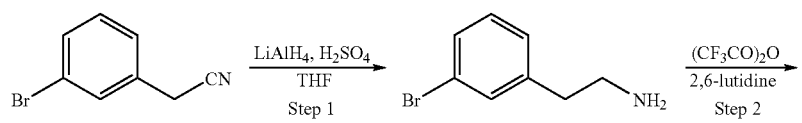

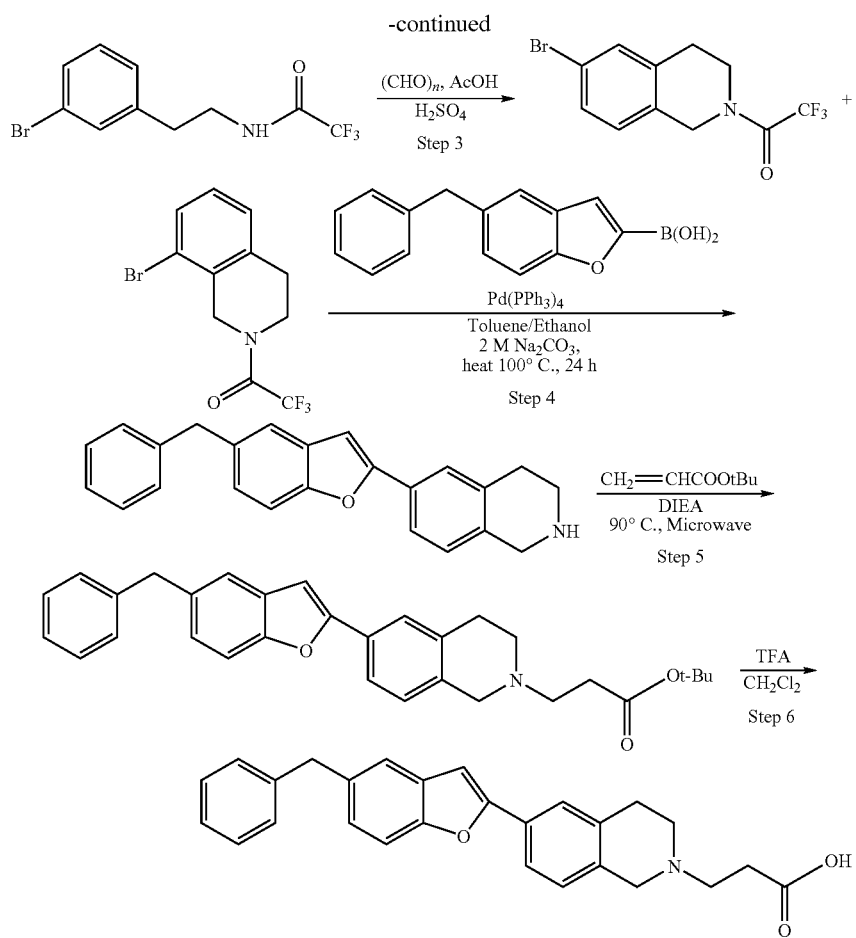
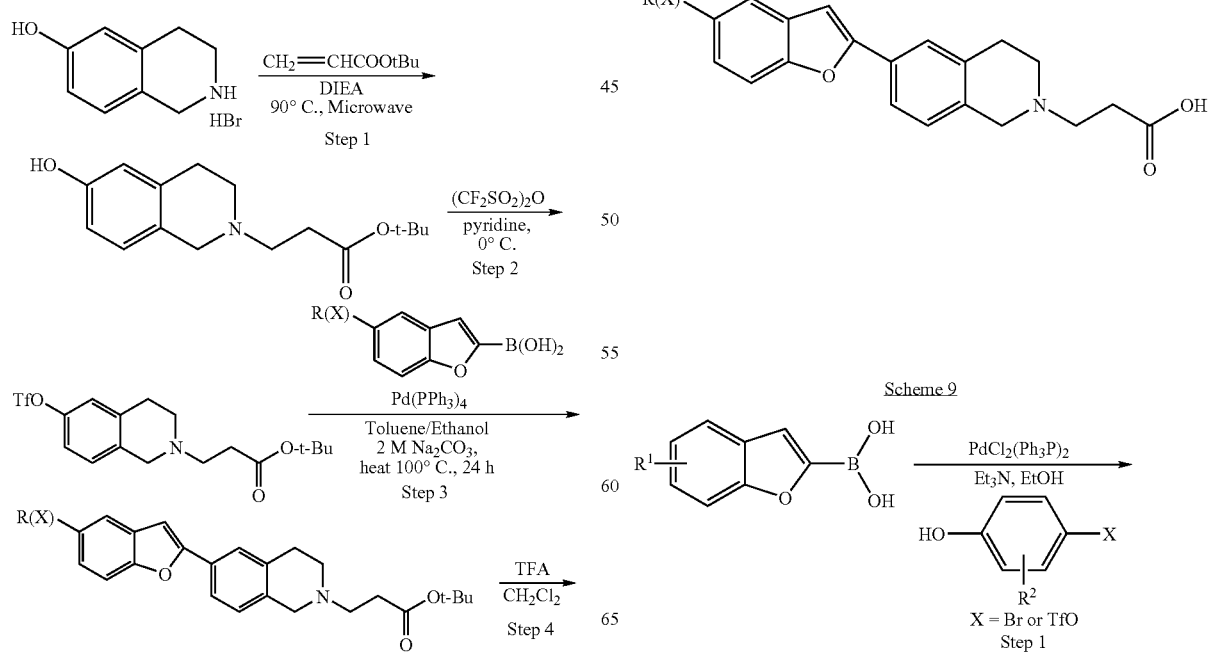

-continued

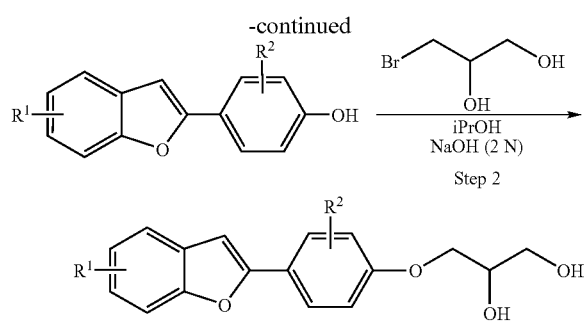

EXAMPLES

Compounds were prepared using the general procedures as described below:

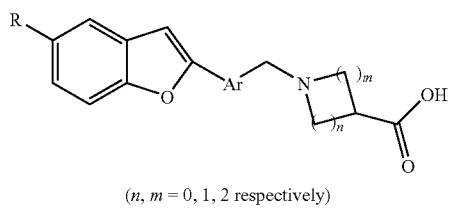

(n, m = 0, 1, 2 respectively)

A: General Procedure for C—C Bond Coupling with Rieke Reagents 5-bromobenzofuran (1.0 mmol) was dissolved in a THF solution of Rieke reagent (0.5M, 2.9 mmol) in a microwave reaction tube. Pd(PtBu$_3$)$_2$ (0.05 mmol) was added to this solution. The mixture was purged with N$_2$ gas for 3-5 min and heated at 100° C. for 30 min under microwave irradiation (Personal Chemistry Emrys™ Optimizer microwave reactor). Upon completion of the reaction, the reaction mixture was diluted with ethyl acetate, washed with 1N HCl aqueous solution, brine, filtered through Celite. The filtrate was dried over Na$_2$SO$_4$ and concentrated. The residue was purified by silica gel column chromatography (ISCO system) to give a pure product.

B: General Procedure for N—C Bond Coupling Reaction 5-bromobenzofuran (1.0 mmol), piperidine (1.2 mmol), Pd(dppf)Cl$_2$ (0.03 mmol), dppf (0.045 mmol) and sodium tert-butoxide (1.5 mmol) was mixed in toluene (2 mL). The mixture was purged with N$_2$ gas for 3-5 min and heated at 120° C. for 30 min under microwave irradiation (Personal Chemistry Emrys™ Optimizer microwave reactor). Upon completion of the reaction, the reaction mixture was directly loaded on silica gel column and purified on ISCO system (5% EtOAc in hexanes) to give a pure product.

C: General Preparative Procedure for Formation of Benzofuran Boronic Acids

A solution of n-BuLi (1.2 mmol, 2.5M solution in hexanes) was added dropwise to a solution of benzofuran compounds (1.0 mmol) in anhydrous THF (20 mL) at −78° C. The resulting mixture was stirred at −78° C. for 20 min, and treated with B($^i$PrO)$_3$ (1.5 mmol). The reaction mixture was allowed to warm up slowly to room temperature and stirred for 1 h. The reaction was cooled in ice-bath and quenched with 2N HCl or saturate NH$_4$Cl and extracted with Et$_2$O. The combined organic extracts were washed with brine, dried and concentrated under reduced pressure to yield a desired benzofuran boronic acid without further purification for next step.

D: General Procedure of Coupling Boronic Acids with Aryl Halides

A mixture of benzofuran boronic acid (1.1 mmol), aryl halide (1.0 mmol), triethylamine (20 mmol) and bis(triphenylphosphine)palladium(II) chloride (0.05 mmol) in ethanol (30 mL) was irradiated in a microwave instrument at 100° C. for 20 min. The reaction mixture was cooled, and the solvent was removed. The residue was treated with water and extracted with ethyl acetate. The organic layer was dried and concentrated in vacuo (the aqueous work-up is optional). Purification by silica gel chromatography gave the desired product.

E: General Procedure of Reductive Amination

A mixture of aldehyde (1.0 mmol), acetic acid (1.5 mmol) and azetidine-3-carboxylic acid or piperidine-4-carboxylic acid (1.2-1.5 mmol) in DCM/MeOH (1:1, 10 mL) was stirred at room temperature for 1 h. Sodium cyanoborohydride (0.5 mmol) was added and the reaction mixture was stirred for 2-3 h at room temperature. After concentration of solvent under reduced pressure, the resulting residue was dissolved in DMSO, filtered and purified by reverse phase preparative HPLC (Phenomenex reverse phase Luna 5µ Cl8(2) column, 60×21.2 mm ID, mobile phase: A=0.05% TFA in water; B=0.05% TFA in acetonitrile. The flow rate was 10-12 mL/min) to yield the desired final product with puritiy greater than 95%. All final products were obtained as the TFA salts except for Compound 59. Alternatively, the crude mixture of reductive amination can be purified by trituration with MeOH and water.

Compound 1

1-(4-(5-Phenylbenzofuran-2-yl)benzyl)azetidine-3-carboxylic acid 1-(2,2-Diethoxyethoxy)-4-phenylbenzene (Step 1 in Scheme 1)

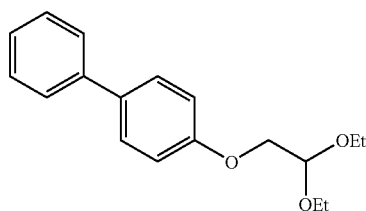

A mixture of 4-phenylphenol (5 g, 29.4 mmol), bromoacetaldehyde diethyl acetal (4.56 mL, 29.4 mmol) and KOH (1.94 g, 29.4 mmol) in DMSO (15 mL) was stirred at reflux for 6 h. The reaction mixture was allowed to cool down to room temperature and poured over ice containing 0.60 g of KOH and diluted to 100 mL with water. The solution was extracted with Et$_2$O (20 mL×3); the combined extracts were washed with 1N NaOH solution, water and brine, dried, and concentrated under reduced pressure to yield 7.97 g (94%) of a yellow oil that was used without further purification: $^1$H NMR (400 MHz, CDCl$_3$) δ 7.56-7.50 (m, 4H), 7.41 (t, 2H), 7.30 (t, 1H), 7.00 (dt, 2H), 4.86 (t, 1H), 4.05 (d, 2H), 3.82-3.74 (m, 2H), 3.69-3.62 (m, 2H).

5-Phenylbenzofuran (Step 2 in Scheme 1)

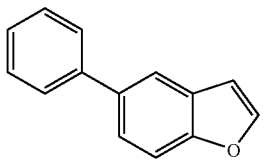

A mixture of 1-(2,2-diethoxyethoxy)-4-phenylbenzene (3.52 g, 12.3 mmol) and polyphosphoric acid (2.95 g, 29.4 mmol) in benzene (60 mL) was stirred at reflux for 2 h. The reaction mixture was cooled to room temperature, decanted from the PPA and filtered through a plug of silica gel, which was washed with hexanes. The filtrate and the wash were combined and concentrated under reduced pressure to yield 2.00 g of the crude benzofuran: $^1$H NMR (400 MHz, CD$_3$OD) δ 7.79 (dd, 1H), 7.66 (d, 1H), 7.63-7.60 (m, 2H), 7.58-7.51 (m, 2H), 7.45 (t, 2H), 7.36-7.33 (m, 1H), 6.82 (dd, 1H).

5-Phenylbenzofuran-2-yl-2-boronic acid (Step 3 in Scheme 1)

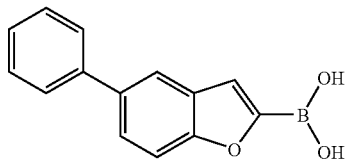

A solution of n-BuLi (2.0 mL, 2.5M solution in hexanes) was added dropwise to a solution of 5-phenylbenzofuran (816 mg, 4.21 mmol) in anhydrous THF (20 mL) at −78° C. The resulting mixture was stirred at −78° C. for 20 min, and treated with B($^i$PrO)$_3$ (1.46 mL, 6.31 mmol). The reaction mixture was allowed to warm up slowly to room temperature and stirred for 1 h. The reaction was quenched with 2N HCl and extracted with Et$_2$O. The combined extracts were washed with brine, dried and concentrated under reduced pressure to yield 1.2 g of crude boronic acid, that was used without further purification: $^1$H NMR (400 MHz, CD$_3$OD) δ 7.83 (dd, 1H), 7.64-7.55 (m, 4H), 7.48-7.42 (m, 3H), 7.38-7.32 (m 1H).

4-(5-Phenylbenzofuran-2-yl)benzaldehyde (Step 4 in Scheme 1)

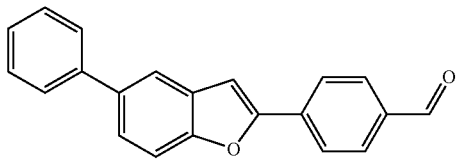

A solution of 5-phenylbenzofuran-2-yl-2-boronic acid (527 mg, 2.22 mmol), 4-bromobenzaldehyde (315 mg, 1.70 mmol), palladiumdichlorobis(triphenylphosphine) (60 mg, 0.085 mmol) and triethylamine (4.74 mL, 34 mmol) in EtOH was irradiated in the microwave at 100° C. for 1200 s. The precipitated that formed was filtered and rinsed with ethanol to yield 217 mg of desired benzaldehyde: $^1$H NMR (400 MHz, CD$_3$OD) δ 10.06 (s, 1H), 8.05 (d, 2H), 7.98 (d, 2H), 7.82 (br s, 1H), 7.65-7.52 (m, 4H), 7.48 (dd, 2H), 7.37 (t, 1H). MS (ESI) m/z: Calculated: 298.10; Observed: 299.1 (M$^+$+1).

1-(4-(5-Phenylbenzofuran-2-yl)benzyl)azetidine-3-carboxylic acid (Step 5 in Scheme 1)

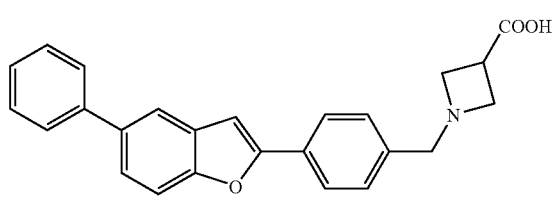

A mixture of 4-(5-phenylbenzofuran-2-yl)benzaldehyde (49 mg, 0.14 mmol) and azetidine-3-carboxylic acid (30 mg, 0.28 mmol) in MeOH (1 mL) was stirred at room temperature for 1 h. Sodium cyanoborohydride (60 mg, 0.28 mmol) was added in two portions and the reaction mixture was stirred for 16 h. Concentration of the solvent under reduced pressure yielded a yellow solid that was dissolved in DMSO (3 mL) and filtered to give a yellow solution that was purified by HPLC to yield 3 mg of desired product: $^1$H NMR (400 MHz, CD$_3$OD) δ 8.03 (d, 2H), 7.84 (br s, 1H), 7.66-7.58 (m, 6H), 7.45 (t, 2H), 7.36-7.32 (m, 2H), 4.47 (s, 2H), 4.40-4.32 (m, 4H), 3.72 (m, 1H). MS (ESI) m/z: Calculated: 383.15; Observed: 383.9 (M$^+$+1).

Compound 2

1-((4-(5-Butylbenzofuran-2-yl)phenyl)methyl)azetidine-3-carboxylic acid

1-(2,2-Diethoxyethoxy)-4-butylbenzene

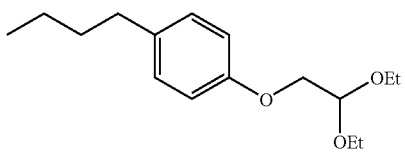

The title compound was prepared as Example Compound 1 (step 1 in Scheme 1) in the general method described above (90% yield): $^1$H NMR (400 MHz, CDCl$_3$) δ 7.07 (d, J=8.8, 2H), 6.83 (d, J=8.8, 2H), 4.83 (t, J=5.1, 1H), 3.98 (d, J=5.1, 2H), 3.80-3.72 (m, 2H), 3.67-3.59 (m, 2H), 2.54 (t, J=7.7, 2H), 1.59-1.51 (m, 2H), 1.36-1.30 (m, 2H), 1.24 (t, J=7.0, 6H), 0.91 (t, J=7.3, 3H).

5-Butylbenzofuran

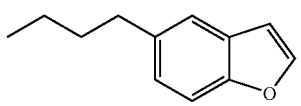

The title compound was prepared as Example Compound 1 (step 2 in Scheme 1) in the general method described above (91% yield): $^1$H NMR (400 MHz, CDCl$_3$) δ 7.58 (d, J=2.2, 1H), 7.41-7.36 (m, 2H), 7.11 (dd, J=8.5, 1.8, 1H), 6.70 (dd, J=2.2, 1.1, 1H), 2.70 (t, J=7.7, 2H), 1.67-1.60 (m, 2H), 1.42-1.32 (m, 2H), 0.93 (t, J=7.3, 3H).

5-Butylbenzofuran-2-yl-2-boronic acid

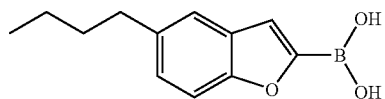

The title compound was prepared as Example Compound 1 (step 3 in Scheme 1) in the general method described above (67% yield): $^1$H NMR (400 MHz, CDCl$_3$) δ 7.43-7.31 (m, 2H), 7.22-7.14 (m, 2H), 2.70 (t, J=7.7, 2H), 1.67-1.59 (m, 2H), 1.41-1.32 (m, 2H), 0.93 (t, J=7.3, 3H).

4-(5-Butylbenzofuran-2-yl)benzaldehyde

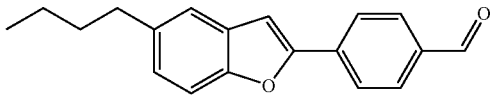

The title compound was prepared as Example Compound 1 (step 4 in Scheme 1) in the general method described above (72% yield): $^1$H NMR (400 MHz, CDCl$_3$) δ 10.03 (s, 1H), 8.00 (d, J=8.4, 2H), 7.94 (d, J=8.4, 2H), 7.45-7.41 (m, 2H), 7.17-7.15 (m, 2H), 2.71 (t, J=7.7, 2H), 1.68-1.61 (m, 2H), 1.41-1.33 (m, 2H), 0.94 (t, J=7.3, 3H).

1-((4-(5-Butylbenzofuran-2-yl)phenyl)methyl)azetidine-3-carboxylic acid

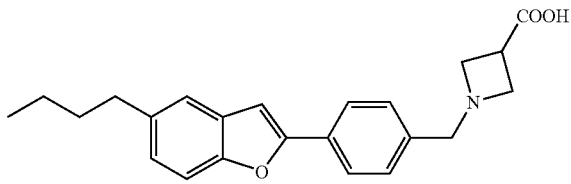

The title compound was prepared as Example Compound 1 (step 5 in Scheme 1) in the general method described above (42% yield): $^1$H NMR (400 MHz, CD$_3$OD) δ 7.98 (d, J=8.4, 2H), 7.55 (d, J=8.4, 2H), 7.43-7.41 (m, 2H), 7.23 (s, 1H), 7.15 (d, J=8.8, 1H), 4.40 (s, 2H), 4.25-4.23 (m, 4H), 3.52-3.46 (m, 1H), 2.71 (t, J=7.7, 2H), 1.67-1.61 (m, 2H), 1.41-1.33 (m, 2H), 0.95 (t, J=7.3, 3H). MS (ESI) m/z: Calculated: 363.18; Observed: 364.0 (M$^+$+1).

Compound 3

1-(4-(5-Butoxybenzofuran-2-yl)phenyl)methyl)azetidine-3-carboxylic acid

1-(2,2-Diethoxyethoxy)-4-butoxybenzene

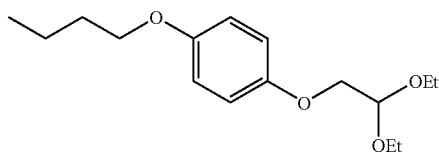

The title compound was prepared as Example Compound 1 (step 1 in Scheme 1) in the general method described above (84% yield): $^1$H NMR (400 MHz, CDCl$_3$) δ 6.86-6.80 (m, 4H), 4.81 (t, J=5.1, 1H), 3.96 (d, J=5.1, 2H), 3.90 (t, J=6.6, 2H), 3.79-3.72 (m, 2H), 3.67-3.59 (m, 2H), 1.77-1.70 (m, 2H), 1.52-1.43 (m, 2H), 1.24 (t, J=7.0, 6H), 0.96 (t, J=7.4, 3H).

5-Butoxybenzofuran

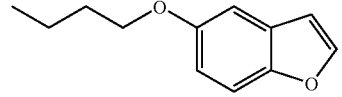

The title compound was prepared as Example Compound 1 (step 2 in Scheme 1) in the general method described above (81% yield): $^1$H NMR (400 MHz, CDCl$_3$) δ 7.58 (d, J=2.2, 1H), 7.38 (d, J=9.2, 1H), 7.05 (d, J=2.5, 1H), 6.90 (dd, J=2.5, 8.8, 1H), 6.69 (br d, J=2.2, 1H), 3.99 (t, J=6.6, 2H), 1.82-1.75 (m, 2H), 1.56-1.47 (m, 2H), 0.99 (t, J=7.3, 3H).

5-Phenylbenzofuran-2-yl-2-boronic acid (Step 3 in Scheme 1)

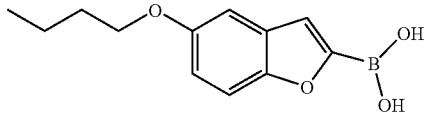

A solution of n-BuLi (2.5 mL, 2.5M solution in hexanes) was added dropwise to a solution of 5-butoxybenzofuran (1.0 g, 5.21 mmol) in anhydrous THF (20 mL) at −78° C. The resulting mixture was stirred at −78° C. for 20 min, and treated with B($^i$PrO)$_3$ (1.80 mL, 7.8 mmol). The reaction mixture was allowed to warm up slowly to room temperature and stirred for 1 h. The reaction was quenched with 2N HCl and extracted with Et$_2$O. The combined extracts were washed with brine, dried and concentrated under reduced pressure to yield 1.2 g of crude boronic acid, that was used without further purification: (98% yield): $^1$H NMR (400 MHz, CDCl$_3$) δ 7.37 (d, 1H), 7.30 (d, 1H), 7.06 (s, 1H), 6.98 (d, 1H), 4.44 (s, 2H), 1.81-1.71 (m, 2H), 1.58-1.50 (m, 2H), 1.00 (t, 3H).

4-(5-Butoxybenzofuran-2-yl)benzaldehyde (Step 4 in Scheme 1)

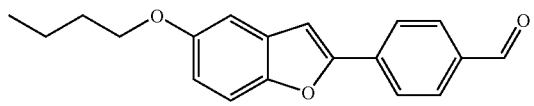

A solution of 5-phenylbenzofuran-2-yl-2-boronic acid (702 mg, 3.0 mmol), 4-bromobenzaldehyde (427 mg, 2.30 mmol), palladiumdichlorobis(triphenylphosphine) (80 mg, 0.11 mmol) and triethylamine (6.5 mL, 45 mmol) in EtOH (2 mL) was irradiated in the microwave at 100° C. for 1200 s. The precipitate that formed was filtered and rinsed with ethanol to yield 620 mg of crude product, which upon column chromatography afforded 375 mg of the desired compound (43%): $^1$H NMR (400 MHz, CDCl$_3$) δ 10.03 (s, 1H), 8.05 (d, 2H), 7.98 (d, 2H), 7.82 (d, 1H), 7.18 (d, 1H), 7.16 (d, 1H), 6.94 (s, 1H), 4.44 (s, 2H), 1.81-1.71 (m, 2H), 1.58-1.50 (m, 2H), 1.00 (t, 3H). MS (ESI) m/z: Calculated: 294.34; Observed: 295.2 (M$^+$+1).

1-(4-(5-Butoxybenzofuran-2-yl)phenyl)methyl)azetidine-3-carboxylic acid (Step 5 in Scheme 1)

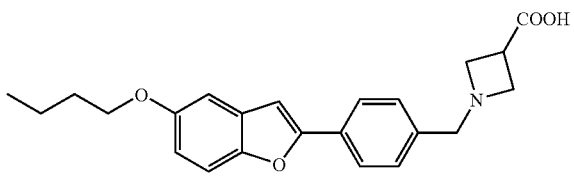

A mixture of 4-(5-butoxybenzofuran-2-yl)benzaldehyde (70 mg, 0.30 mmol), azetidine-3-carboxylic acid (46 mg, 0.45 mmol) and acetic acid (0.50 mmol) in MeOH-DCM (3:1; 2 mL) was stirred at room temperature for 1 h. Sodium triacetoxyborohydride (211 mg, 1.00 mmol) was added and the reaction mixture was stirred for 16 h. Concentration of the solvent under reduced pressure yielded a yellow solid that was dissolved in DMSO (3 mL) and filtered to give a yellow solution that was purified by HPLC to afford 6 mg of desired product (5% yield): $^1$H NMR (400 MHz, CD$_3$OD) δ 7.97 (d, 2H), 7.55 (d, 2H), 7.40 (d, 1H), 7.21 (s, 1H), 7.10 (d, 1H), 6.92-6.89 (dd, 1H), 4.44 (s, 2H), 4.37 (q, 4H), 4.00 (t, 2H), 3.72-3.64 (m, 1H), 1.81-1.71 (m, 2H), 1.58-1.50 (m, 2H), 1.00 (t, 3H). MS (ESI) m/z: Calculated: 379.45; Observed: 380.3 (M$^+$+1).

Compound 4

1-((4-(5-Benzylbenzofuran-2-yl)phenyl)methyl)azetidine-3-carboxylic acid 1-(4-(2,2-Diethoxyethoxy)benzyl)benzene

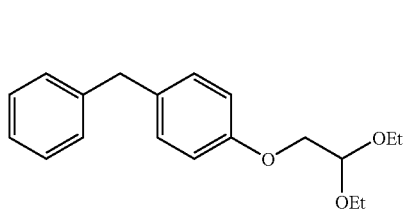

The title compound was prepared as Example Compound 1 (step 1 in Scheme 1) in the general method described above (84% yield): $^1$H NMR (400 MHz, CDCl$_3$) δ 7.30-7.25 (m, 2H), 7.20-7.15 (m, 3H), 7.09 (d, J=8.8, 2H), 6.84 (d, J=8.8, 2H), 4.82 (t, J=5.5, 1H), 3.98 (d, J=5.5, 2H), 3.92 (s, 2H), 3.79-3.72 (m, 2H), 3.66-3.59 (m, 2H), 1.24 (t, 7.1, 3H).

5-Benzylbenzofuran

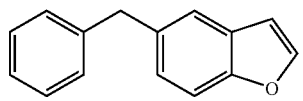

The title compound was prepared as Example Compound 1 (step 2 in Scheme 1) in the general method described above (89% yield): $^1$H NMR (400 MHz, CDCl$_3$) δ 7.58 (d, J=2.2, 1H), 7.42-7.40 (m, 2H), 7.31-7.7.26 (m, 3H), 7.25-7.12 (m, 3H), 6.70 (m, 1H), 4.08 (s, 2H).

5-Benzylbenzofuran-2-yl-2-boronic acid

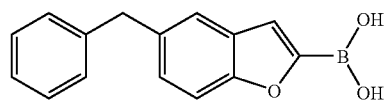

The title compound was prepared as Example Compound 1 (step 3 in Scheme 1) in the general method described above (66% yield): $^1$H NMR (400 MHz, CDCl$_3$) δ 7.44 (m, 1H), 7.42 (d, J=8.4, 1H), 7.32-7.26 (m, 4H), 7.25-7.19 (m, 3H), 4.81 (s, 2H), 4.08 (s, 2H).

4-(5-Benzylbenzofuran-2-yl)benzaldehyde

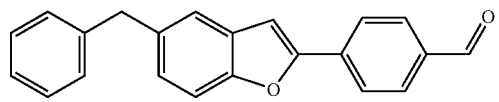

The title compound was prepared as Example Compound 1 (step 4 in Scheme 1) in the general method described above (76% yield): $^1$H NMR (400 MHz, CDCl$_3$) δ 10.03 (s, 1H), 7.99 (d, J=8.4, 2H), 7.94 (d, J=8.4, 2H), 7.46-7.41 (m, 2H), 7.32-7.17 (m, 6H), 7.13 (br s, 1H), 4.08 (s, 2H).

1-((4-(5-Benzylbenzofuran-2-yl)phenyl)methyl)azetidine-3-carboxylic acid

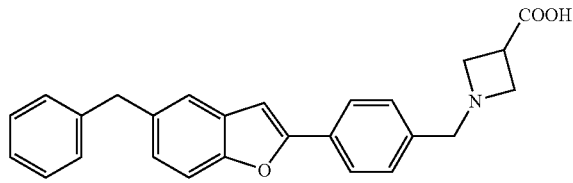

The title compound was prepared as Example Compound 1 (step 5 in Scheme 1) in the general method described above (62% yield): ¹H NMR (400 MHz, CD₃OD) δ 7.98 (d, J=8.4, 2H), 7.55 (d, J=8.4, 2H), 7.45-7.42 (m, 2H), 7.28-7.15 (m, 7H), 4.44 (s, 2H), 4.37-4.22 (m, 4H), 4.06 (s, 2H), 3.72-3.64 (m, 1H). MS (ESI) m/z: Calculated: 397.17; Observed: 398.0 (M⁺+1).

Compound 5

1-((4-(7-Benzylbenzofuran-2-yl)phenyl)methyl)azetidine-3-carboxylic acid

1-(2-(2,2-Diethoxyethoxy)benzyl)benzene

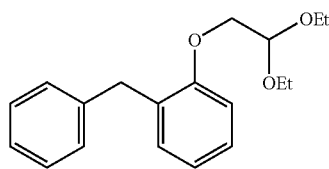

The title compound was prepared as Example Compound 1 (step 1 in Scheme 1) in the general method described above (99% yield): ¹H NMR (400 MHz, CDCl₃) δ 7.27-7.21 (m, 4H), 7.19-7.15 (m, 2H), 7.08 (br d, J=5.9, 1H), 6.90-6.83 (m, 2H), 4.78 (t, J=5.1, 1H), 4.00-3.98 (m, 4H), 3.76-3.69 (m, 2H), 3.63-3.56 (m, 2H), 1.22 (t, J=7.0, 6H).

7-Benzylbenzofuran

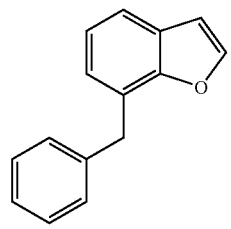

The title compound was prepared as Example Compound 1 (step 2 in Scheme 1) in the general method described above (84% yield): ¹H NMR (400 MHz, CDCl₃) δ 7.62 (d, J=2.2, 1H), 7.45 (d, J=7.7, 1H), 7.36 (s, 1H), 7.29-7.26 (m, 3), 7.25-7.13(m, 2), 7.05 (d, J=7.4, 1H), 6.76 (d, J=2.2, 1H), 4.27 (s, 2H).

7-Benzylbenzofuran-2-yl-2-boronic acid

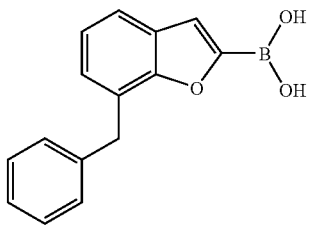

The title compound was prepared as Example Compound 1 (step 3 in Scheme 1) in the general method described above (67% yield): ¹H NMR (400 MHz, CDCl₃) δ 7.50 (dd, J=7.7, 1H), 7.36 (s, 1H), 7.29-7.25 (m, 4H), 7.18-7.09 (m, 3H), 4.29 (s, 2H).

4-(7-Benzylbenzofuran-2-yl)benzaldehyde

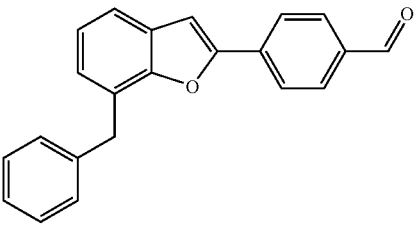

The title compound was prepared as Example Compound 1 (step 4 in Scheme 1) in the general method described above (72% yield): ¹H NMR (400 MHz, CDCl₃) δ 10.04 (s, 1H), 8.00-7.94 (m, 4H), 7.50 (d, J=9.9, 1H), 7.47-7.27 (m, 4H), 7.24-7.17 (m, 3H), 7.11 (d, J=7.3, 1H), 4.33 (s, 2H).

1-((4-(7-Benzylbenzofuran-2-yl)phenyl)methyl)azetidine-3-carboxylic acid

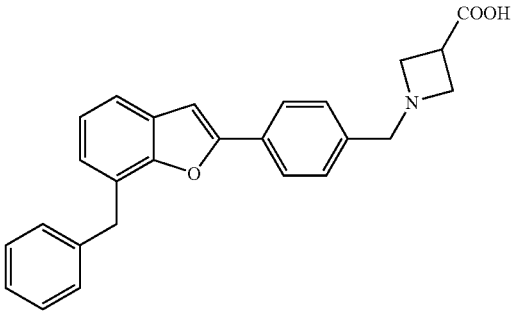

The title compound was prepared as Example Compound 1 (step 5 in Scheme 1) in the general method described above (81% yield): ¹H NMR (400 MHz, CD₃OD) δ 7.97 (d, J=8.0, 2H), 7.56 (d, J=8.0, 2H), 7.48 (d, J=7.7, 1H), 7.34-7.24 (m, 5H), 7.19-7.10 (m, 3H), 4.44 (s, 2H), 4.32-4.25(m, 6H), 3.66-3.56 (m, 1H). MS (ESI) m/z: Calculated: 397.17; Observed: 397.9 (M⁺+1).

Compound 6

1-(4-(5-cyclohexylbenzofuran-2-yl)benzyl)azetidine-3-carboxylic acid

5-cyclohexylbenzofuran (Step 1 in Scheme 2)

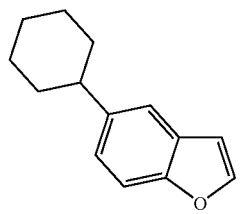

5-bromobenzofuran (500 mg, 2.55 mmol) was dissolved in a THF solution of cyclohexyl zinc(II) bromide (0.5M, 15 mL, 7.40 mmol) in a microwave reaction tube. Pd(P$^t$Bu$_3$)$_2$ (65 mg, 0.128 mmol, 0.05 eqv.) was added to this solution. The mixture was purged with N$_2$ gas for 3-5 min and heated at 100° C. for 30 min under microwave irradiation. Upon completion of the reaction, the reaction mixture was diluted with ethyl acetate, washed with 1N HCl aqueous solution, brine, filtered through Celite. The filtrate was dried over Na$_2$SO$_4$ and concentrated. The residue was purified by silica gel column chromatography (ISCO system, 5% EtOAc in hexanes) to give 0.217 g desired product (43% yield): $^1$H NMR (400 MHz, CDCl$_3$) δ 7.57 (d, 1H), 7.41 (d, 2H), 7.15 (d, 1H), 6.72 (d, 1H), 2.58 (m, 1H), 1.92-1.74 (m, 4H), 1.51-1.35 (m, 4H), 1.31-1.25 (m, 2H).

5-cyclohexylbenzofuran-2-ylboronic acid (Step 2 in Scheme 2)

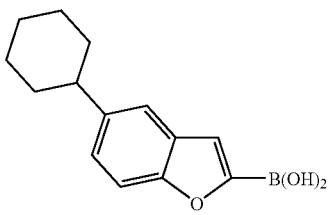

A solution of n-BuLi (360 μL, 0.9 mmol, 2.5M solution in hexanes) was added dropwise to a solution of 5-cyclohexylbenzofuran (150 mg, 0.75 mmol) in anhydrous THF (5 mL) at −78° C. The resulting mixture was stirred at −78° C. for 40 min, and treated with B($^i$PrO)$_3$ (260 μL, 1.13 mmol). The reaction mixture was allowed to warm up slowly to room temperature and stirred for 1 h. TLC indicated the completion of reaction. The reaction was cooled in ice-bath and quenched with 2N HCl (3 mL) and extracted with Et$_2$O. The combined organic extracts were washed with brine, dried and concentrated under reduced pressure to yield a desired boronic acid (0.156 g, 85% yield) without further purification for next step. $^1$H NMR (400 MHz, CDCl$_3$) δ 7.46 (s, 1H), 7.43 (d, 1H), 7.32 (s, 1H), 7.25 (d, 1H), 2.62 (m, 1H), 1.93-1.85 (m, 4H), 1.78-1.75 (m, 4H), 1.34-1.22 (m, 2H).

4-(5-cyclohexylbenzofuran-2-yl)benzaldehyde (Step 3 in Scheme 2)

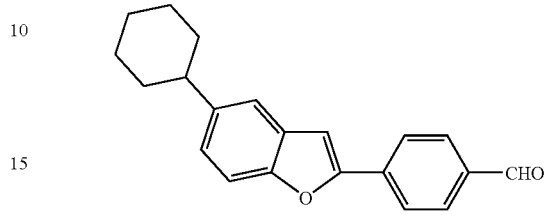

A mixture of 5-cyclohexylbenzofuran-2-ylboronic acid (75 mg, 0.37 mmol), 4-bromobenzaldehyde (62 mg, 0.34 mmol), triethylamine (1.1 mL, 7.5 mmol) and bis(triphenylphosphine)palladium(II)chloride (13 mg, 0.05 mmol) in ethanol (11 mL) was irradiated in a microwave instrument at 100° C. for 20 min. The reaction mixture was cooled, and the solvent was removed. The residue was purification by silica gel chromatography on ISCO system gave the title compound (52 mg, 46% yield): >95% purity by LCMS, ESI-MS: 305.2 M+H⁺). $^1$H NMR (400 MHz, CDCl$_3$) δ 10.03 (s, 1H), 8.00 (d, 2H), 7.95 (d, 2H), 7.46 (d, 2H), 7.19 (d, 1H), 7.16 (s, 1H), 2.63-2.58 (m, 1H), 1.94-1.76 (m, 4H), 1.53-1.42 (m, 4H), 1.38-1.25 (m, 2H). MS (ESI) m/z: Calculated: 304.38; Observed: 305.2 (M⁺+1).

1-(4-(5-cyclohexylbenzofuran-2-yl)benzyl)azetidine-3-carboxylic acid (Step 4 of Scheme 2)

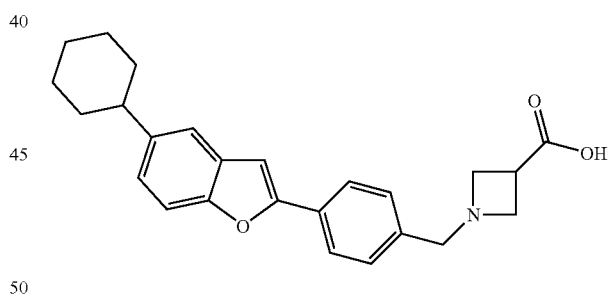

A mixture of 4-(5-cyclohexylbenzofuran-2-yl)benzaldehyde (30 mg, 0.1 mmol), acetic acid (9 μL, 0.15 mmol) and azetidine-3-carboxylic acid (15 mg, 0.15 mmol) in DCM/MeOH (1:1, 2 mL) was stirred at room temperature for 1 h. Sodium cyanoborohydride (3.1 mg, 0.05 mmol) was added and the reaction mixture was stirred for 3 h at room temperature. After concentration of solvent under reduced pressure, the resulting residue was dissolved in hot MeOH and filtered. The filtrate and the white solid, which was redisolved in hot DMSO, were both purified by reverse phase preparative HPLC (Phenomenex reverse phase Luna 5μ C18(2) column, 60×21.2 mm ID) to yield the desired final product (16 mg, 42% yield) as a white powder: >95% purity by LCMS, ESI-MS: 459.1 (M+H)⁺, $^1$H NMR (400 MHz, CD$_3$OD) δ 7.95 (d, 2H), 7.56 (d, 2H), 7.45 (d, 1H), 7.42 (d, 1H), 7.24 (s, 1H), 7.19

(dd, 1H), 4.45 (s, 2H), 4.34 (dd, 4H), 3.69 (m, 1H), 2.64-2.57 (d, 1H), 1.89 (t, 4H), 1.58-1.40 (m, 4H), 1.38-1.26 (m, 2H).

Compound 7

1-(4-(5-cyclohexylbenzofuran-2-yl)benzyl)piperidine-4-carboxylic acid

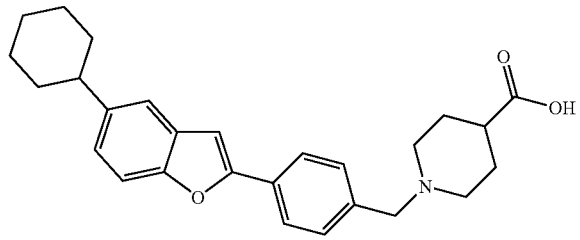

A mixture of 4-(5-cyclohexylbenzofuran-2-yl)benzaldehyde (22 mg, 0.07 mmol), acetic acid (7 μL, 0.11 mmol) and piperidine-4-carboxylic acid (14 mg, 0.11 mmol) in DCM/MeOH (1:1, 1.6 mL) was stirred at room temperature for 1 h. Sodium cyanoborohydride (2.3 mg, 0.05 mmol) was added and the reaction mixture was stirred for 4 h at room temperature. After concentration of solvent under reduced pressure, the resulting residue was dissolved in DMSO, filtered and purified by reverse phase preparative HPLC (Phenomenex reverse phase Luna 5μ C18(2) column, 60×21.2 mm ID) to yield the desired final product (15.4 mg, 51%): >95% purity by LCMS, ESI-MS: 418.1 (M+H)$^+$, $^1$H NMR (400 MHz, CD$_3$OD) δ 8.00 (d, J=8.0 Hz, 2H), 7.59 (d, J=8.0 Hz, 2H), 7.45 (d, J=1.6Hz, 1H), 7.43 (d, J=8.4 Hz, 1H), 7.26 (s, 1H), 7.21 (dd, J=8.4 Hz, J=1.6 Hz), 4.35 (s, 2H), 3.57(d, J=11.6 Hz, 2H), 3.07 (t, J=12 Hz, 2H), 2.64-2.53 (m, 2H), 2.24 (d, 2H), 1.19-1.86 (m, 4H), 1.79 (t, 2H), 1.58-1.42(m, 4H), 1.38-1.26(m, 2H).

Compound 8

1-((4-(5-Butylbenzofuran-2-yl)phenyl)methyl)piperidine-4-carboxylic acid

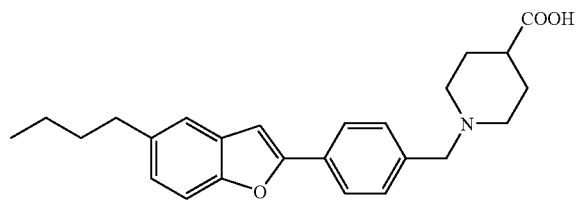

The title compound was prepared as Example Compound 1 (step 5 in Scheme 1) in the general method described above except using piperidine-4-carboxylic acid (57% yield): $^1$H NMR (400 MHz, CD$_3$OD) δ 8.00 (d, J=8.1, 2H), 7.59 (d, J=8.1, 2H), 7.43-7.41 (m, 2H), 7.25 (s, 1H), 7.15 (d, J=8.8, 1H), 4.35 (s, 2H), 3.57 (br d, J=11.7, 2H), 3.07 (br t, J=12.5, 2H), 2.71 (t, J=7.7, 2H), 2.70-2.59 (m, 1H), 2.25 (br d, J=14.6, 2H), 1.93-1.79 (m, 2H), 1.67-1.61 (m, 2H), 1.43-1.33 (m, 2H), 0.95 (t, J=7.3, 3H). MS (ESI) m/z: Calculated: 391.21; Observed: 392.0 (M$^+$+1).

Compound 9

1-((4-(5-Benzylbenzofuran-2-yl)phenyl)methyl)piperidine-4-carboxylic acid

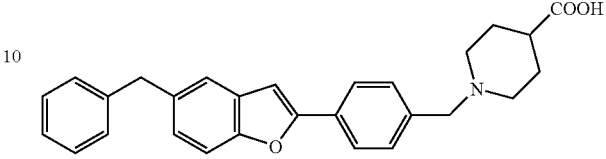

The title compound was prepared as Example Compound 1 (step 5 in Scheme 1) in the general method described above except using piperidine-4-carboxylic acid: $^1$H NMR (400 MHz, CD$_3$OD) δ 7.99 (br d, J=8.0, 2H), 7.58 (br d, J=8.0, 2H), 7.44-7.42 (m, 2H), 7.28-7.16 (m, 7H), 4.34 (br s, 2H), 4.05 (br s, 2H), 3.57 (br d, J=11.7, 2H), 3.05 (br t, J=12.4, 2H), 2.65-2.62 (m, 1H), 2.23 (br d, J=13.5, 2H), 1.89-1.80 (m, 2H). MS (ESI) m/z: Calculated: 425.20; Observed: 426.0 (M$^+$+1).

Compound 10

1-((4-(5-isobutylbenzofuran-2-yl)phenyl)methyl) azetidine-3-carboxylic acid (Scheme 2)

5-isobutylbenzofuran (Step 1 in Scheme 2)

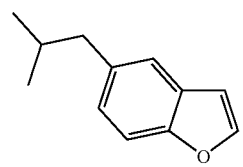

5-bromobenzofuran (500 mg, 2.56 mmol) was dissolved in THF solution of isobutylzinc(II)bromide (0.5M, 15 mL, 7.40 mmol) in a microwave reaction tube. Pd(P$^t$Bu$_3$)$_2$ (65 mg, 0.128 mmol, 0.05 eqv.) was added to this solution. The mixture was purged with N$_2$ gas for 3-5 min and heated at 100° C. for 30 min under microwave irradiation. Upon completion of the reaction, the reaction mixture was diluted with ethyl acetate, washed with 1N HCl aqueous solution, brine, filtered through Celite. The filtrate was dried over Na$_2$SO$_4$ and concentrated. The residue was purified by silica gel column chromatography (ISCO system, 5% EtOAc in hexanes) to give 0.331 g desired product (74% yield): $^1$H NMR (400 MHz, CDCl$_3$) δ 7.59 (s, 1H), 7.35 (d, 1H), 7.07 (d, 1H), 6.70(s, 1H), 2.59 (d, 2H), 1.9 (m, 1H), 0.9 (d, 6H).

5-isobutylbenzofuran-2-ylboronic acid (Step 2 in Scheme 2)

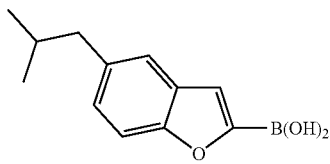

A solution of n-BuLi (912 µL, 2.28 mmol, 2.5M solution in hexanes) was added dropwise to a solution of 5-isobutylbenzofuran (331 mg, 1.9 mmol) in anhydrous THF (12 mL) at −78° C. The resulting mixture was stirred at −78° C. for 40 min, and treated with B($^i$PrO)$_3$ (658 µL, 2.85 mmol). The reaction mixture was allowed to warm up slowly to room temperature and stirred for 1 h. TLC indicated the completion of reaction. The reaction was cooled in ice-bath and quenched with 2N HCl (6 mL) and extracted with Et$_2$O. The combined organic extracts were washed with brine, dried and concentrated under reduced pressure to yield a crude benzofuran boronic acid (0.76 g) without further purification for next step.

4-(5-isobutylbenzofuran-2-yl)benzaldehyde (Step 3 in Scheme 2)

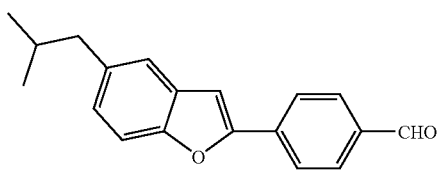

A mixture of 5-isobutylbenzofuran-2-ylboronic acid (70 mg, 0.33 mmol), 4-bromobenzaldehyde (61 mg, 0.33 mmol), triethylamine (1.7 mL, 12.6 mmol) and bis(triphenylphosphine)palladium(II)chloride (12 mg, 0.017 mmol) in ethanol (10 mL) was irradiated in a microwave instrument at 100° C. for 20 min. The reaction mixture was cooled, and the solvent was removed. The residue was treated with water and extracted with ethyl acetate. The organic layer was dried and concentrated in vacuo (the aqueous work-up is optional). Purification by silica gel chromatography on ISCO system gave the title compound (59 mg, 65% yield): >99% purity by LCMS, ESI-MS: 279.2 (M+H)$^+$.

1-((4-(5-isobutylbenzofuran-2-yl)phenyl)methyl) azetidine-3-carboxylic acid (Step 4 in Scheme 2)

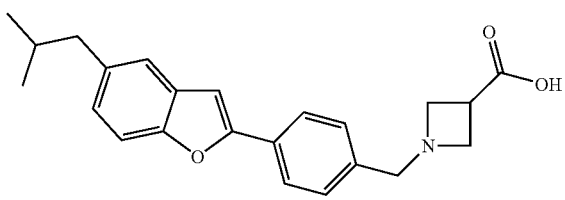

A mixture of 4-(5-isobutylbenzofuran-2-yl)benzaldehyde (30 mg, 0.11 mmol), acetic acid (10 µL, 0.15 mmol) and azetidine-3-carboxylic acid (16 mg, 0.16 mmol) in DCM/MeOH (1:1, 2 mL) was stirred at room temperature for 1 h. Sodium cyanoborohydride (3.4 mg, 0.054 mmol) was added and the reaction mixture was stirred for 3 h at room temperature. After concentration of solvent under reduced pressure, the resulting residue was dissolved in an aliquot of DMSO and purified by reverse phase preparative HPLC (Phenomenex reverse phase Luna 5µ C18(2) column, 60×21.2 mm ID) to yield the desired final product (25.6 mg, 65% yield) as a colorless film: >95% purity by LCMS, ESI-MS: 364.0 (M+H)$^+$, $^1$H NMR (400 MHz, CD$_3$OD) δ 7.99 (d, 2H), 7.55 (d, 2H), 7.42 (d, 1H), 7.39 (s, 1H), 7.24 (s, 1H), 7.12 (dd, 1H), 4.44 (s, 2H), 4.33(d, 4H), 3.68 (m, 1H), 2.57 (d, 2H), 1.90 (m, 1H), 0.92 (d, 6H).

Compound 11

1-((4-(5-phenethylbenzofuran-2-yl)phenyl)methyl) azetidine-3-carboxylic acid

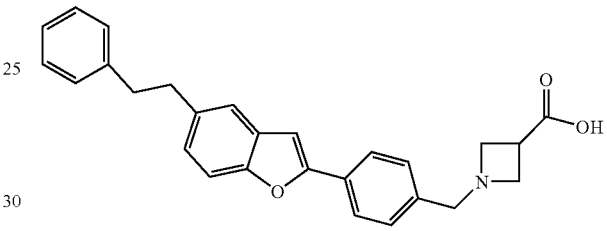

The title compound was prepared in the same manner as Example Compound 6: >95% purity by LCMS, ESI-MS: 411.9 (M+H)$^+$, $^1$H NMR (400 MHz, CD$_3$OD) δ 7.99 (d, 2H), 7.55 (d, 2H), 7.41 (d, 1H), 7.38 (s, 1H), 7.24-7.21 (m, 3H), 7.17-7.14 (m, 4H), 4.44 (s, 2H), 4.34(d, 4H), 3.70 (m, 1H), 3.01-2.90 (m, 4H).

Compound 12

1-(4-(5-pyridin-3-yl)benzofuran-2-yl)benzyl)azetidine-3-carboxylic acid 3-(benzofuran-5-yl)pyridine (Step 1 in Scheme 2 Except Using Suzuki Coulping)

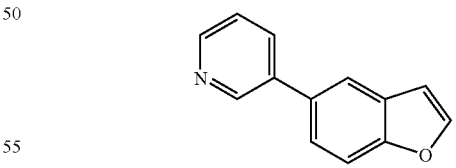

A solution of 5 pyridin-3-ylboronic acid (390 mg, 3.18 mmol), 5-bromobenzofuran (500 mg, 2.54 mmol), palladiumdichlorobis(triphenylphosphine) (111 mg, 0.16 mmol) and triethylamine (8.8 mL, 63.5 mmol) in EtOH was irradiated in the microwave at 100° C. for 1200 s. Removal of the solvents followed by dissolving in CH$_2$Cl$_2$ and filtering gave the residue after concentration of the solvent under reduced pressure. The compound was purified on ISCO to afford 316 mg of the title compound as a light yellow solid: $^1$H NMR (400 MHz, CDCl$_3$) δ 8.89 (s, 1H), 8.60 (d, 1H), 7.90 (d, 1H), 7.80 (s, 1H), 7.69 (s, 1H), 7.55 (d, 1H), 7.50 (d, 1H) 7.38 (dd, 1H), 6.85 (dd, 1H). MS (ESI) m/z: Calculated: 195.07; Observed: 196.30 (M⁺+1).

5-(pyridin-3-yl)benzofuran-2-ylboronic acid (Step 2 in Scheme 2)

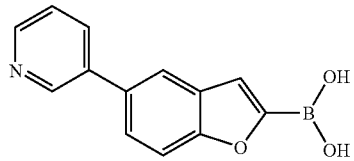

A solution of n-BuLi (0.76 mL, 2.5M solution in hexanes) was added dropwise to a solution of 3-(benzofuran-5-yl)pyridine (310 mg, 1.59 mmol) in anhydrous THF (10 mL) at −78° C. The resulting mixture was stirred at −78° C. for 30 min, and treated with B(ⁱPrO)₃ (0.55 mL, 2.39 mmol). The reaction mixture was allowed to warm up slowly to room temperature and stirred for 1 h. The reaction was quenched with 2N HCl and extracted with Et₂O. The aqueous layer was neutralized with 5N NaOH (PH=6) followed by extraction with THF: ether (1:1) three times. The combined extracts were washed with brine, dried and concentrated under reduced pressure to yield 241 mg of the crude boronic acid, which was used without further purification.

4-(5-(pyridin-3-yl)benzofuran-2-yl)benzaldehyde (Step 3 in Scheme 2)

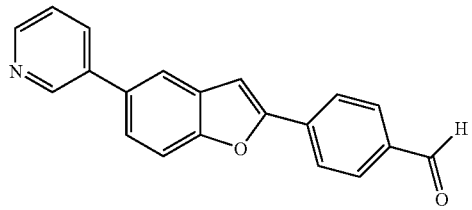

The title compound was prepared as Example Compound 6 in the general method described above (44% yield): ¹H NMR (400 MHz, CDCl₃) δ 10.06 (s, 1H), 8.91 (br s, 1H), 8.61 (br s, 1H), 8.07 (d, 2H), 7.98 (d, 2H), 7.93 (d, 1H), 7.65 (d, 1H), 7.55 (d, 1H), 7.82 (m, 1H), 7.39 (m, 1H), 7.27 (m, 1H). MS (ESI) m/z: Calculated: 299.09; Observed: 300.30 (M⁺+1).

1-(4-(5-(pyridin-3-yl)benzofuran-2-yl)benzyl)azetidine-3-carboxylic acid (Step 4 in Scheme 2)

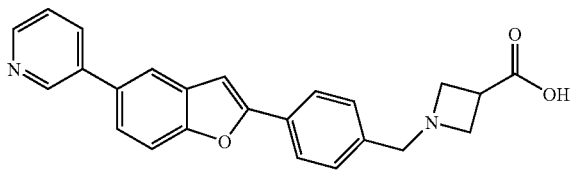

The title compound was prepared as Example Compound 6 in the general method described above (22% yield): ¹H NMR (400 MHz, CD₃OD) δ 9.11 (br s, 1H), 8.70 (m, 2H), 8.06 (m, 3H), 7.98 (m, 1H), 7.74 (m, 2H), 7.60 (d, 2H), 7.44 (s, 1H), 4.47 (s, 2H), 4.40-4.38 (m, 4H), 3.72 (m, 1H). MS (ESI) m/z: Calculated: 384.20; Observed: 385.00 (M⁺+1).

Compound 13

1-(4-(5-isobutylbenzofuran-2-yl)benzyl)piperidine-4-carboxylic acid

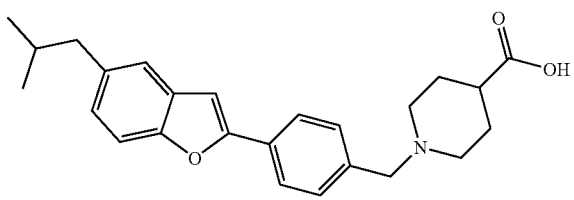

A mixture of 4-(5-isobutylbenzofuran-2-yl)benzaldehyde (22 mg, 0.08 mmol), acetic acid (7 μL, 0.12 mmol) and piperidine-4-carboxylic acid (15 mg, 0.12 mmol) in DCM/MeOH (1:1, 1.4 mL) was stirred at room temperature for 1 h. Sodium cyanoborohydride (2.5 mg, 0.04 mmol) was added and the reaction mixture was stirred for 4 h at room temperature. After concentration of solvent under reduced pressure, the resulting residue was dissolved in an aliquot of DMSO and purified by reverse phase preparative HPLC (Phenomenex reverse phase Luna 5μ C18(2) column, 60×21.2 mm ID) to yield the desired final product (1 6.9 mg, 55%): >95% purity by LCMS, ESI-MS: 392.0 (M+H)⁺, ¹H NMR (400 MHz, CD₃OD) δ 8.01 (d, 2H), 7.59 (d, 2H), 7.43 (d, 1H), 7.39 (s, 1H), 7.26 (s, 1H), 7.13 (dd, 1H), 4.36 (s, 2H), 3.58(m, 2H), 3.10 (m, 2H), 2.65(m, 1H), 2.57 (d, 2H), 1.90 (m, 1H), 0.92 (d, 6H).

Compound 14

1-((4-(5-Benzylbenzofuran-2-yl)2-fluorophenyl)methl)azetidine-3-carboxlic acid 4-(5-Benzylbenzofuran-2-yl)2-fluorobenzaldehyde

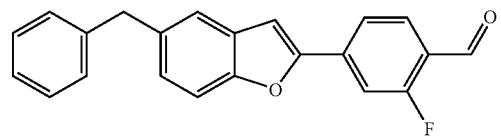

The title compound was prepared as Example Compound 1 (step 4 in Scheme 1) in the general method described above (67% yield): ¹H NMR (400 MHz, CDCl₃) δ 10.35 (s, 1H), 7.92 (dd, J=8.1, 7.0, 2H), 7.69 (d, J=8.5, 1H), 7.63 (d, J=11.4, 1H), 7.46-7.42 (m, 2H), 7.33-7.19 (m, 6H), 7.13 (s, 1H), 4.09 (s, 2H).

1-((4-(5-Benzylbenzofuran-2-yl)2-fluorophenyl)methyl)azetidine-3-carboxylic acid

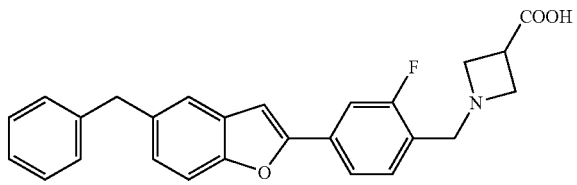

The title compound was prepared as Example Compound 1 (step 5 Scheme 1) in the general method described above (54% yield): $^1$H NMR (400 MHz, CD$_3$OD) δ 7.78 (d, J=8.1, 1H), 7.73 (d, J=9.9, 1H), 7.58 (t, J=7.7, 1H), 7.46-7.44 (m, 2H), 7.29-7.16 (m, 7H), 4.39 (s, 2H), 4.17-4.15(m, 4H), 4.06 (s, 2H), 3.72-3.64 (m, 1H). MS (ESI) m/z: Calculated: 415.16; Observed: 416.0 (M$^+$+1).

Compound 15

1-((4-(5-Benzylbenzofuran-2-yl)-3-fluorophenyl)methyl)azetidine-3-carboxylic acid 4-(5-Benzylbenzofuran-2-yl)-3-fluorobenzaldehyde

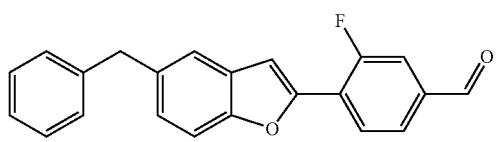

The title compound was prepared as Example Compound 1 (step 4 Scheme 1) in the general method described above (65% yield): $^1$H NMR (400 MHz, CDCl$_3$) δ 10.01 (s, 1H), 8.20 (t, J=7.7, 1H), 7.77 (d, J=8.0, 1H), 7.68 (d, J=11.3, 1H), 7.47-7.45 (m, 2H), 7.37-7.20 (m, 7H), 4.10 (s, 2H).

1-((4-(5-Benzylbenzofuran-2-yl)-3-fluorophenyl)methyl)azetidine-3-carboxylic acid

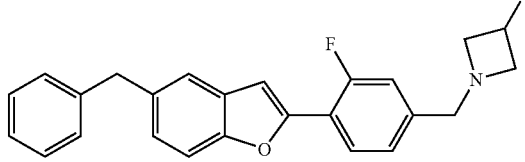

The title compound was prepared as Example Compound 1 (step 5 Scheme 1) in the general method described above (56% yield): $^1$H NMR (400 MHz, CD$_3$OD) δ 8.09 (t, J=7.9, 1H), 7.47-7.45 (m, 2H), 7.40-7.37 (m, 2H), 7.28-7.16 (m, 7H), 4.34 (s, 2H), 4.17-4.15 (m, 4H), 4.07 (s, 2H), 3.53-3.45 (m, 1H). MS (ESI) m/z: Calculated: 415.16; Observed: 415.9 (M$^+$+1).

Compound 16

1-(4-(5-Butoxybenzofuran-2-yl)phenyl)methyl)piperidine-4-carboxylic acid

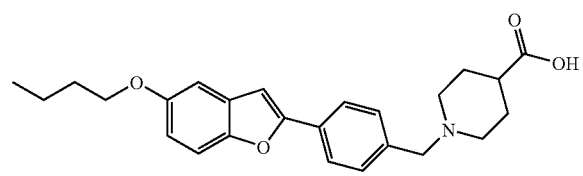

A mixture of 4-(5-butoxybenzofuran-2-yl)benzaldehyde (50 mg, 0.20 mmol), piperidine-4-carboxylic acid (41 mg, 0.31 mmol) and acetic acid (0.50 mmol) in MeOH-DCM (3:1; 2 mL) was stirred at room temperature for 1 h. Sodium triacetoxyborohydride (135 mg, 0.64 mmol) was added and the reaction mixture was stirred for 16 h. Concentration of the solvent under reduced pressure yielded a yellow solid that was dissolved in DMSO (3 mL) and filtered to give a yellow solution that was purified by HPLC to afford the desired product: $^1$H NMR (400 MHz, CD$_3$OD) δ 7.98 (d, 1H), 7.97 (d, 1H), 7.58 (d, 2H), 7.40 (d, 1H), 7.24 (s, 1H), 7.11 (d, 1H), 6.90 (dd, 1H), 4.35 (s, 2H), 4.00 (dd, 2H), 3.55 (m, 2H), 3.3 (m, 1H), 3.10 (m, 2H), 2.2 (m, 2H), 1.8 (m, 2H), 1.52 (m, 2H), 1.28 (m, 2H), 1.00 (dd, 3H), MS (ESI) m/z: Calculated: 407.21; Observed: 407.90 (M$^+$+1).

Compound 17

1-((6-(5-cyclohexylbenzofuran-2-yl)pyridin-3-yl)methyl)azetidine-3-carboxylic acid

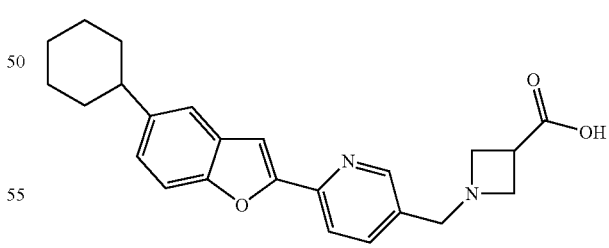

The title compound was prepared in the same manner as Example Compound 6 except using 6-bromo-3-pyridinecarboxaldehyde in step-3 (Scheme 2): >95% purity by LCMS, ESI-MS: 391.1 (M+H)$^+$, $^1$H NMR (400 MHz, CD$_3$OD) δ 8.81 (d, 1H), 7.94 (d, 1H), 7.65 (d, 1H), 7.59 (s, 1H), 7.50 (m, 2H), 7.35 (m, 1H), 4.44 (s, 2H), 4.45 (s, 2H), 4.34 (dd, 4H), 3.69 (m, 1H), 2.64-2.57(d, 1H), 1.89 (t, 4H), 1.58-1.41 (m, 4H), 1.38-1.26 (m, 2H).

Compound 18

1-(4-(5-(6-methylpyridin-2-yl)benzofuran-2-yl)benzyl)azetidine-3-carboxylic acid (Scheme 2)

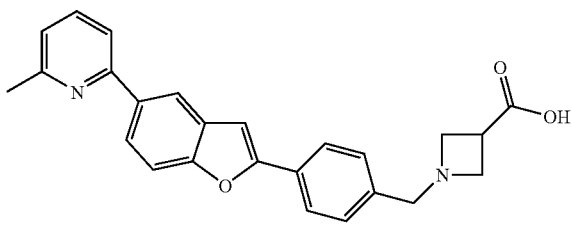

The title compound was prepared in the same manner as Example Compound 6 except using (6-methylpyridin-2-yl) zinc(II)bromide in step-1 (Scheme 2): >95% purity by LCMS, ESI-MS: 391.1 (M+H)$^+$, $^1$H NMR (400 MHz, CD$_3$OD) δ 8.42 (t, 1H), 8.22 (d, 1H), 8.07-8.10 (m, 3H), 7.77-7.88 (m, 3H), 7.62 (d, 2H), 7.50 (dd, 1H), 4.48 (s, 2H), 4.36(d, 4H), 3.71 (m, 1H), 2.85 (s, 31H).

Compound 19

1-(4-(5-phenoxybenzofuran-2-yl)benzyl)azetidine-3-carboxylic acid 1-(2,2-Diethoxy-ethoxy)-4-phenoxy-benzene

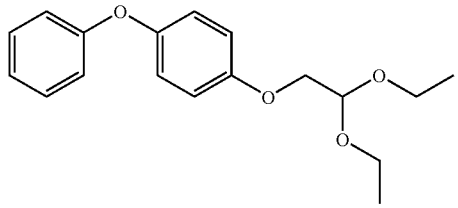

The title compound was prepared as Example Compound 1 (step 1 Scheme 1) in the general method described above.

5-Phenoxy-benzofuran

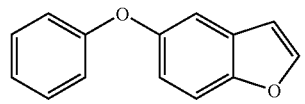

The title compound was prepared as Example Compound 1 (step 2 Scheme 1) in the general method described above (65% yield): $^1$H NMR (400 MHz, CDCl$_3$) δ 7.63 (d, 1H), 7.45 (d, 1H), 7.29 (m, 2H), 7.22 (d, 1H), 7.00-7.08 (m, 4H), 6.71 (m 1H).

5-phenoxybenzofuran-2-ylboronic acid

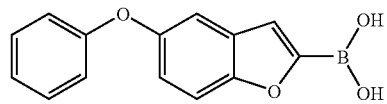

The title compound was prepared as Example Compound 1 (step 3 Scheme 1) in the general method described above (74% yield).

4-(5-phenoxybenzofuran-2-yl)benzaldehyde

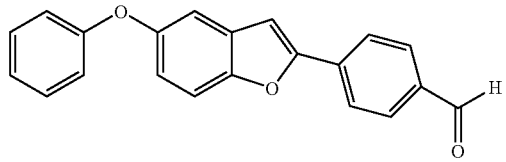

The title compound was prepared as Example Compound 1 (step 4 Scheme 1) in the general method described above (65% yield): $^1$H NMR (400 MHz, DMSO-d$_6$) δ 10.05 (s, 1H), 8.13 (d, 2H), 8.03 (d, 2H), 7.70 (d, 1H), 7.66 (br s, 1H), 7.39 (m, 4H), 7.10 (m, 2H), 7.00 (dd, 1H). MS (ESI) m/z: Calculated: 314.10; Observed: 315.10 (M$^+$+1).

1-(4-(5-phenoxybenzofuran-2-yl)benzyl)azetidine-3-carboxylic acid

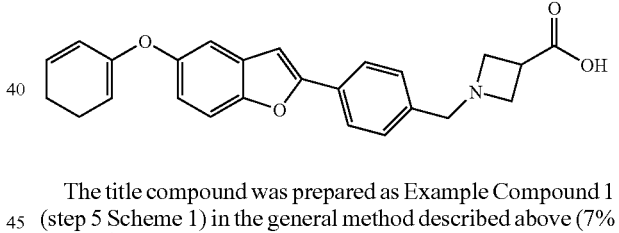

The title compound was prepared as Example Compound 1 (step 5 Scheme 1) in the general method described above (7% yield): $^1$H NMR (400 MHz, CD$_3$OD) δ 7.90 (d, 2H), 7.55 (m, 3H), 7.32 (m, 2H), 7.27 (s, 1H), 7.22 (d, 1H), 7.03 (m, 4H), 4.47 (s, 2H), 4.34 (m, 4H), 3.62 (m, 1H). MS (ESI) m/z: Calculated: 399.20; Observed: 399.90 (M$^+$+1).

Compound 20

1-((4-(5-Isopentylbenzofuran-2-yl)phenyl)methyl)azetidine-3-carboxylic acid

5-Isopentylbenzofuran

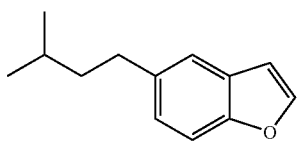

The title compound was prepared as Example Compound 6 (step 1 in Scheme 2) in the general method described above (75% yield): ¹H NMR (400 MHz, CDCl₃) δ 7.58 (d, J=2.0, 1H), 7.41-7.39 (m, 2H), 7.11 (dd, J=8.2, 2.0, 1H), 6.70 (br s, 1H), 2.72-2.68 (m, 2H), 1.62-1.51 (m, 3), 0.94 (d, J=6.6, 6H).

5-Isopentylbenzofuran-2-yl-2-boronic acid

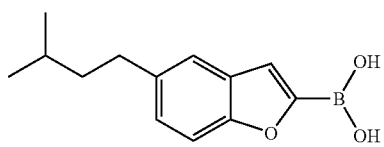

The title compound was prepared as Example Compound 6 (step 2 in Scheme 2) in the general method described above (53% yield): ¹H NMR (400 MHz, CDCl₃) δ 7.43-7.38 (m, 2H), 7.30 (s, 1H), 7.18 (d, J=8.5, 1H), 2.72-2.68 (m, 2H), 1.60-1.50 (m, 3), 0.94 (d, J=6.6, 6H).

4-(5-Isopentylbenzofuran-2-yl)benzaldehyde

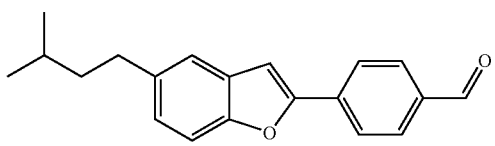

The title compound was prepared as Example Compound 6 (step 3 in Scheme 2) in the general method described above (79% yield): ¹H NMR (400 MHz, CDCl₃) δ 10.03 (s, 1H), 8.00 (d, J=8.5, 2H), 7.95 (d, J=8.5, 2H), 7.46-7.42 (m, 2H), 7.18-7.15 (m, 2H), 2.73-2.69 (m, 2H), 1.62-1.54 (m, 3), 0.95 (d, J=6.2, 6H).

1-((4-(5-Isopentylbenzofuran-2-yl)phenyl)methyl) azetidine-3-carboxylic acid

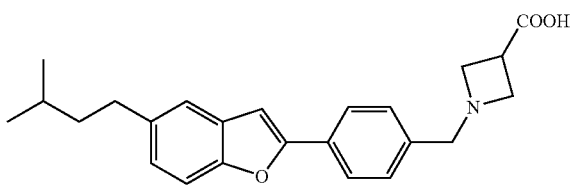

The title compound was prepared as Example Compound 6 (step 4 in Scheme 2) in the general method described above (63% yield): ¹H NMR (400 MHz, CD₃OD) δ 7.98 (d, J=8.3, 2H), 7.55 (d, J=8.3, 2H), 7.43-7.41 (m, 2H), 7.23 (s, 1H), 7.15 (d, J=8.8, 1H), 4.44 (s, 2H), 4.38-4.30 (m, 4H), 3.73-3.65 (m, 1H), 2.73-2.69 (m, 2H), 1.62-1.52 (m, 3), 0.96 (d, J=7.6, 6H). MS (ESI) m/z: Calculated: 377.2; Observed: 377.9 (M⁺+1).

Compound 21

1-((4-(6-Butoxybenzofuran-2-yl)phenyl)methyl) azetidine-3-carboxylic acid 1-(2,2-Diethoxyethoxy)-3-butoxybenzene

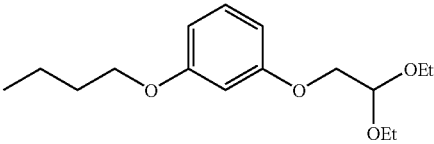

The title compound was prepared as Example Compound 1 (step 1 in Scheme 1) in the general method described above (86% yield): ¹H NMR (400 MHz, CDCl₃) δ 7.15 (t, J=7.4), 6.52-6.49 (m, 3H), 4.83 (t, J=5.1, 1H), 3.99 (d, J=5.1, 2H), 3.93 (t, J=6.6, 2H), 3.80-3.72 (m, 2H), 3.67-3.60 (m, 2H), 1.79-1.72 (m, 2H), 1.53-1.43 (m, 2H), 1.25 (t, J=7.3, 6H), 0.97 (t, J=7.3, 3H).

6-Butoxybenzofuran

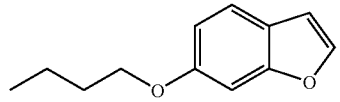

The title compound was prepared as Example Compound 1 (step 2 in Scheme 1) in the general method described above (83% yield): ¹H NMR (400 MHz, CDCl₃) δ 7.52 (d, J=2.2, 1H), 7.44 (d, J=8.5, 1H), 7.03 (d, J=2.2, 1H), 6.87 (dd, J=8.8, 2.5, 1H), 6.69-6.68 (m, 1H), 4.00 (t, J=6.6, 2H), 1.83-1.76 (m, 2H), 1.56-1.47 (m, 2H), 0.99 (t, J=7.4, 3H).

6-Butoxybenzofuran-2-yl-2-boronic acid

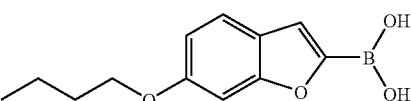

The title compound was prepared as Example Compound 1 (step 3 in Scheme 1) in the general method described above (76% yield): ¹H NMR (400 MHz, CDCl₃) δ 7.52-7.42 (m, 2H), 7.00 (br s, 1H), 6.90-6.85 (m, 1H), 4.00 (t, J=6.6, 2H), 1.82-1.78 (m, 2H), 1.56-1.48 (m, 2H), 0.98 (t, J=7.3, 3H).

4-(6-Butoxybenzofuran-2-yl)benzaldehyde

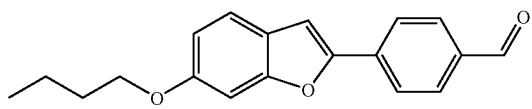

The title compound was prepared as Example Compound 1 (step 4 in Scheme 1) in the general method described above (62% yield): $^1$H NMR (400 MHz, CDCl$_3$) δ 9.94 (s, 1H), 7.94-7.89 (m, 4H), 7.45 (d, J=8.5, 2H), 7.10 (s, 1H), 7.05 (br d, J=2.2, 1H), 6.89 (dd, J=8.5, 2.2, 1H), 4.02 (t, J=6.2), 1.85-1.78 (m, 2H), 1.57-1.52 (m, 2H), 1.00 (t, J=7.3, 3H).

1-((4-(6-Butoxybenzofuran-2-yl)phenyl)methyl)azetidine-3-carboxylic acid

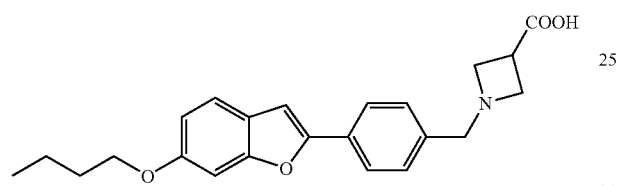

The title compound was prepared as Example Compound 1 (step 5 in Scheme 1) in the general method described above (46% yield): $^1$H NMR (400 MHz, CD$_3$OD) δ 7.94 (d, J=8.4, 2H), 7.53 (d, J=8.4, 2H), 7.47 (d, J=8.5, 1H), 7.21 (s, 1H), 7.11 (br d, J=2.2, 1H), 6.88 (dd, J=8.5, 2.2), 4.43 (s, 2H), 4.34-4.32 (m, 4H), 4.04 (t, J=6.2), 3.71-3.63 (m, 1H), 1.81-1.76 (m, 2H), 1.57-1.52 (m, 2H), 1.01 (t, J=7.3, 3H). MS (ESI) m/z: Calculated: 379.18; Observed: 379.8 (M$^+$+1).

Compound 22

1-((2-(5-butoxybenzofuran-2-yl)thiazol-5-yl)methyl)azetidine-3-carboxylic acid

2-(5-butoxybenzofuran-2-yl)thiazole-5-carbaldehyde

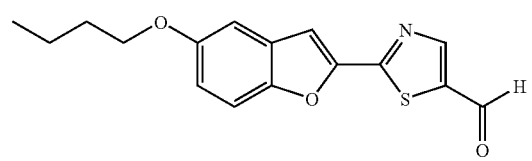

The title compound was prepared as Example Compound 1 (step 4 in Scheme 1) in the general method described above except using 2-bromothiazole-5-carbaldehyde (29% yield): $^1$H NMR (400 MHz, CDCl$_3$) δ 10.07 (s, 1H), 8.46 (dd, 1H), 7.45 (dd, 2H), 7.03 (dd, 2H), 4.01 (dd, 2H), 1.74 (m, 2H), 1.54 (m, 2H), 1.01 (t, 3H). MS (ESI) m/z: Calculated: 301.10; Observed: 302.10 (M$^+$+1).

1-((2-(5-butoxybenzofuran-2-yl)thiazol-5-yl)methyl)azetidine-3-carboxylic acid

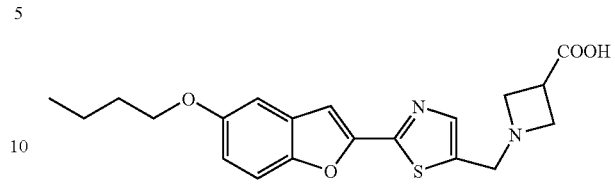

The title compound was prepared as Example Compound 1 (step 5 in Scheme 1) in the general method described above (36% yield): $^1$H NMR (400 MHz, CD$_3$OD) δ 8.06 (br s, 1H), 7.344 (m, 2H), 7.18 (m, 1H), 7.01 (ddd, 1H), 4.79 (s, 2H), 4.36 (m, 4H), 3.98 (m, 2H), 3.69 (m, 1H), 1.75 (m, 2H), 1.50 (m, 2H), 1.00 (t, 3H). MS (ESI) m/z: Calculated: 386.13; Observed: 386.90 (M$^+$+1).

Compound 23

1-((4-(5-Butoxybenzofuran-2-yl)3-fluorophenyl)methyl)azetidine-3-carboxylic acid

4-(5-Butoxybenzofuran-2-yl)4-fluorobenzaldehyde

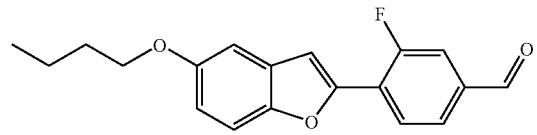

The title compound was prepared as Example Compound 1 (step 4 in Scheme 1) in the general method described above (36% yield): $^1$H NMR (400 MHz, CDCl$_3$) δ 10.02 (s, 1H), 8.18 (t, J=7.7, 1H), 7.73 (d, J=8.0, 1H), 7.66 (d, J=11.2, 1H), 7.44-7.39 (m, 2H), 7.09 (d, J=2.4, 1H), 6.92 (dd, J=2.4, 8.8, 1H), 4.01 (t, J=6.2), 1.81-1.76 (m, 2H), 1.57-1.51 (m, 2H), 1.01 (t, J=7.2, 3H).

1-((4-(5-Butoxybenzofuran-2-yl)3-fluorophenyl)methyl)azetidine-3-carboxylic acid

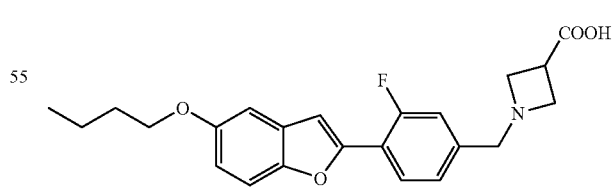

The title compound was prepared as Example Compound 1 (step 5 in Scheme 1) in the general method described above (51% yield): $^1$H NMR (400 MHz, CD$_3$OD) δ 8.08 (t, J=7.7, 1H), 7.44-7.37 (m, 3H), 7.25 (d, J=3.7, 1H), 7.14 (d, J=2.2, 1H), 6.94 (dd, J=8.8, 2.2), 4.35 (s, 2H), 4.18-4.15 (m, 4H), 4.01 (t, J=6.2), 3.45-3.37 (m, 1H), 1.82-1.75 (m, 2H), 1.57-

1.49 (m, 2H), 1.00 (t, J=7.2, 3H). MS (ESI) m/z: Calculated: 397.17; Observed: 397.9 (M⁺+1).

Compound 24

1-((4-(5-Butoxybenzofuran-2-yl)-3-methoxyphenyl)methyl)azetidine-3-carboxylic acid 4-(5-butoxybenzofuran-2-yl)-3-methoxybenzaldehyde

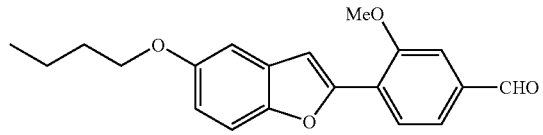

The title compound was prepared as Example Compound 1 (step 4 in Scheme 1) in the general method described above (65% yield): ¹H NMR (400 MHz, CD₃Cl) δ 10.03 (s, 1H), 8.22 (d, 1H), 7.59 (s, 1H), 7.50 (s, 1H), 7.45 (d, 1H), 7.41 (s, 1H), 7.08 (d, 1H), 6.93 (d, 1H), 4.16 (s, 3H), 4.05 (t, 2H), 1.84 (m, 2H), 1.61 (m, 2H), 1.04 (t, 3H). MS (ESI) m/z: Calculated: 324.14; Observed: 324.9 (M⁺+1).

1-((4-(5-Butoxybenzofuran-2-yl)-3-methoxyphenyl)methyl)azetidine-3-carboxylic acid

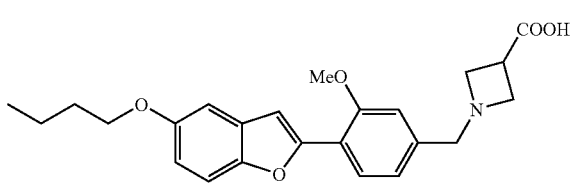

The title compound was prepared as Example Compound 1 (step 5 in Scheme 1) in the general method described above (36% yield): ¹H NMR (400 MHz, CD₃OD) δ 8.04 (d, 1H), 7.39 (s, 1H), 7.38 (s, 1H), 7.21 (s, 1H), 7.15 (d, 1H), 7.08 (s, 1H), 6.83 (d, 1H), 4.44 (s, 2H), 4.38 (m, 7H), 4.02 (m, 2H), 3.62 (m, 3H), 1.82 (m, 2H), 1.63 (m, 2H), 1.01 (t, 3H). MS (ESI) m/z: Calculated: 409.19; Observed: 409.9 (M⁺+1).

Compound 25

1-((5-(5-butoxybenzofuran-2-yl)thiophen-2-yl)methyl)azetidine-3-carboxylic acid 5-(5-butoxybenzofuran-2-yl)thiophene-2-carbaldehyde

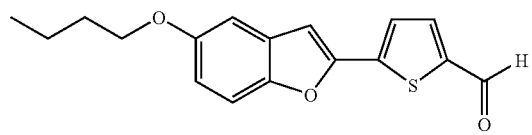

The title compound was prepared as Example Compound 1 (step 4 in Scheme 1) in the general method described above except using 5-bromothiophene-2-carbaldehyde (32% yield): ¹H NMR (400 MHz, CDCl₃) δ 9.92 (s, 1H), 7.73 (d, 1H), 7.51 (dd, 1H), 7.39 (d, 1H), 7.96 (m, 2H), 6.94 (dd, 1H), 3.98 (dd, 2H), 1.80 (m, 2H), 1.70 (m, 2H), 1.01 (t, 3H).

1-((5-(5-butoxybenzofuran-2-yl)thiophen-2-yl)methyl)azetidine-3-carboxylic acid

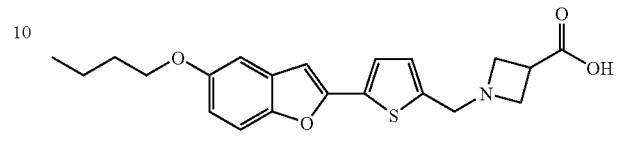

The title compound was prepared as Example Compound 1 (step 5 in Scheme 1) in the general method described above (27% yield): ¹H NMR (400 MHz, CD₃OD) δ 7.49 (br s, 1H), 7.35 (m, 2H), 7.03 (d, 2H), 6.89 (dd, 1H), 4.67 (s, 2H), 4.35 (m, 4H), 3.98 (m, 2H), 3.67 (m, 1H), 1.73 (m, 2H), 1.51 (m, 2H), 0.99 (t, 3H). MS (ESI) m/z: Calculated: 385.13; Observed: 385.70 (M⁺+1).

Compound 26

1-((6-(5-Butoxylbenzofuran-2-yl)pyridin-3-yl)methyl)azetidine-3-carboxylic acid 4-(5-Butoxybenzofuran-2-yl)pyridine-3-carboxaldehyde

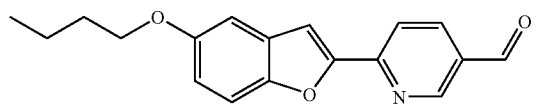

The title compound was prepared in the same manner as described in step 4 (Scheme 1) by using 6-bromo-3-pyridinecarboxaldehyde (48%): ¹H NMR (400 MHz, CDCl₃) δ 10.10 (s, 1H), 9.08 (s, 1H), 8.24 (d, 1H), 8.01 (d, 1H), 7.56 (s, 1H), 7.47 (d, 1H), 7.02 (s, 1H), 6.99 (d, 1H), 4.03 (q, 4H), 1.84-1.77 (m, 2H), 1.50-1.48 (m, 2H), 1.00 (t, 3H). MS (ESI) m/z: Calculated: 295.33; Observed: 296.2 (M⁺+1).

1-((6-(5-Butoxylbenzofuran-2-yl)pyridin-3-yl)methyl)azetidine-3-carboxylic acid

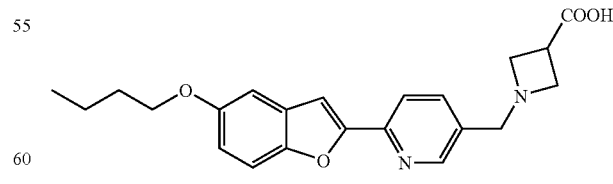

The title compound was prepared as in step 5 (Scheme 1) of the general method described earlier (68% yield): ¹H NMR (400 MHz, CDCl₃) δ 8.86 (s, 1H), 8.19 (d, 1H), 7.90 (d, 1H), 7.49 (s, 1H), 7.47 (d, 1H), 7.23 (d, 1H), 6.86 (s, 1H), 3.80 (q, 2H), 4.52-4.40 (m, 4H), 3.80 (t, 2H), 3.52-3.47 (m, 1H), 1.68-1.66 (m, 2H), 1.44-1.37 (m, 2H), 0.94 (t, 3H). MS (ESI) m/z: Calculated: 380.44; Observed: 381.0 (M$^+$+1).

Compound 27

1-(4-(5-cyclohexylbenzofuran-2-yl)3-fluorophenyl) methyl)azetidine-3-carboxylic acid 5-cyclohexylbenzofuran (Step 1 in Scheme 2)

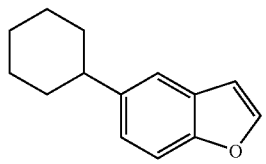

5-bromobenzofuran (500 mg, 2.55 mmol) was dissolved in a THF solution of cyclohexyl zinc(II)bromide (0.5M, 15 mL, 7.40 mmol) in a microwave reaction tube. Pd(P$^t$Bu$_3$)$_2$ (65 mg, 0.128 mmol, 0.05 eq.) was added to this solution. The mixture was purged with N$_2$ gas for 3-5 min and heated at 100° C. for 30 min under microwave irradiation. Upon completion of the reaction, the reaction mixture was diluted with ethyl acetate, washed with 1N HCl aqueous solution, brine, filtered through Celite. The filtrate was dried over Na$_2$SO$_4$ and concentrated. The residue was purified by silica gel column chromatography (ISCO system, 5% EtOAc in hexanes) to give 0.217 g desired product (43% yield): $^1$H NMR (400 MHz, CDCl$_3$) δ 7.57 (d, 1H), 7.41 (d, 2H), 7.15 (d, 1H), 6.72 (d, 1H), 2.58 (m, 1H), 1.92-1.74 (m, 4H), 1.51-1.35 (m, 4H), 1.31-1.25 (m, 2H).

5-cyclohexylbenzofuran-2-ylboronic acid (Step 2 in Scheme 2)

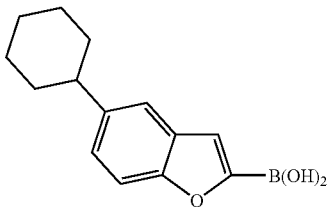

A solution of n-BuLi (360 μL, 0.9 mmol, 2.5M solution in hexanes) was added dropwise to a solution of 5-cyclohexylbenzofuran (150 mg, 0.75 mmol) in anhydrous THF (5 mL) at −78° C. The resulting mixture was stirred at −78° C. for 40 min, and treated with B($^i$PrO)$_3$ (260 μL, 1.13 mmol). The reaction mixture was allowed to warm up slowly to room temperature and stirred for 1 h. TLC indicated the completion of reaction. The reaction was cooled in ice-bath and quenched with 2N HCl (3 mL) and extracted with Et$_2$O. The combined organic extracts were washed with brine, dried and concentrated under reduced pressure to yield a desired boronic acid (0.156 g, 85% yield) without further purification for next step. $^1$H NMR (400 MHz, CDCl$_3$) δ 7.46 (s, 1H), 7.43 (d, 1H), 7.32 (s, 1H), 7.25 (d, 1H), 2.62 (m, 1H), 1.93-1.85 (m, 4H), 1.78-1.75 (m, 4H), 1.34-1.22 (m, 2H).

4-(5-cyclohexylbenzofuran-2-yl)2-fluorobenzaldehyde (Step 3 in Scheme 2)

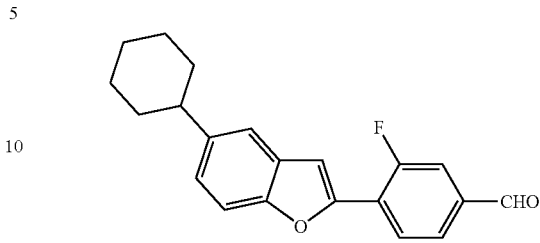

A mixture of 5-cyclohexylbenzofuran-2-ylboronic acid (75 mg, 0.30 mmol), 4-bromo-2-fluorobenzaldehyde (48 mg, 0.24 mmol), triethylamine (1.1 mL, 7.5 mmol) and bis(triphenylphosphine)palladium(II)chloride (12 mg, 0.05 mmol) in ethanol (11 mL) was irradiated in a microwave instrument at 100° C. for 20 min. The reaction mixture was cooled, and the solvent was removed. The residue was treated with water and extracted with ethyl acetate. The organic layer was dried and concentrated in vacuo (the aqueous work-up is optional). Purification by silica gel chromatography on ISCO system gave the title compound (51 mg, 49% yield). $^1$H NMR (400 MHz, CDCl$_3$) δ 10.04 (s, 1H), 8.00-7.97 (m, 2H), 7.46 (s, 1H), 7.43 (d, 2H), 7.32 (s, 1H), 7.25 (d, 1H), 2.62 (m, 1H), 1.95-1.77(m, 4H), 1.58-1.56 (m, 4H), 1.46-1.44 (m, 2H). MS (ESI) m/z: Calculated: 322.27; Observed: 323.2 (M$^+$+1).

1-(4-(5-cyclohexylbenzofuran-2-yl)3-fluorophenyl) methyl)azetidine-3-carboxylic acid (Step 4 in Scheme 2)

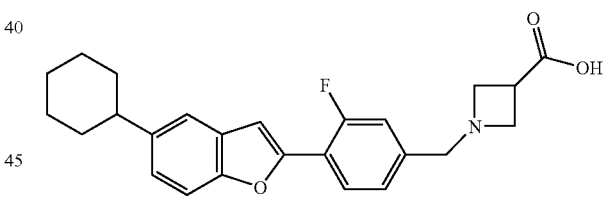

A mixture of 4-(5-cyclohexylbenzofuran-2-yl)3-fluorobenzaldehyde (40 mg, 0.12 mmol), acetic acid (10 μL, 0.15 mmol) and azetidine-3-carboxylic acid (15 mg, 0.15 mmol) in DCM/MeOH (1:1, 2 mL) was stirred at room temperature for 1 h. Sodium cyanoborohydride (3.0 mg, 0.05 mmol) was added and the reaction mixture was stirred for 3 h at room temperature. After concentration of solvent under reduced pressure, the resulting residue was dissolved in hot MeOH and filtered. The filtrate and the white solid, which was redissolved in hot DMSO, were both purified by reverse phase preparative HPLC (Phenomenex reverse phase Luna 5μ C18 (2) column, 60×21.2 mm ID) to yield the desired final product (12 mg, 42% yield) as a white powder: >95% purity by LCMS, $^1$H NMR (400 MHz, CD$_3$OD) δ 8.12 (d, 1H), 7.47-7.38 (m, 4H), 7.28-7.20 (m, 2H), 4.66 (s, 2H), 4.34 (m, 4H), 3.72 (m, 1H), 2.61 (m, 1H), 1.95-1.82 (m, 4H), 1.60-1.56 (m, 4H), 1.42-1.40 (m, 2H). MS (ESI) m/z: Calculated: 407.48; Observed: 408.2 (M$^+$+1).

Compound 28

1-((4-(5-(thiophen-2-yl)benzofuran-2-yl)phenyl)methyl)azetidine-3-carboxylic acid

5-(Thiophen-2-yl)benzofuran

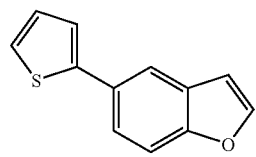

The title compound was prepared as Example Compound 6 (step 1 in Scheme 2) in the general method described above except using thiophen-2-ylboronic acid (55% yield). $^1$H NMR (400 MHz, CD$_3$Cl) δ 7.82 (s, 1H), 7.62 (s, 1H), 7.55-7.03 (m, 5H), 6.79 (d, 1H).

5-(Thiophen-2-yl)benzofuran-2-yl-boronic acid

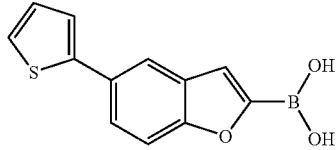

The title compound was prepared as Example Compound 6 (step 2 in Scheme 2) in the general method described above (77% yield). $^1$H NMR (400 MHz, CD$_3$Cl) δ 7.92 (s, 1H), 7.88 (s, 1H), 7.66-7.34 (m, 4H), 7.08 (d, 1H).

4-(5-(thiophen-2-yl)benzofuran-2-yl)benzaldehyde

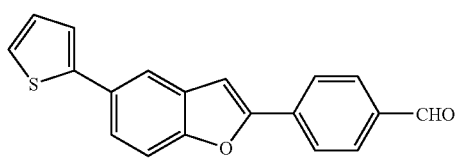

The title compound was prepared as Example Compound 6 (step 3 in Scheme 2) in the general method described above (61% yield): $^1$H NMR (400 MHz, CD$_3$Cl) δ 10.01 (s, 1H), 8.19 (d, 1H), 8.01 (d, 1H), 7.82 (s, 1H), 7.62-7.24 (m, 7H), 7.16 (dd, 1H). MS (ESI) m/z: Calculated: 304.06; Observed: 304.9 (M$^+$+1).

1-((4-(5-(thiophen-2-yl)benzofuran-2-yl)phenyl)methyl)azetidine-3-carboxylic acid

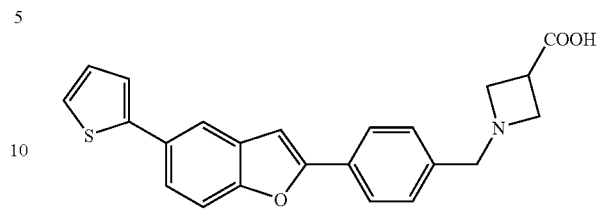

The title compound was prepared as Example Compound 6 (step 4 in Scheme 2) in the general method described above (31% yield): $^1$H NMR (400 MHz, DMSO-d$_6$) δ 8.01 (d, 2H), 7.87 (s, 1H), 7.64-7.44 (m, 7H), 7.19 (dd, 1H), 4.25 (m, 2H), 3.55 (m, 5H). MS (ESI) m/z: Calculated: 389.11; Observed: 389.9 (M$^+$+1).

Compound 29

3-(6-(5-benzylbenzofuran-2-yl)-3,4-dihydroisoqinolin-2(1H)-yl)propanoic acid

2-(3-bromophenyl)ethanamine (Step 1 in Scheme 7)

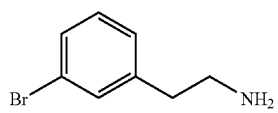

A suspension of LiAlH$_4$ (3.04 g, 80 mmole) in dry THF (100 ml) was cooled to −5° C. Concentrated H$_2$SO$_4$ (3.9 g, 40 mmole) was added dropwise, and the resulting mixture was stirred at −5° C. for 1 hour. A solution of 3-bromo-benzenacetontrile (9.80 g, 50 mmole) in THF (5 ml) was added dropwise, and the reaction was allowed to warm to room temperature when the addition was complete. The reaction was stirred at room temperature for 1 hour, and then cooled back to 0° C. and quenched by the addition of a 1:1 THF: H$_2$O mixture (12.4 ml). Et$_2$O was added (50 ml), followed by a 3.6 M solution of NaOH (24.4 ml). The mixture was filtered through Celite, and the solids were washed well with additional Et$_2$O. The organic phase was dried over Na$_2$SO$_4$, filtered, and concentrated in vacuo to provide the title compound (9.7 g, 97%). The crude compound was used in subsequent steps. $^1$H NMR (400 MHz, CDCl$_3$) δ 7.38-7.30 (m, 2H), 7.20-7.10 (m, 2H), 2.96 (t, 2H), 2.72 (t, 2H), 1.35 (br s, 2H). MS (ESI) m/z: Calculated: 199; Observed: 200/202 (M$^+$+1).

N-(3-bromophenethyl)-2,2,2-trifluoroacetamide (Step 2 in Scheme 7)

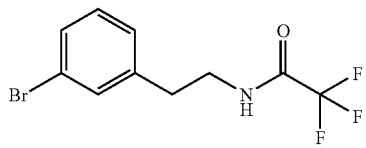

A mixture of 3-bromobenzeneethanamine (9.70 g, 48.5 mmole) and 2,6-lutidine (5.8 ml, 50.0 mmole) in dry CH$_2$Cl$_2$ (150 ml) was cooled to 0° C. Trifluoroacetic anhydride (5.6 ml, 40 mmole) was added dropwise; the reaction was then warmed to room temperature and allowed to stir for 24 hours. Water (120 ml) was added to the reaction, the phases were separated, and the aqueous layer was extracted with CH$_2$Cl$_2$ (2×100 ml). The combined organic phases were washed successively with 1N HCl (100 ml) and saturated NaHCO$_3$ (100 ml), and then dried over Na$_2$SO$_4$, filtered, and concentrated in vacuo to provide the tile compound (12.3 g, 86%). The crude compound was used in subsequent steps. $^1$H NMR (400 MHz, CDCl$_3$) δ 7.40 (d, J=8.0 Hz, 1H), 7.36 (s, 1H), 7.21 (t, J=7.6 Hz, 1H), 7.12 (t, J=7.6 Hz, 1H), 6.31 (br s, 1H), 3.59 (q, J=6.8 Hz, 2H), 2.87 (t, J=7.2 Hz, 2H).

1-(6-bromo-3,4-dihydroisoquinolin-2(1H)-yl)-2,2,2-trifluoroethanone and 1-(8-bromo-3,4-dihydroisoquinolin-2(1H)-yl)-2,2,2-trifluoroethanone (Step 3 in Scheme 7)

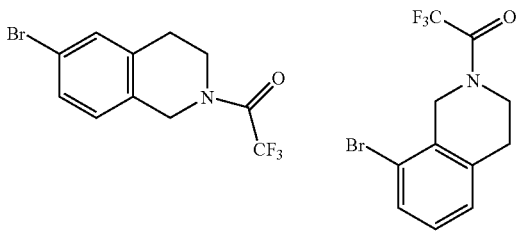

A mixture of glacial acetic acid (68 ml) and concentrated sulfuric acid (45 ml) was added to a mixture of N-(3-bromophenethyl)-2,2,2-trifluoroacetamide (12.3 g, 41.54 mmol) and paraformaldehyde (2.0 g). The reaction was stirred at room temperature for 24 hours, and then poured into 300 mL of cold water. The aqueous solution was extracted with EtOAc (3×150 ml). The combined organic phases were washed with saturated NaHCO$_3$ (200 ml) and water (2×200 ml). The organic phase was then dried over Na$_2$SO$_4$, filtered and concentrated in vacuo. The residue was purified on ISCO column (20% EtOAc/Hexane) to provide a mixture of the title compounds (9.6 g, 75%). $^1$H NMR (400 MHz, CDCl$_3$) δ 7.46 (dd, J=2.0 Hz, J=8.0 Hz, 0.33H), 7.38-7.31 (m, 1.33H), 7.15-7.09 (m, 0.67H), 7.05-6.98 (m, 0.67H), 4.75, 4.73, 4.69 (3×s, 2H), 3.90-3.80 (m, 2H), 3.00-2.90 (m, 2H). MS (ESI) m/z: Calculated: 306.98; Observed: 308/310 (M$^+$+1).

6-(5-benzylbenzofuran-2-yl)-1,2,3,4-tetrahydroisoquinoline (Step 4 in Scheme 7)

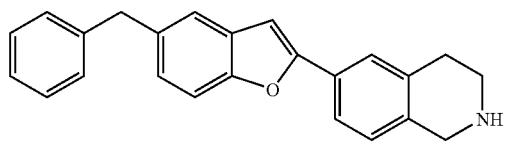

A solution of 5-benzylbenzofuran-2-ylboronic acid (252 mg, 1.0 mmole) in ethanol (3 ml) was added to a mixture of 1-(6-bromo-3,4-dihydroisoquinolin-2(1H)-yl)-2,2,2-trifluoroethanone and 1-(8-bromo-3,4-dihydroisoquinolin-2(1H)-yl)-2,2,2-trifluoroethanone (308 mg, 1.0 mmole), Pd(PPh$_3$)$_4$, toluene, and 2 M Na$_2$CO$_3$(3.5 ml). The resulting mixture was heated at reflux overnight. The reaction was concentrated in vacuo, and the residue was diluted with water. The aqueous phase was extracted with EtOAc (3×50 ml). The combined organic phases were washed with brine, dried over Na$_2$SO$_4$, filtered and concentrated in vacuo. The residue was purified on ISCO column (5% to 10% MeOH/CH$_2$Cl$_2$) to provide the title compounds (189 mg, 56%). $^1$H NMR (400 MHz, CDCl$_3$) δ 7.60 (m, 2H), 7.39 (dd, 1H), 7.37 (s, 1H), 7.25 (m, 5H), 7.10 (dd, 2H), 6.90 (s, 1H), 4.10 (s, 2H), 3.40 (s, 2H), 3.18 (m, 2H), 2.94 (m, 2H). MS (ESI) m/z: Calculated: 339.16; Observed: 340.10 (M$^+$+1).

Tert-butyl 3-(6-(5-benzylbenzofuran-2-yl)-3,4-dihydroisoquinolin-2(1H)-yl)propanoate (Step 5 in Scheme 6)

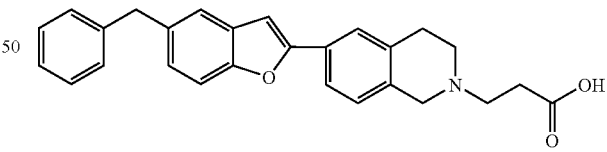

6-(5-benzylbenzofuran-2-yl)-1,2,3,4-tetrahydroisoquinoline (67 mg, 0.2 mmol) was dissolved in methanol (2 ml). DIEA (0.35 ml) and acrylic acid tert-butyl ester (51 mg, 0.4 mmol) were added. The mixture was headed to 90° C. for 30 minutes using microwave irradiation. All the solvents was evaporated and the crude product of tert-butyl 3-(6-(5-benzylbenzofuran-2-yl)-3,4-dihydroisoquinolin-2(1H)-yl)propanoate was used in the next step without further purification. MS (ESI) m/z: Calculated: 467.25; Observed: 468.30 (M$^+$+1).

3-(6-(5-benzylbenzofuran-2-yl)-3,4-dihydroisoquinolin-2(1H)-yl)propanoic acid (Step 6 in Scheme 7)

To a solution of tert-butyl 3-(6-(5-benzylbenzofuran-2-yl)-3,4-dihydroisoquinolin-2(1H)-yl)propanoate (40 mg, 0.086 mmole) in CH$_2$Cl$_2$(1 ml) was added TFA (1 ml). The mixture was stirred at room temperature for 3 hours. All the solvents were evaporated. The mixture was purified by reverse phase preparative HPLC to give the title compound (14 mg, 40%). $^1$H NMR (400 MHz, CD$_3$OD) δ 7.77 (m, 2H), 7.42 (dd, 1H), 7.40 (s, 1H), 7.20-7.30 (m, 5H), 7.10 (m, 3H), 4.50 (s, 2H), 4.04 (s, 2H), 3.64 (dd, 2H), 3.55 (dd, 2H), 3.26 (dd, 2H), 2.90 (dd, 2H). MS (ESI) m/z: Calculated: 411.18; Observed: 412.10 (M$^+$+1).

4.04 (s, 2H), 3.64 (dd, 2H), 3.55 (dd, 2H), 3.26 (dd, 2H), 2.90 (dd, 2H). MS (ESI) m/z: Calculated: 411.18; Observed: 412.10 (M$^+$+1).

Compound 30

1-(4-(5-cyclopentylbenzofuran-2-yl)benzyl)azetidine-3-carboxylic acid

5-Cyclopentylbenzofuran

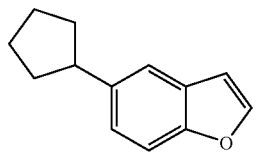

The title compound was prepared as Example Compound 6 (step 1 in Scheme 2) in the general method described above (67% yield): $^1$H NMR (400 MHz, CDCl$_3$) δ 7.58 (d, J=2.2, 1H), 7.45 (br d, J=1.8, 1H), 7.41 (d, J=8.8, 1H), 7.18 (dd, J=8.8, 1.8, 1H), 6.71 (dd, J=1.1, 2.2, 1H), 3.13-3.05 (m, 1H), 2.14-2.07 (m, 2H), 1.88-1.58 (m, 6H).

5-Cyclopentylbenzofuran-2-yl-2-boronic acid

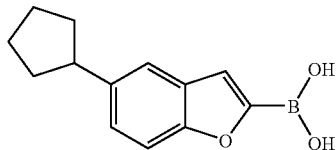

The title compound was prepared as Example Compound 6 (step 2 in Scheme 2) in the general method described above (yield): $^1$H NMR (400 MHz, CDCl$_3$) δ 7.50-7.45 (m, 2H), 7.43-7.39 (m, 1H), 7.31 (s, 1H), 3.12-3.05 (m, 1H), 2.14-2.06 (m, 2H), 1.80-1.60 (m, 6H).

4-(5-Cyclopentylbenzofuran-2-yl)benzaldehyde

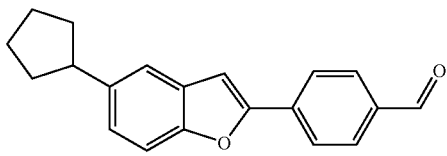

The title compound was prepared as Example Compound 6 (step 3 in Scheme 2) in the general method described above (95% yield): $^1$H NMR (400 MHz, CDCl$_3$) δ 10.03 (s, 1H), 8.00 (d, J=8.0, 2H), 7.94 (d, J=8.0, 2H), 7.51-7.44 (m, 3H), 7.15 (s, 1H), 3.14-3.06 (m, 1H), 2.20-2.10 (m, 2H), 1.88-1.62 (m, 6H).

1-(4-(5-cyclopentylbenzofuran-2-yl)benzyl)azetidine-3-carboxylic acid (Step 4 in Scheme 2)

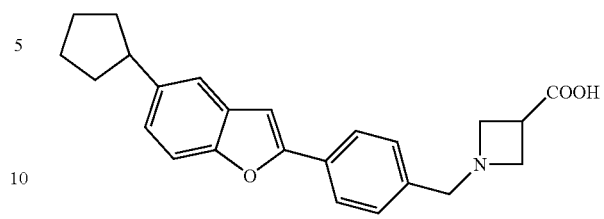

The title compound was prepared as Example Compound 6 (step 4 in Scheme 2) in the general method described earlier for reductive amination (71% yield). $^1$H NMR (400 MHz, CD$_3$OD) δ 8.02 (d, 2H), 7.57 (d, 2H), 7.49 (s, 1H), 7.44 (d, 1H), 7.25 (d, 2H), 4.56 (s, 2H), 4.30 (m, 4H), 3.62 (m, 1H), 3.11 (m, 1H), 2.25-2.12 (m, 2H), 1.90-1.66 (m, 6H). MS (ESI) m/z: Calculated: 375.46; Observed: 375.9 (M$^+$+1).

Compound 31

1-(3-fluoro-4-(5-(piperidin-1-yl)benzofuran-2-yl)benzyl)azetidine-3-carboxylic acid 1-(benzofuran-5-yl)piperidine (Step 1 of Scheme 3)

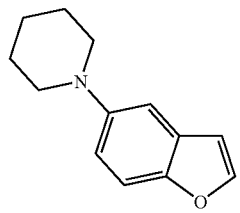

5-bromobenzofuran (2 g, 10 mmol), piperidine (1.2 mL, 12 mmol), Pd(dppf)Cl$_2$ (245 mg, 0.3 mmol), dppf(250 mg, 0.45 mmol) and sodium tert-butoxide (1.44 g, 15 mmol) was mixed in toluene (10 mL). The mixture was purged with N$_2$ gas for 3-5 min and heated at 120° C. for 30 min under microwave irradiation (Personal Chemistry Emrys™ Optimizer microwave reactor). Upon completion of the reaction, the reaction mixture was directly loaded on silica gel column and purified on ISCO system (<2% EtOAc in hexanes) to give 0.539 g desired product (27% yield): ESI-MS: 202.3 (M+H)$^+$, $^1$H NMR (400 MHz, CDCl$_3$) δ 7.58 (s, 1H), 7.40 (d, 1H), 7.15 (s, 1H), 7.00 (d, 1H), 6.65 (s, 1H), 3.10 (m, 4H), 1.70 (m, 4H), 1.48 (m, 2H). Note: the title compound appeared to be very volatile. The evaporation of solvent should be carried out very carefully.

5-(piperidin-1-yl)benzofuran-2-ylboronic acid (Step 2 of Scheme 3)

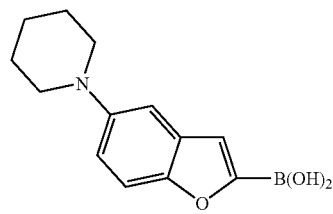

A solution of n-BuLi (334 μL, 0.83 mmol, 2.5 M solution in hexanes) was added dropwise to a solution of 1-(benzofuran-5-yl)piperidine (140 mg, 0.70 mmol) in anhydrous THF (5 mL) at −78° C. The resulting mixture was stirred at −78° C. for 40 min, and treated with B($^i$PrO)$_3$ (241 μL, 1.04 mmol). The reaction mixture was allowed to warm up slowly to room temperature and stirred for 1 h. TLC indicated the completion of reaction. The reaction was cooled in ice-bath and quenched with saturated NH$_4$Cl (1.5 mL) and extracted with Et$_2$O. The separated aqueous layer was neutralized to pH~5. The solution turned cloudy, which was extracted with ethyl acetate (×3). The combined organic extracts were concentrated in vacuo yielding the desired boronic acid as brown solids (0.16 g, 94% yield) without further purification for next step. ESI-MS: 246.3 (M+H)$^+$.

3-fluoro-4-(5-(piperidin-1-yl)benzofuran-2-yl)benzaldehyde (Step 3 of Scheme 3)

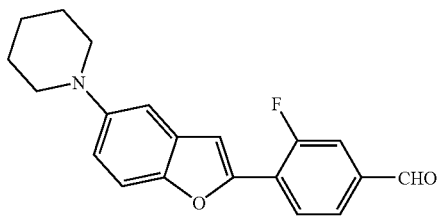

A mixture of 5-(piperidin-1-yl)benzofuran-2-ylboronic acid (50 mg, 0.204 mmol), 4-bromo-3-fluorobenzaldehyde (37 mg, 0.184 mmol), triethylamine (0.56 mL, 4.1 mmol) and bis(triphenylphosphine)palladium(II)chloride (14 mg, 0.02 mmol) in ethanol (5 mL) was irradiated in a microwave instrument at 100° C. for 20 min. The reaction mixture was cooled, and the solvent was removed. The residue was purification by silica gel chromatography on ISCO system yielding the title compound (15 mg, 15% yield). ESI-MS: 324.2 (M+H)$^+$, $^1$H NMR (400 MHz, CDCl$_3$) δ 10.00 (s, 1H), 8.19 (t, 1H), 7.75 (d, 1H), 7.67 (d, 1H), 7.43 (d, 1H), 7.35 (d, 1H), 7.14-7.11 (m, 2H), 3.13 (m, 4H), 1.77 (m, 4H), 1.59 (m, 2H).

1-(3-fuoro-4-(5-(piperidin-1-yl)benzofuran-2-yl)benzyl)azetidine-3-carboxylic acid trifluoroacetic acid salt(Step 4 of Scheme 3)

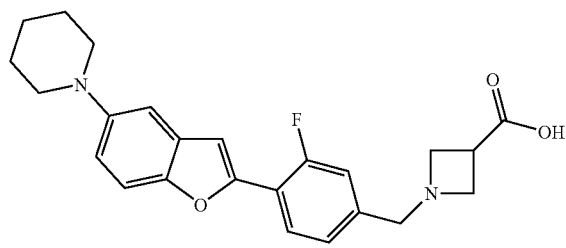

A mixture of 3-fluoro-4-(5-(piperidin-1-yl)benzofuran-2-yl)benzaldehyde (9 mg, 0.028 mmol), acetic acid (2.5 μL, 0.042 mmol) and azetidine-3-carboxylic acid (4.2 mg, 0.042 mmol) in DCM/MeOH (2:1, 0.9 mL) was stirred at room temperature for 1 h. Sodium cyanoborohydride (1.0 mg, 0.014 mmol) was added and the reaction mixture was stirred for 3 h at room temperature. After concentration of solvent under reduced pressure, the resulting residue was dissolved in DMSO, and purified by reverse phase preparative HPLC (Phenomenex reverse phase Luna 5μ C18 (2) column, 60×21.2 mm ID, mobil phase: A=0.05% TFA in water; B=0.05% TFA in acetonitrile. The flow rate was 12 mL/min. The gradient time was 2% B to 52% B over 25 min.) to yield the desired final product (10.3 mg, 70% yield) as a white powder (ditrifluroacetic acid salt): >95% purity by LCMS, ESI-MS: 409.1 (M+H)$^+$, $^1$H NMR (400 MHz, CD$_3$OD) δ 8.17 (t, 1H), 8.02(d, 1H), 7.81 (d, 1H), 7.66 (dd, 1H), 7.49-7.47 (m, 3H), 4.50 (s, 2H), 4.39 (dd, 4H), 3.72-3.70(m, 5H), 2.08 (m, 4H), 1.84(m, 2H).

Compound 32

1-((6-(5-benzylbenzofuran-2-yl)pyridin-3-yl)methyl)azetidine-3-carboxylic acid 6-(5-benzylbenzofuran-2-yl)nicotinaldehyde

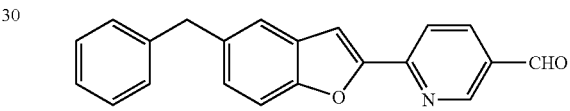

The title compound was prepared as the Example Compound 1 (step 4 in Scheme 1) in the general method described above except using 6-bromo-3-pyridinecarboxaldehyde (53% yield): $^1$H NMR (400 MHz, DMSO-d$_6$) δ 10.13 (s, 1H), 9.15 (s, 1H), 8.36 (d, 1H), 8.14 (m, 1H), 7.76 (d, 1H), 7.62 (m, 2H), 7.29 (m, 6H), 4.07 (s, 2H). MS (ESI) m/z: Calculated: 313.11; Observed: 314.20 (M$^+$+1).

1-((6-(5-benzylbenzofuran-2-yl)pyridin-3-yl)methyl)azetidine-3-carboxylic acid

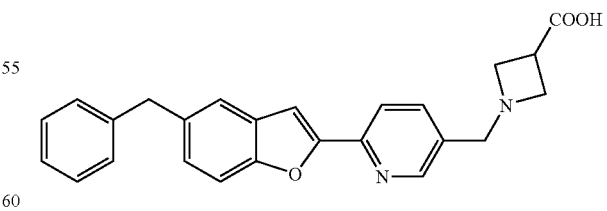

The title compound was prepared as Example Compound 1 (step 5 in Scheme 1) in the general method described above (33% yield): $^1$H NMR (400 MHz, CD$_3$OD) δ 8.68 (s, 1H), 8.01 (br s, 2H), 7.45 (m, 3H), 7.16 (m, 6H), 4.50 (s, 2H), 4.35 (m, 4H), 4.04 (s, 2H), 3.70 (m, 1H). MS (ESI) m/z: Calculated: 398.16; Observed: 399.00 (M$^+$+1).

Compound 33

1-((4-(5-benzylbenzofuran-2-yl)-3-methoxyphenyl)methyl)azetidine-3-carboxylic acid 4-(5-benylbenzofuran-2-yl)-3-methoxybenzaldehyde

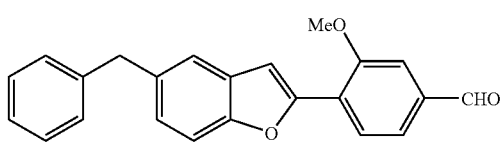

The title compound was prepared as Example Compound 1 (step 4 in Scheme 1) in the general method described above (60% yield): $^1$H NMR (400 MHz, CDCl$_3$) δ 10.03 (s, 1H), 8.22 (d, 1H), 7.64-7.44 (m, 1H), 4.16 (m, 5H). MS (ESI) m/z: Calculated: 342.13; Observed: 342.9 (M$^+$+1).

1-((4-(5-benzylbenzofuran-2-y)-3-methoxyphenyl)methyl)azetidine-3-carboxylic acid

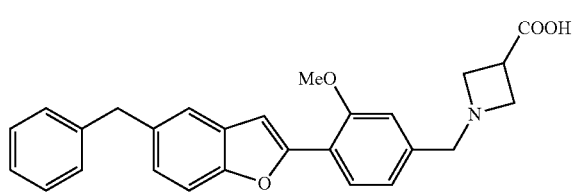

The title compound was prepared as Example Compound 1 (step 5 in Scheme 1) in the general method described above (50% yield): $^1$H NMR (400 MHz, DMSO-d$_6$) δ 7.98 (d, 1H), 7.42-7.07 (m, 1H), 4.18 (m, 2H), 3.82 (m, 5H), 3.57 (m, 1H), 3.14 (m, 4H). MS (ESI) m/z: Calculated: 427.18; Observed: 427.9 (M$^+$+1).

Compound 34

1-(4-(5-(piperidin-1-yl)benzofuran-2-yl)benzyl)azetidine-3-carboxylic acid 4-(5-(piperidin-1-yl)benzofuran-2-yl)benzaldehyde (Step 3 of Scheme 3)

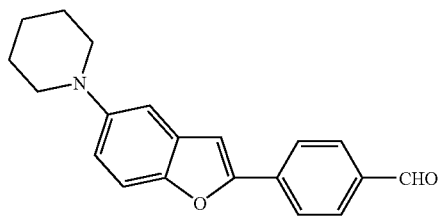

A mixture of 5-(piperidin-1-yl)benzofuran-2-ylboronic acid (90 mg, 0.367 mmol), 4-bromobenzaldehyde (62 mg, 0.330 mmol), triethylamine (1.0 mL, 7.3 mmol) and bis(triphenylphosphine)palladium(II)chloride (12.8 mg, 0.02 mmol) in ethanol (9 mL) was irradiated in a microwave instrument at 100° C. for 20 min. The reaction mixture was cooled, and the solvent was removed. The residue was purification by silica gel chromatography on ISCO system yielding the title compound (31 mg, 28% yield). ESI-MS: 306.4 (M+H)$^+$, $^1$H NMR (400 MHz, CDCl$_3$) δ 10.02 (s, 1H), 7.95 (dd, 4H), 7.42 (d, 1H), 7.11 (m, 2H), 7.07 (dd, 1H), 3.13 (t, 4H), 1.78-1.74 (m, 4H), 1.62-1.56 (m, 2H).

1-(4-(5-(piperidin-1-yl)benzofuran-2-yl)benzyl)azetidine-3-carboxylic acid (Step 4 of Scheme 3)

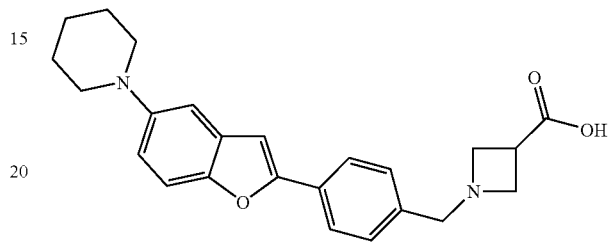

A mixture of 4-(5-(piperidin-1-yl)benzofuran-2-yl)benzaldehyde (31 mg, 0.102 mmol), acetic acid (9 μL, 0.15 mmol) and azetidine-3-carboxylic acid (12.3 mg, 0.122 mmol) in DCM/MeOH (2:1, 1.5 mL) was stirred at room temperature for 1 h. Sodium cyanoborohydride (3.2 mg, 0.051 mmol) was added and the reaction mixture was stirred for 3 h at room temperature. After concentration of solvent under reduced pressure, the resulting residue was dissolved in DMSO, and purified by reverse phase preparative HPLC (Phenomenex reverse phase Luna 5μ C18 (2) column, 60×21.2 mm ID, mobile phase: A=0.05% TFA in water; B=0.05% TFA in acetonitrile) to yield the desired final product (29.1 mg, 57% yield) as a white powder (ditrifluroacetic acid salt): >95% purity by LCMS, ESI-MS: 391.1 (M+H)$^+$, $^1$H NMR (400 MHz, CD$_3$OD) δ 8.05 (t, 3H), 7.79(d, 1H), 7.65-7.62(m, 3H), 7.47 (s, 1H), 4.48 (m, 2H), 4.38-4.32(m, 4H), 3.73-3.70(m, 5H), 2.15 (m, 4H), 1.16(m, 2H).

Compound 35

6-(5-benzylbenzofuran-2-yl)-2-(2-carboxyethyl)-3,4-dihydroisoquinolinium 2,2,2-trifluoroacetate (Step 6 in Scheme 7)

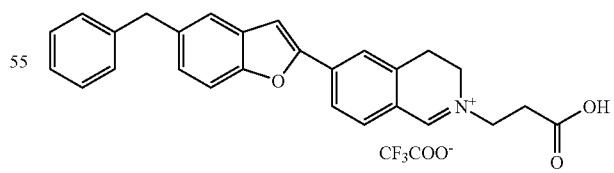

The title compound was isolated by reverse phase preparative HPLC during the purification of Compound 29. $^1$H NMR (400 MHz, CD$_3$OD) δ 9.17 (s, 1H), 8.04 (m, 2H), 7.90 (d, 1H), 7.50 (m, 3H), 7.23 (m, 6H), 4.28 (dd, 2H), 4.16 (dd, 2H), 4.08 (s, 2H), 3.34 (m, 2H), 3.03 (m, 2H). MS (ESI) m/z: Calculated: 410.18; Observed: 410.30 (M$^+$).

Compound 36

1-((4-(5-benzylbenzofuran-2-yl)-3-chlorophenyl)methyl)azetidine-3-carboxylic acid

4-(Ethoxycarbonyl)-2-chlorophenyl trifluoromethanesulfonate

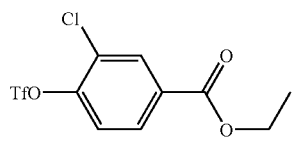

Trifluoroacetic anhydride (4.6 mL, 27.2 mmol) was added dropwise to a solution of ethyl 3-chloro-4-hydroxybenzoate (5.02 g, 25.0 mmol) and pyridine (2.2 mL, 27.5 mmol) in DCM (31 mL) at −10° C. The reaction mixture was stirred for 1 h at −10° C., allowed to warm up to rt and stirred for an additional 2 h. The reaction mixture was quenched with $H_2O$, and the resulting biphasic mixture was stirred for 15 min. The layers were separated and the organic layer was washed with 0.2 N HCl, water and brine. The final organic layer was dried ($Na_2SO_4$) and concentrated under reduced pressure to yield 6.8 g of a white solid, containing a mixture of triflate and remaining phenol. The mixture was redissolved in DCM and passed through a plug of silica gel to afford 3.8 g (45%) of pure triflate and 3 g of product impure with starting material. $^1$H NMR (400 MHz, $CDCl_3$) δ 8.21 (d, J=1.8, 1H), 8.03 (dd, J=8.5, 1.8, 1H), 7.43 (d, J=8.5, 1H), 4.42 (q, J=7.3, 2H), 1.41 (t, J=7.3, 3H).

Ethyl 4-(5-benzylbenzofuran-2-yl)-3-chlorobenzoate (Step 2 in Scheme 5)

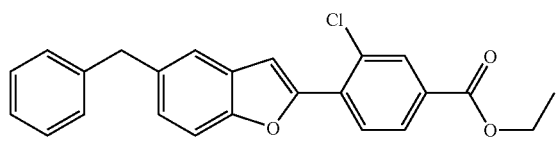

The title compound was prepared as Example Compound 40 (step 2 of Scheme 5) in the general method described above (94% yield): $^1$H NMR (400 MHz, $CDCl_3$) δ 8.15-8.12 (m, 2H), 8.00 (br d, J=8.4, 1H), 7.62 (s, 1H), 7.45-7.44 (m, 2H), 7.32-7.19 (m, 6H), 4.42 (q, J=7.3, 2H), 4.09 (s, 2H), 1.42 (t, J=7.3, 3H).

(4-(5-benzylbenzofuran-2-yl)-3-chlorophenyl)methanol (Step 3 in Scheme 5)

The title compound was prepared as Example Compound 40 (step 3 of Scheme 5) in the general method described above (66 mg of a 1:1 mixture of primary alcohol and aldehyde that lo was used without further purification).

4-(5-Benzylbenzofuran-2-yl)-3-chlorobenzaldehyde (Step 4 in Scheme 5)

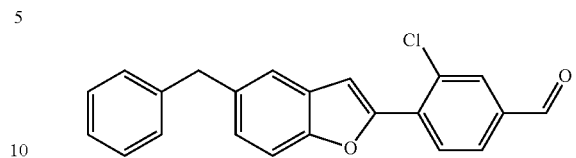

The title compound was prepared as Example Compound 40 (step 4 of scheme 5) in the general method described above (63% for the two steps): $^1$H NMR (400 MHz, $CDCl_3$) δ 10.00 (s, 1H), 8.24 (d, J=8.4, 1H), 7.99 (d, J=1.4, 1H), 7.86 (dd, J=8.0, 1.5), 7.69 (s, 1H), 7.47-7.45 (m, 2H), 7.32-7.19 (m, 6H), 4.10 (s, 2H).

1-(4-(5-Benzylbenzofuran-2-yl)-3-chlorobenzyl)azetidine-3-carboxylic acid (Step 5 in Scheme 5)

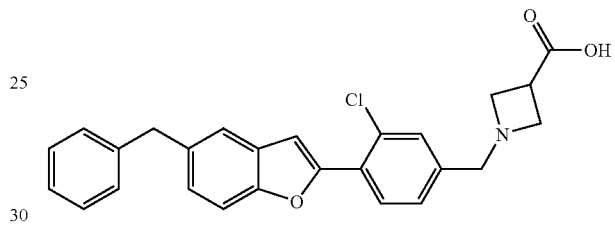

The title compound was prepared as Example Compound 40 (step 5 in Scheme 5) in the general method described above (42% yield): $^1$H NMR (400 MHz, DMSO-$d_6$) δ 8.05 (d, J=7.8, 1H), 7.76-7.72 (m, 1H), 7.59-7.54 (m, 4H), 7.27-7.16 (m, 6H), 4.46-4.36 (m, 2H), 4.32-4.16 (m, 4H), 4.03 (s, 2H), 3.64-3.58 (m, 1H). MS (ESI) m/z: Calculated: 431.13; Observed: 431.9 ($M^+$+1).

Compound 37

3-(6-(5-cyclopentylbenzofuran-2-yl)-3,4-dihydroisoquinolin-2(1H)-yl)propanoic acid

Tert-butyl 3-(6-hydroxy-3,4-dihydroisoquinolin-2(1H)-yl)propanoate (Step 1 in Scheme 8)

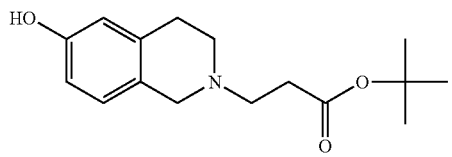

A solution of 1,2,3,4-tetrahydroisoquinolin-6-ol hydrobromide (345 mg, 1.5 mmol), tert-butyl acrylate (0.44 ml, 3.0 mmol) and N-ethyl-N-isopropylpropan-2-amine (2.6 ml, 15.0 mmol) in MeOH was irradiated in the microwave at 90° C. for 1800 s. Removal of the solvents gave the residue which was purified on ISCO column (2% to 5% MeOH/$CH_2Cl_2$) to provide the title compounds (332 mg, 80%). $^1$H NMR (400 MHz, $CD_3OD$) δ 6.85 (d, 1H), 6.55 (dd, 1H), 6.54 (s, 1H), 3.55 (s, 2H), 2.83 (m, 4H), 2.76 (m, 2H), 2.54 (dd, 2H), 1.45 (s, 9H). MS (ESI) m/z: Calculated: 277.17; Observed: 277.90 ($M^+$+1).

Tert-butyl 3-(6-(trifluoromethylsulfonyloxy)-3,4-dihydroisoquinolin-2(1H)-yl)propanoate (Step 2 in Scheme 8)

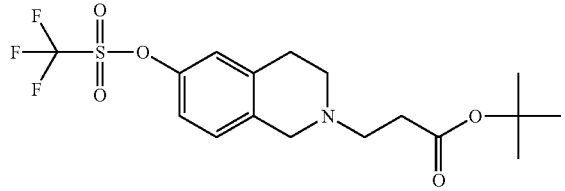

Trifluorosulfonic anhydride (87 μL, 0.52 mmol) was added to the solution of tert-butyl 3-(6-hydroxy-3,4-dihydroisoquinolin-2(1H)-yl)propanoate (111 mg, 0.4 mmol) in pyridine (5 mL) at 0° C. The reaction mixture was stirred for 1 hour at room temperature, concentrated, purified on ISCO column (2% to 5% MeOH/CH$_2$Cl$_2$) to provide the title compounds (93 mg, 57%). $^1$H NMR (400 MHz, CD$_3$OD) δ 7.20 (d, 1H), 7.12 (s, 1H), 7.10 (s, 1H), 3.68 (s, 2H), 2.94 (dd, 2H), 2.83 (dd, 2H), 2.78 (dd, 2H), 2.54 (dd, 2H), 1.44 (s, 9H). MS (ESD) m/z: Calculated: 409.12; Observed: 409.80 (M$^+$+1).

Tert-butyl 3-(6-(5-cyclopentylbenzofuran-2-yl)-3,4-dihydroisoquinolin-2(1H)-yl)propanoate (Step 3 in Scheme 8)

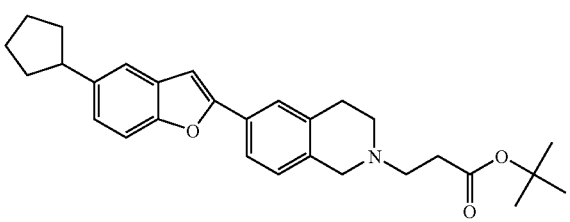

A mixture of 5-cyclopentylbenzofuran-2-ylboronic acid (78 mg, 0.34 mmol), tert-butyl 3-(6-(trifluoromethylsulfonyloxy)-3,4-dihydroisoquinolin-2(1H)-yl)propanoate (93 mg, 0.23 mmol), triethylamine (0.95 mL, 6.8 mmol) and bis(triphenylphosphine)palladium(II)chloride (16 mg, 0.02 mmol) in ethanol (5 mL) was irradiated in a microwave instrument at 100° C. for 20 min. The reaction mixture was cooled, and the solvent was removed. The residue was purification by silica gel chromatography on ISCO system yielding the title compound (34 mg, 34% yield). $^1$H NMR (400 MHz, CDCl$_3$) δ 7.59 (m, 2H), 7.40 (d, 2H), 7.15 (dd, 1H), 7.07 (d, 1H), 6.91 (s, 1H), 3.70 (s, 2H), 3.08 (m, 1H), 2.96 (dd, 2H), 2.85 (dd, 2H), 2.78 (dd, 2H), 2.54 (dd, 2H), 2.11 (m, 2H), 1.84 (m, 2H), 1.68 (m, 4H), 1.46 (s, 9H). MS (ESI) m/z: Calculated: 445.26; Observed: 446.00 (M$^+$+1).

3-(6-(5-cyclopentylbenzofuran-2-yl)-3,4-dihydroisoquinolin-2(1H)-yl)propanoic acid (Step 4 in Scheme 8)

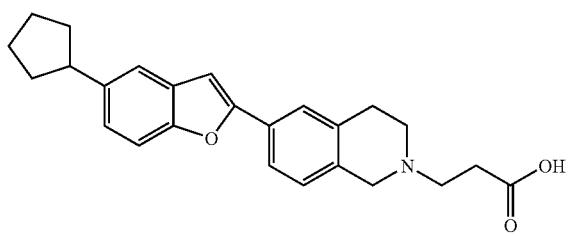

To a stirring solution of tert-butyl 3-(6-(5-cyclopentylbenzofuran-2-yl)-3,4-dihydroisoquinolin-2(1H)-yl)propanoate (25 mg, 0.056 mmole) in CH$_2$Cl$_2$ (0.5 ml) was added TFA (0.5 ml). The mixture was stirred at room temperature for 3 hours. Under reduced pressure, solvents and excess of TFA were removed affording a yellow oil which was rinsed with a mixture of CH$_2$Cl$_2$/Hexane (1:4) followed by ether. The solvents were removed under vacuum to give the title compound (19 mg, 90%). $^1$H NMR (400 MHz, CD$_3$OD) δ 7.82 (m, 2H), 7.47 (s, 1H), 7.40 (d, 1H), 7.30 (d, 1H), 7.20 (d, 1H), 7.19 (s, 1H), 4.54 (br, 2H), 3.69 (br, 2H), 3.60 (dd, 2H), 3.28 (m, 2H), 3.10 (m, 1H), 2.96(dd, 2H), 2.10 (m, 2H), 1.85 (m, 2H), 1.74 (m, 2H), 1.65 (m, 2H). MS (ESI) m/z: Calculated: 389.2; Observed: 390.20 (M$^+$+1).

Compound 38

1-(4-(5-(cyclopentylmethoxy)benzofuran-2-yl)-3-fluorobenzyl)azetidine-3-carboxylic acid 5-hydroxy benzofuan (Step 1 of Scheme 4)

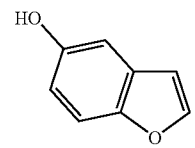

To an ice-cooled solution of 5-methylbenzofuran (0.5 g, 3.37 mmol) in DCM (7 mL) was added boron tribromide (3.4 mL, 3.37 mmol, 1M in DCM). The light brown solution was stirred at 0° C. for 1 h, another equivalent of boron tribromide (3.4 mL) was then added. The mixture was stirred at room temperature for 2 h. TLC analysis indicated the completion of the reaction. The mixture was poured into ice and the pH was adjusted to 7 with Na$_2$CO$_3$. The aqueous was extracted with DCM (×2). The combined organic layers were washed with brine, i5 dried over Na$_2$SO$_4$ and concentrated. The resulting light brown sold gave the satisfactory purity without further purification for next step: 0.36 g (79.6% yield), $^1$H NMR (400 MHz, CD$_3$OD) δ 7.59(d, J=2.0 Hz, 1H), 7.35(d, J=9.2 Hz, 1H), 7.01(d, J=2.4 Hz, 1H), 6.82 (dd, J=8.8 Hz, J=2.8 Hz, 1H), 6.67 (m, 1H), 4.73 (s, 1H).

5-(cyclopentylmethoxy)benzofuran (Step 2 of Scheme 4)

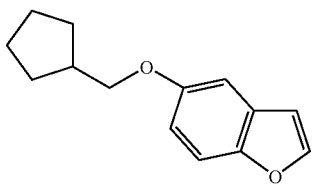

DEAD (362 mg, 2.09 mmol) was slowly added to a solution of 5-hydroxybenzofuran (200 mg, 1.49 mmol), triphenylphosphine (547 mg, 2.09 mmol) and cyclopentyl-methanol (203 mg, 2.0 2 mmol) in 3 mL of THF. The mixture was stirred at room temperature for 16 hours. The solvent was removed and the residue was purified by ISCO column chromatography using 0-5% AcOEt in Hexanes. The title compound was obtained as a white solid (0.208 g, 65% yield): 84% purity by HPLC; $^1$H NMR (400 MHz, CD$_3$OD) δ 7.58 (d, 1H), 7.38 (d, J=8.4 Hz, 1H), 7.06 (s, 1H), 6.91 (d, J=9.2 Hz, 1H), 6.69 (m, 1H), 3.82 (d, 2H), 2.39 (m, 1H), 1.85 (m, 2H), 1.63(m, 4H), 1.39(m, 2H).

5-(cyclopentylmethoxy)benzofuran-2-ylboronic acid (Step 3 of Scheme 1)

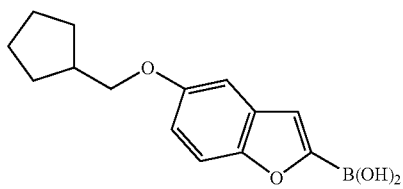

The title compound was prepared as Example Compound 1 (step 3 in Scheme 1) by the general method C described above (94.7% yield): $^1$H NMR (400 MHz, CD$_3$OD) δ 7.39 (d, J=9.2 Hz, 1H), 7.30 (s, 1H), 7.07 (d, 1H), 6.99 (dd, J=9.2 Hz, J=2.4 Hz, 1H), 3.82 (d, J=7.0 Hz, 2H), 2.39 (m, 1H), 1.86 (m, 2H), 1.63(m, 4H), 1.39(m, 2H).

4-(5-(cyclopentylmethoxy)benzofuran-2-yl)-3-fluorobenzaldehyde (Step 4 of Scheme 1)

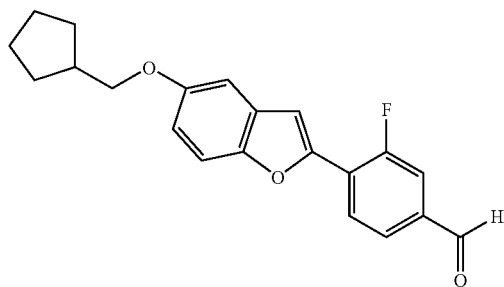

The title compound was prepared as Example Compound 1 (step 4 in Scheme 1) by the general method D described above (53% yield): ESI-MS: 339.3 (M+H)$^+$, $^1$H NMR (400 MHz, CD$_3$OD) δ 10.0 (s, 1H), 8.20 (t, 1H), 7.30 (s, 1H), 7.77 (d, 1H), 7.68 (d, 1H), 7.43 (d, 1H), 7.36 (d, 1H), 7.09 (s, 1H), 6.99 (dd, 1H), 3.88 (d, J=7.0 Hz, 2H), 2.39 (m, 1H), 1.86 (m, 2H), 1.63(m, 4H), 1.39(m, 2H).

1-(4-(5-(cyclopentylmethoxy)benzofuran-2-yl)-3-fluorobenzyl)azetidine-3-carboxylic acid (Step 5 of Scheme 1)

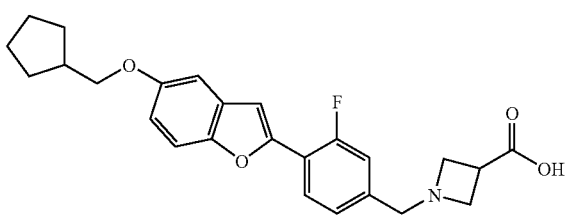

The title compound was prepared as Example Compound 1 (step 5 in Scheme I) by the general method E described above (79% yield): ESI-MS: 423.9 (M+H)$^+$, $^1$H NMR (400 MHz, CD$_3$OD) δ 8.11 (t, 1H), 7.45-7.40 (m, 3H), 7.28 (d, 1H), 7.15 (d, 1H), 6.95(dd, 1H), 4.46 (s, 2H), 4.36-4.34 (m, 4H), 3.88 (d, J=7.4 Hz, 2H), 3.68 (m, 1H), 2.38 (m, 1H), 1.85(m, 2H), 1.65 (m, 4H), 1.43(m, 2H).

Compound 39

1-(4-(5-(cyclopentylmethoxy)benzofuran-2-yl)benzyl)azetidine-3-carboxylic acid

4-(5-(cyclopentylmethoxy)benzofuran-2-yl)benzaldehyde (Step 4 of Scheme 1)

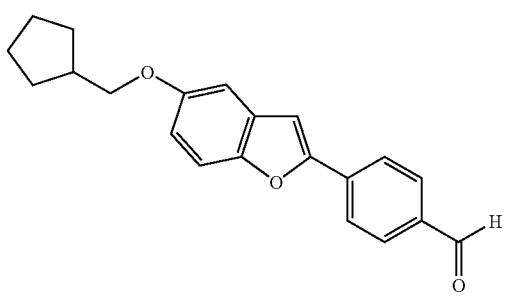

The title compound was prepared as Example Compound 1 (step 4 in Scheme I) by the general method D described above (33% yield): ESI-MS: 321.2 (M+H)$^+$, $^1$H NMR (400 MHz, CD$_3$OD) δ 10.0 (s, 1H), 7.98 (dd, 4H), 7.43 (d, 1H), 7.14 (s, 1H), 7.07 (d, 1H), 6.96 (dd, 1H), 3.88 (d, J=7.0 Hz, 2H), 2.41 (m, 1H), 1.86 (m, 2H), 1.63 (m, 4H), 1.39 (m, 2H).

1-(4-(5-(cyclopentylmethoxy)benzofuran-2-yl)benzyl)azetidine-3-carboxylic acid (Step 5 of Scheme 1)

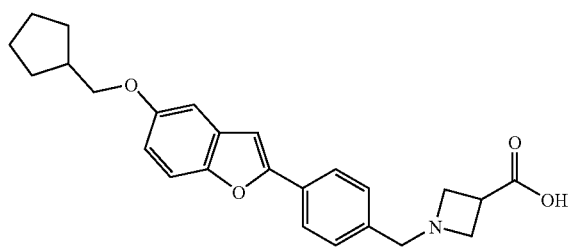

The title compound was prepared as Example Compound 1 (step 5 in Scheme 1) by the general method E described above (76% yield): ESI-MS: 405.9 (M+H)$^+$, $^1$H NMR (400 MHz, CD$_3$OD) δ 7.97 (d, 2H), 7.55 (d, 2H), 7.40 (d, 1H), 7.23 (s, 1H), 7.11 (d, 1H), 6.95(dd, 1H), 4.44 (s, 2H), 4.35-4.33 (m, 4H), 3.88 (d, J=7.0 Hz, 2H), 3.69 (m, 1H), 2.38 (m, 1H), 1.87 (m, 2H), 1.65 (m, 4H), 1.43 (m, 2H).

Compound 40

1-((4-(5-Benzylbenzofuran-2-yl)-3-cyanophenyl)methyl)azetidine-3-carboxylic acid

4-(ethoxycarbonyl)-2-cyanophenyl trifluoromethanesulfonoate

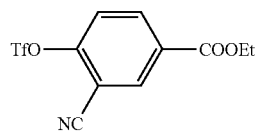

The title compound was prepared as Example Compound 36 in the general method described above (92% yield): $^1$H NMR (400 MHz, CDCl$_3$) δ 8.61 (s, 1H), 8.40 (d, 1H), 7.96 (d, 1H), 4.23 (q, 2H), 1.21 (t, 3H).

Ethyl-4-(5-benzylbenzofuran-2-yl)-3-cyanobenzoate (Step 4, Scheme 1)

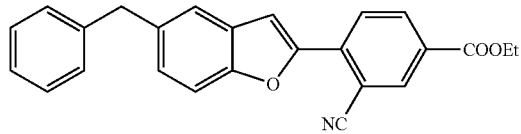

The title compound was prepared as Example Compound 1 (step 4, Scheme 1) in the general method described above (26% yield): $^1$H NMR (400 MHz, CDCl$_3$) δ 8.42 (s, 1H), 8.31 (d, 1H), 8.19 (d, 1H), 7.81 (s, 1H), 7.42 (d, 2H), 7.32-7.17 (m, 6H), 4.38 (q, 2H), 4.06 (s, 2H), 1.41 (t, 3H).

2-(5-Benzylbenzofuran-2-yl)-5-(hydroxymethyl)benzonitrile (Step 3, scheme 5)

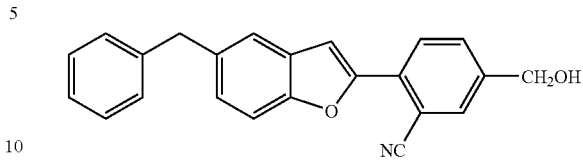

A solution of Ethyl-4-(5-benzylbenzofuran-2-yl)-3-cyanobenzoate (0.05 g, 0.13 mmol), sodium borohydride (0.01 g, 0.26 mmol) and calcium chloride (0.015 g, 0.13 mmol) in ethanol (2.5 mL) were stirred at room temperature for 1 hour. Water was added and the aqueous layer was extracted with ethyl acetate (×2, 10 mL). Organic layer was washed with water and brine and dried over sodium sulphate in 75% yield: $^1$H NMR (400 MHz, CDCl$_3$) δ 8.06 (d, 1H), 7.79 (s, 1H), 7.64 (d, 1H), 7.63 (s, 1H), 7.43-7.21 (m, 8H), 4.78 (s, 2H), 4.06 (s, 3H).

2-(5-Benzylbenzofuran-2-yl)-5-formylbenzonitrile (Step 4, Scheme 5)

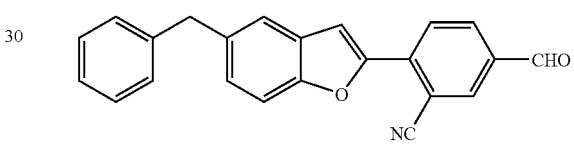

A suspension of 2-(5-Benzylbenzofuran-2-yl)-5-(hydroxymethyl)benzonitrile (0.03 g, 0.09 mmol), Molecular sieves 4A (0.2 g), TPAP (0.0016 mg, 0.004 mmol) and N-morpholino oxide (0.02 g, 0.18 mmol) in acetonitrile was stirred for 1 hour and then filtered through celite to obtain title compound in 93% yield (step 4, Scheme 5): $^1$H NMR (400 MHz, CDCl$_3$) δ 10.05 (s, 1H), 8.25 (s, 1H), 8.24 (d, 1H), 8.14 (d, 1H), 7.84 (s, 1H), 7.45 (m, 2H), 7.38-7.18 (m, 6H), 4.06 (s, 2H).

1-((4-(5-Benzylbenzofuran-2-yl)-3-cyanophenyl)methyl)azetidine-3-carboxylic acid (Step 5, Scheme 1)

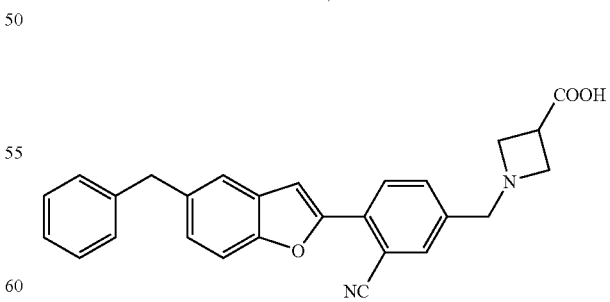

The title compound was prepared as Example Compound 1 (step 5, Scheme 1) in the general method described above (28% yield): $^1$H NMR (400 MHz, DMSO-d$_6$) δ 8.18 (d, 1H), 8.09 (s, 1H), 7.82 (d, 1H), 7.64 (d, 1H), 7.61 (s, 1H), 7.59 (d, 1H), 7.38-7.18 (m, 6H), 4.85 (bs, 2H), 4.42 (s, 2H), 4.38-4.25

(m, 4H), 4.06 (s, 2H), 3.74-3.66 (m, 1H). MS (ESI) m/z: Calculated: 422.16; Observed: 423.0 (M⁺+1).

Compound 41

1-(4-(5-benzylbenzofuran-2-yl)-3-fluorophenyl)methyl)pyrrolidine-3-carboxylic acid

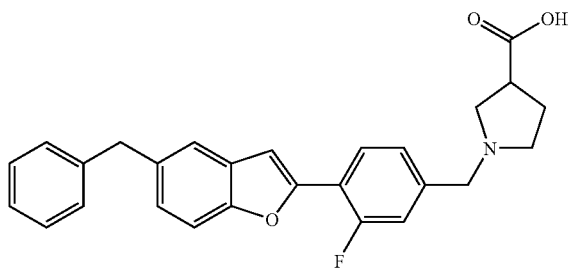

The title compound was prepared as racemic mixture according the reductive amination procedure as described in step 5 of Scheme-1 (60% yield). ¹H NMR (400 MHz, CD₃OD) δ 8.11 (t, 1H), 7.47-7.44 (m, 4H), 7.27-7.19 (m, 7H), 4.45 (s, 2H), 4.05 (s, 2H), 3.73-3.52 (m, 2H), 3.48-3.34 (m, 3H), 251-2.38 (m, 2H). MS (ESI) m/z: Calculated: 429.48; Observed: 430.0 (M⁺+1).

Compound 42

1-(4-(5-cyclopentylbenzofuran-2-yl)-3-fluorobenzyl)azetidine-3-carboxylic acid 4-(5-cyclopentylbenzofuran-2-yl)-3-fluorobenzaldehyde (Step 3 in Scheme 2)

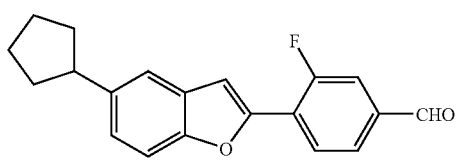

A solution of 5-cyclopentylbenzofuran-2-ylboronic acid (276 mg, 1.2 mmol), 4-bromobenzaldehyde (162 mg, 0.80 mmol), palladiumdichlorobis(triphenylphosphine) (56 mg, 0.08 mmol) and triethylamine (2.2 mL, 16 mmol) in EtOH (5 mL) was irradiated in the microwave at 100° C. for 20 min. The reaction mixture was cooled, and the solvent was removed. The residue was purification by silica gel chromatography on ISCO system yielding the title compound (34 mg, 34% yield). ¹H NMR (400 MHz, CDCl₃) δ 10.0 (s, 1H), 8.21 (dd, 1H), 7.77 (d, 1H), 7.66 (d, 1H), 7.51 (s, 1H), 7.46 (d, 1H), 7.38 (d, 1H), 7.28 (d, 1H), 3.11 (m, 1H), 2.12 (m, 2H), 1.84 (m, 2H), 1.72 (m, 2H), 1.64 (m, 2H).

1-(4-(5-cyclopentylbenzofuran-2-yl)-3-fluorobenzyl)azetidine-3-carboxylic acid (Step 5 in Scheme 1)

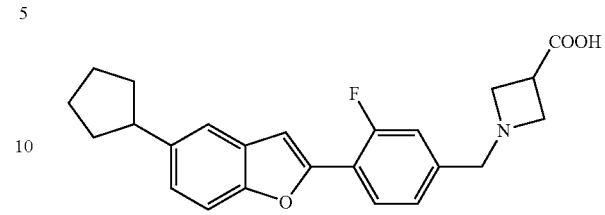

The title compound was prepared as Example Compound 1 (step 5 in Scheme 1) in the general method described above (20 mg, 18% yield): ¹H NMR (400 MHz, CD₃OD) δ 8.09 (dd, 1H), 7.51 (s, 1H), 7.44 (d, 1H), 7.40 (s, 1H), 7.37 (d, 1H), 7.29 (m, 2H), 4.34 (s, 2H), 4.14 (m, 4H), 3.39 (m, 1H), 3.11 (m, 1H), 2.12 (m, 2H), 1.85 (m, 2H), 1.74 (m, 2H), 1.65 (m, 2H). MS (ESI) m/z: Calculated: 393.17; Observed: 393.90 (M⁺+1).

Compound 43

1-((4-(5-Benzylbenzofuran-2-1)-3-methlphenyl)methyl)azetidine-3-carboxlic acid

Methyl 4-(5-benzylbenzofuran-2-yl)-3-methylbenzoate (Step 2 in Scheme 5)

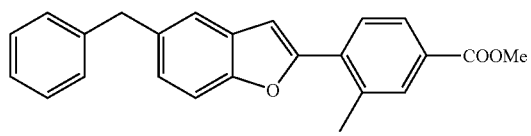

The title compound was prepared as Example Compound 40 (step 2, Scheme 5) in the is general method described above (52% yield): ¹H NMR (400 MHz, CDCl₃) δ 7.89 m, 2H), 7.61 (d, 1H), 7.42-7.17 (m, 8H), 6.95 (s, 1H), 4.06 (s, 2H), 3.82 (s, 1H), 2.61 (s, 3H).

(4-(5-Benzylbenzofuran-2-yl)-3-methylphenyl)methanol (Step 3 in Scheme 5)

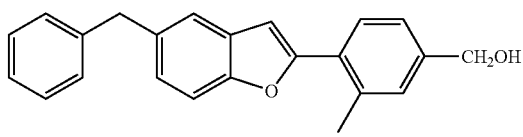

The title compound was prepared as Example Compound 40 (step 3, Scheme 5) in the general method described above (86% yield): ¹H NMR (400 MHz, CDCl₃) δ 7.94 (s, 1H), 7.82 (d, 1H), 7.48-7.07 (m, 9H), 6.85 (s, 1H), 4.67 (brs, 1H), 4.06 (s, 4H), 2.58 (s, 3H).

4-(5-Benzylbenzofuran-2-yl)-3-methylbenzaldehyde (Step 4 in Scheme 5)

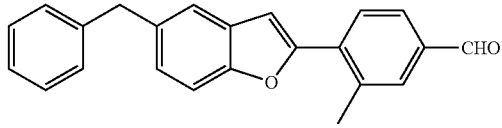

The title compound was prepared as Example Compound 40 (step 4, Scheme 5) in the general method described above (90% yield): $^1$H NMR (400 MHz, CDCl$_3$) δ 10.03 s, 1H), 8.07 (d, 1H), 7.81 (m, 2H), 7.46-7.17 (m, 8H), 7.01 (s, 1H), 4.08 (s, 2H), 2.63 (s, 3H).

1-((4-(5-Benzylbenzofuran-2-yl)-3-methylphenyl)methyl)azetidine-3-carboxylic acid (Step 5 in Scheme 1)

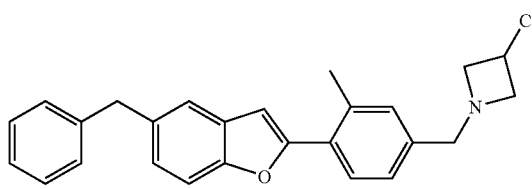

The title compound was prepared as Example Compound 1 (step 5, Scheme 1) in the general method described above (62% yield): $^1$H NMR (400 MHz, CD$_3$OD) δ 7.92 (d, 1H), 7.51-7.17 (m, 10H), 7.03 (s, 1H), 4.84 (bs, 2H), 4.41 (s, 2H), 4.37-4.22 (m, 4H), 4.08 (s, 2H), 3.68-3.61 (m, 1H), 2.63 (s, 3H). MS (ESI) m/z: Calculated: 411.18; Observed: 411.9 (M$^+$+1).

Compound 44

3-(6-(5-butoxybenzofuran-2-yl)-3,4-dihydroisoquinolin-2(1H)-yl)propanoic acid Tert-butyl 3-(6-(5-butoxybenzofuran-2-yl)-3,4-dihydroisoquinolin-2(1H)-yl)propanoate (Step 3 in Scheme 8)

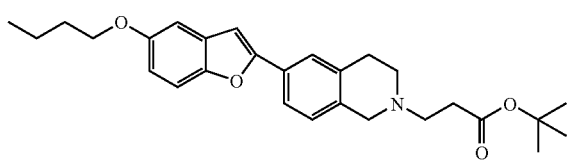

The title compound was prepared as Example Compound 37 (step 3 in Scheme 8) in the general method described above (57 mg, 50% yield): $^1$H NMR (400 MHz, CDCl$_3$) δ 7.57 (m, 2H), 7.36 (d, 1H), 7.06 (d, 1H), 7.00 (d, 1H), 6.88 (s, 1H), 6.85 (d, 1H), 3.99 (dd, 2H), 3.68 (s, 2H), 2.96 (dd, 2H), 2.85 (dd, 2H), 2.78 (dd, 2H), 2.53 (dd, 2H), 1.80 (m, 2H), 1.56 (m, 2H), 1.45 (s, 9H), 1.00 (t, 3H). MS (ESI) m/z: Calculated: 449.26; Observed: 449.90 (M$^+$+1).

3-(6-(5-butoxybenzofuran-2-yl)-3,4-dihydroisoquinolin-2(1H)-yl)propanoic acid (Step 4 in Scheme 8)

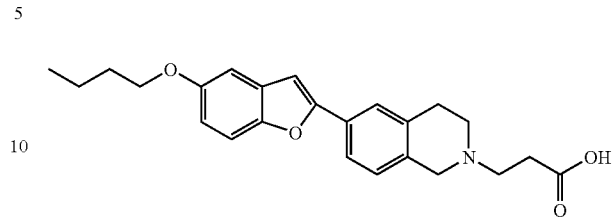

The title compound was prepared as Example Compound 37 (step 4 in Scheme 8) in the general method described above (25 mg, 75% yield): $^1$H NMR (400 MHz, CD$_3$OD) δ 7.79 (m, 2H), 7.38 (d, 1H), 7.30 (d, 1H), 7.17 (s, 1H), 7.09 (d, 1H), 6.88 (dd, 1H), 4.54 (br s, 2H), 4.00 (dd, 2H), 3.68 (m, 2H), 3.60 (dd, 2H), 3.21 (m, 1H), 2.95 (dd, 2H), 1.78 (m, 2H), 1.53 (m, 2H), 1.00 (t, 2H). MS (ESI) m/z: Calculated: 393.19; Observed: 394.20 (M$^+$+1).

Compound 45

3-(5-(5-benzylbenzofuran-2-yl)-2,3-dihydro-1H-inden-2-ylamino)-propanoic acid

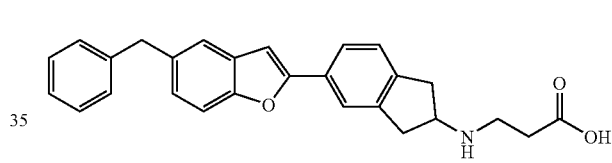

The title compound was prepared according the reductive amination procedure as described in step 5 of Scheme-1 (60% yield). $^1$H NMR (400 MHz, CD$_3$Cl$_3$) δ 7.80-7.74 (m, 2H), 7.54 (d, 1H), 7.40-7.22 (m, 7H), 7.18 (d, 1H), 6.92 (s, 1H), 4.79 (s, 1H), 4.02 (s, 2H), 3.28-2.92 (m, 4H), 2.73 (t, 2H), 2.48-2.30 (m, 2H). MS (ESI) m/z: Calculated: 411.49; Observed: 412.7 (M$^+$+1).

Compound 46

3-((4-(5-Benzylbenzofuran-2-yl)-3-fluorophenyl)methylamino)-3-methylbutanoic acid

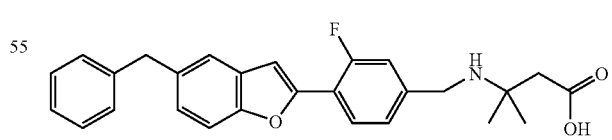

The title compound was prepared as Example Compound 1 (step 5, in Scheme 1) in the general method described above but using 3-amino-3-methylbutanoic acid instead of azetidine-3-carboxylic acid (46% yield): $^1$H NMR (400 MHz, CD$_3$OD) δ 8.11 (t, J=7.8, 1H), 7.50-7.17 (m, 12H), 4.28 (s, 2H), 4.07 (s, 2H), 1.51 (s, 6H). MS (ESI) m/z: Calculated: 431.19; Observed: 432.0 (M$^+$+1).

Compound 47

1-((4-(5-cyclopentylbenzofuran-2-yl)-3-methoxyphenyl)methyl)azetidine-3-carboxylic acid 4-(5-cyclopentylbenzofuran-2-yl)-3-methoxybenzaldehyde

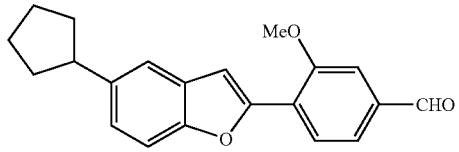

The title compound was prepared as Example Compound 1 (step 4 in Scheme 1) in the general method described above (56% yield): $^1$H NMR (400 MHz, CDCl$_3$) δ 10.04 (s, 1H), 8.21 (d, 1H), 7.77 (d, 1H), 7.59-7.19 (m, 5H), 4.04 (s, 3H), 3.11 (m, 1H), 2.15-1.77(m, 4H), 1.58-1.56 (m, 4H).

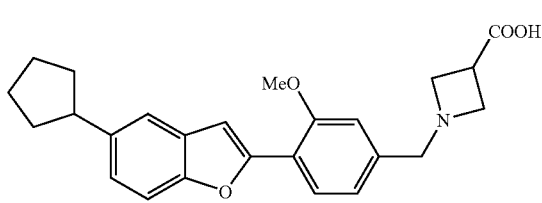

The title compound was prepared as Example Compound 1 (step 5, in Scheme 1) in the general method described earlier for reductive amination (71% yield). $^1$H NMR (400 MHz, CD$_3$OD) δ 8.16 (d, 1H), 7.45 (s, 1H), 7.41-7.36 (m, 2H), 7.26-7.17 (m, 3H), 4.85 (bs, 2H), 4.41 (s, 2H), 4.32 (m, 4H), 4.04 (s, 3H), 3.62 (m, 1H), 3.11 (m, 1H), 2.25-2.12 (m, 2H), 1.90-1.66 (m, 6H). MS (ESI) m/z: Calculated: 405.19; Observed: 405.9 (M$^+$+1).

Compound 48

1-((4-(5-Benzylbenzofuran-2-yl)-3,5-difluorophenyl)methyl)azetidine-3-carboxylic acid 4-(5-Benzylbenzofuran-2-yl)-3,5-difluorobenzaldehyde

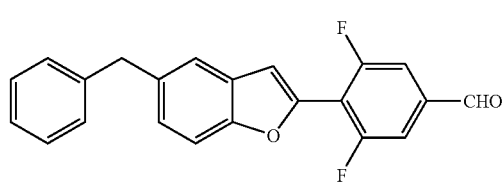

The title compound was prepared as Example Compound 1 (step 4, Scheme 1) in the general method described above (66% yield): $^1$H NMR (400 MHz, CDCl$_3$) δ 10.04 (s, 1H), 7.66 (s, 1H), 7.45 (d, 1H), 7.41-7.17 (m, 8H), 4.08 (s, 2H).

1-((4-(5-Benzylbenzofuran-2-yl)-3,5-difluorophenyl)methyl)azetidine-3-carboxylic acid

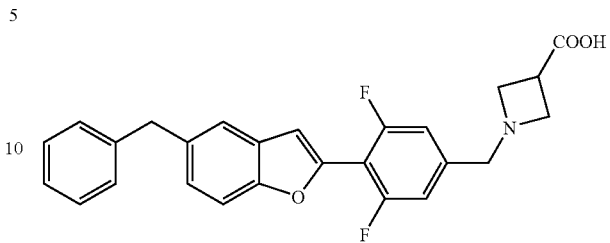

The title compound was prepared as Example Compound 1 (step 5, Scheme 1) in the general method described above (62% yield): $^1$H NMR (400 MHz, DMSO-d$_6$) δ 7.55 (s, 1H), 7.47 (d, 1H), 7.41-7.12 (m, 8H), 4.42 (s, 2H), 4.37-4.22 (m, 7H), 4.06 (s, 2H), 3.72-3.64 (m, 1H). MS (ESI) m/z: Calculated: 433.15; Observed: 433.9 (M$^+$+1).

Compound 49

1-(4-(5-(cyclopentylmethoxy)benzofuran-2-yl)-3-fluorobenzyl)azetidine-3-carboxylic acid 5-(cyclopropylmethoxy)benzofuran (Step 2 of Scheme 4)

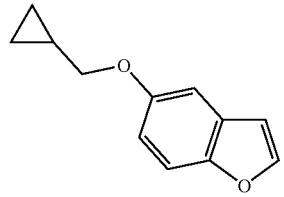

The title compound was prepared as Example Compound 38 (step 2 in Scheme 4) by the general method described above (49% yield): $^1$H NMR (400 MHz, CD$_3$OD) δ 7.60 (d, 1H), 7.38 (d, 1H), 7.05 (s, 1H), 6.94 (d, 1H), 6.69 (m, 1H), 3.84 (d, 2H), 1.31(m, 1H), 0.66 (m, 2H), 0.37 (m, 2H).

5-(cyclopropylmethoxy)benzofuran-2-ylboronic acid (Step 3 of Scheme 1)

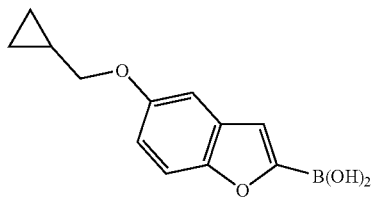

The title compound was prepared as Example Compound 1 (step 3 in Scheme 1) by the general method C described above (98% yield): $^1$H NMR (400 MHz, CD$_3$OD) δ 7.39 (d, 1H), 7.29 (s, 1H), 7.06 (d, 1H), 7.00 (dd, 1H), 3.83 (d, J=6.9 Hz, 2H), 1.30 (m, 1H), 0.66 (m, 2H), 0.38 (m, 2H).

4-(5-(cyclopropylmethoxy)benzofuran-2-yl)-3-fluorobenzaldehyde (Step 4 of Scheme 1)

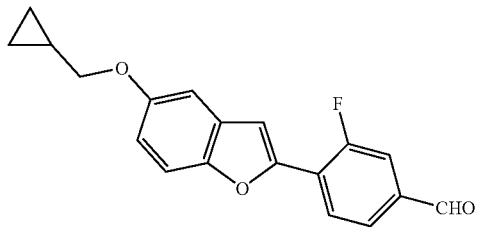

The title compound was prepared as Example Compound 1 (step 4 in Scheme 1) by the general method D described above (50% yield): ESI-MS: 311.2 (M+H)+, $^1$H NMR (400 MHz, CD$_3$OD) δ 10.01 (s, 1H), 8.20 (t, 1H), 7.78 (d, 1H), 7.69 (d, 1H), 7.44 (d, 1H), 7.36 (d, 1H), 7.08 (s, 1H), 7.01 (d, 1H), 3.85 (d, J=7.1 Hz, 2H), 1.32 (m, 1H), 0.68 (m, 2H), 0.38 (m, 2H).

1-(4-(5-(cyclopentylmethoxy)benzofuran-2-y)-3-fluorobenzyl)azetidine-3-carboxylic acid

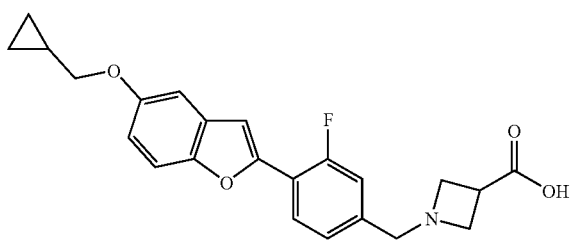

The title compound was prepared as Example Compound 1 (step 5 in Scheme 1) by the general method E described above (68% yield): ESI-MS: 395.9 (M+H)+, $^1$H NMR (400 MHz, CD$_3$OD) δ 8.01 (t, 1H), 7.35-7.30 (m, 3H), 7.17 (d, 1H), 7.04 (d, 1H), 6.87 (dd, 1H), 4.37 (s, 2H), 4.28-4.25 (m, 4H), 3.76 (d, J=6.7 Hz, 2H), 3.60 (m, 1H), 1.18 (m, 2H), 0.54-0.51 (m, 2H), 0.28-0.26 (m, 2H).

Compound 50

1-((4-(5-Butoxybenzofuran-2-yl)-3-chlorophenyl)methyl)azetidine-3-carboxylic acid 2-Chloro-4-formylphenyl trifluoromethanesulfonate

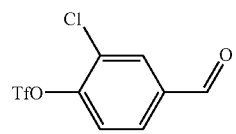

The title compound was prepared as Example Compound 36 in the general method described above but using 3-chloro-4-hydroxybenzaldehyde instead of ethyl 3-chloro-4-hydroxybenzoate (92% yield): $^1$H NMR (400 MHz, CDCl$_3$) δ 10.00 (s, 1H), 8.06 (d, J=1.8, 1H), 7.88 (dd, J=8.4, 1.8, 1H), 7.55 (d, J=8.4, 1H).

4-(5-Butoxybenzofuran-2-yl)-3-chlorobenzaldehyde

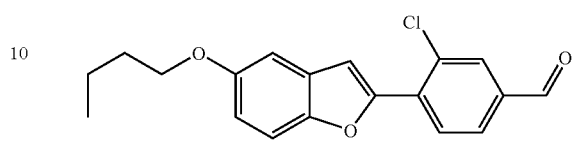

The title compound was prepared as Example Compound 1 (step 4 in Scheme 1) in the general method described above (72% yield): $^1$H NMR (400 MHz, CDCl$_3$) δ 10.00 (s, 1H), 8.25 (d, J=8.0, 1H), 7.99 (d, J=1.4, 1H), 7.86 (dd, J=8.4, 1.5), 7.70 (s, 1H), 7.42 (d, J=8.8), 7.10 (d, J=2.6, 1H), 6.99 (dd, J=8.8, 2.5), 4.01 (t, J=6.5, 2H), 1.84-1.77 (m, 2H), 1.54-1.49 (m, 2H), 1.00 (t, J=7.3, 3H).

1-((4-(5-Butoxybenzofuran-2-yl)-3-chlorophenyl)methyl)azetidine-3-caboxylic acid

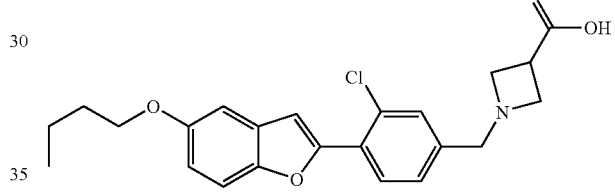

The title compound was prepared as Example Compound 1 (step 5 in Scheme 1) in the general method described above (66% yield): $^1$H NMR (400 MHz, CD$_3$OD) δ 8.13 (d, J=8.4, 1H), 7.70 (d, J=1.8, 1H), 7.57 (s, 1H), 7.53 (dd, J=8.4, 1.8, 1H), 7.42 (d, J=9.1, 1H), 7.15 (d, J=2.5, 1H), 6.95 (dd, J=9.1, 2.5), 4.45 (s, 2H), 4.40-4.32 (m, 4H), 4.00 (t, J=6.5, 2H), 3.74-3.66 (m, 1H), 1.81-1.74 (m, 2H), 1.58-1.49 (m, 2H), 1.00 (t, J=7.3, 3H). Calculated: 413.14; Observed: 413.9 (M$^+$+1).

Compound 51

1-((3-chloro-4-(5-cyclopentylbenzofuran-2-yl)phenyl)methyl)azetidine-3-carboxylic acid Ethyl 3-chloro-4-(5-cyclopentylbenzofuran-2-yl)benzoate

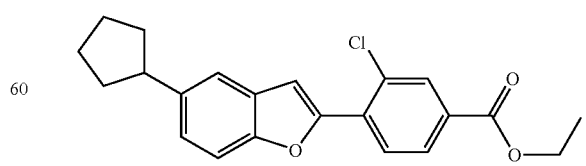

The title compound was prepared as Example Compound 40 (step 2 in Scheme 5) in the general method described above (73% yield): $^1$H NMR (400 MHz, CDCl$_3$) δ 8.14 (d, J=7.8, 2H), 8.00 (d, J=8.1, 1H), 7.64 (s, 1H), 7.51-7.44 (m, 3H), 4.42 (q, J=7.0, 2H), 3.12-3.08 (m, 1H), 2.16-2.08 (m, 2H), 1.84-1.58 (m, 6H), 1.42 (t, J=7.3, 3H).

(3-Chloro-4-(5-cyclopentylbenzofuran-2-yl)phenyl)methanol

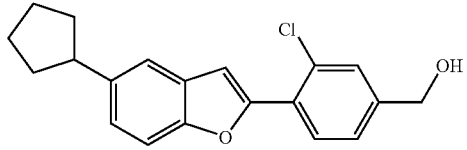

The title compound was prepared as Example Compound 40 (step 3 in Scheme 5) in the general method described above (142 mg of a 1:1 mixture of primary alcohol and aldehyde that was used without further purification).

3-Chloro-4-(5-cyclopentylbenzofuran-2-yl)benzaldehyde

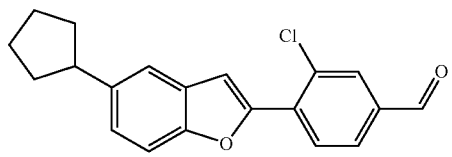

The title compound was prepared as Example Compound 40 (step 4 of Scheme 5) in the general method described above (61% for the two steps): $^1$H NMR (400 MHz, CDCl$_3$) δ 10.00 (s, 1H), 8.25 (d, J=8.1, 1H), 7.99 (s, 1H), 7.86 (d, J=8.1), 7.71 (s, 1H), 7.52 (s, 1H), 7.47 (d, J=8.8, 1H), 7.27 (d, J=8.8, 1H), 3.16-3.06 (m, 1H), 2.18-2.06 (m, 2H), 1.88-1.60 (m, 6H).

1-((3-chloro-4-(5-cyclopentylbenzofuran-2-yl)phenyl)methyl)azetidine-3-carboxylic acid

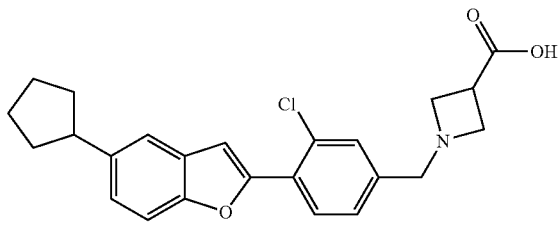

The title compound was prepared as Example Compound 40 (step 5 of Scheme 5) in the general method described above (60% yield): $^1$H NMR (400 MHz, CD$_3$OD) δ 8.16 (d, J=8.1, 1H), 7.70 (d, J=1.5, 1H), 7.61 (s, 1H), 7.55-7.53 (m, 2H), 7.45 (d, J=8.8, 1H), 7.28 (dd, J=8.4, 1.5), 4.45 (s, 2H), 4.40-4.34 (m, 4H), 3.72-3.64 (m, 1H), 3.16-3.10 (m, 1H), 2.15-2.06 (m, 2H), 1.87-1.66 (m, 6H). Calculated: 409.14; Observed: 409.9 (M$^+$+1).

Compound 52

3-(N-((4-(5-(cyclopentylmethoxy)benzofuran-2-yl)-3-fluorophenyl)methyl)-N-(2-hydroxyethyl)amino)propanoic acid

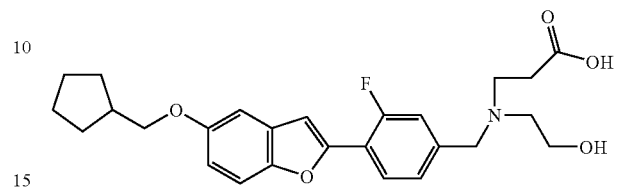

The title compound was prepared as Example Compound 1 (step 5, Scheme 1) in the general method described above except using 3-(2-hydroxyethylamino)propanoic acid (13% yield): $^1$H NMR (400 MHz, DMSO-d$_6$) δ 7.57 (d, 1H), 7.55-7.47 (m, 2H), 7.26 (m, 2H), 7.22 (s, 1H), 6.96 (d, 1H), 4.82 (bs, 3H), 4.42 (s, 2H), 4.06 (s, 2H), 3.92-3.65 (m, 4H), 2.75-2.33 (m, 4H), 1.95-1.31 (m, 9H). MS (ESI) m/z: Calculated: 455.21; Observed: 455.9 (M$^+$+1).

Compound 53

1-((3-fluoro-4-(5-morpholinobenzofuran-2-yl)phenyl)methyl)azetidine-3-carboxylic acid 4-(benzofuran-5-yl)morpholine

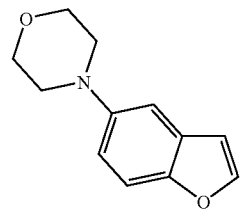

The title compound was prepared as Example Compound 31 (step 1 Scheme 3) in the general method described above (52% yield): $^1$H NMR (400 MHz, CDCl$_3$) δ 7.46 (s, 1H), 7.36 (d, 1H), 6.95 (s, 1H), 6.81 (d, 1H), 6.58 (s, 1H), 3.78 (m, 4H), 2.95 (m, 4H).

5-morpholinobenzofuran-2-yl-2-boronic acid

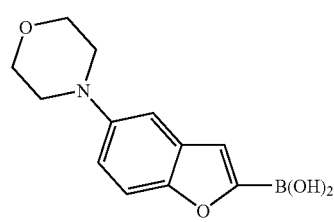

The title compound was prepared as Example Compound 31 (step 2 scheme 3) in the general method described above (72% yield): MS (ESI) m/z: Calculated: 247.1; Observed: 248.1 (M$^+$+1).

3-fluoro-4-(5-morpholinobenzofuran-2-yl)benzaldehyde

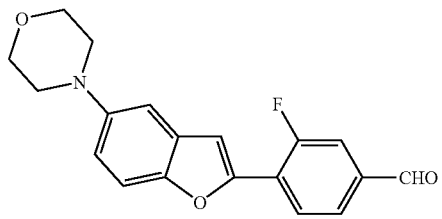

The title compound was prepared as Example Compound 31 (step 3 Scheme 3) in the general method described above (52% yield): ¹H NMR (400 MHz, CDCl₃) δ 10.01 (s, 1H), 7.76 (d, 1H), 7.61 (d, 1H), 7.55-7.06 (m, 5H), 3.86 (m, 4H), 3.15 (m, 4H).

1-((3-fluoro-4-(5-morpholinobenzofuran-2-yl)phenyl)methyl)azetidine-3-carboxylic acid

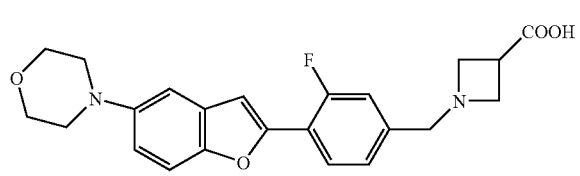

The title compound was prepared as Example Compound 1 (step 5 in Scheme 1) in the general method described above (28% yield): ¹H NMR (400 MHz, CD₃OD) δ 8.03 (t, 1H), 7.56 (d, 1H), 7.53 (d, 1H), 7.43 (d, 1H), 7.22 (d, 1H), 7.19 (d, 1H) 7.05 (dd, 1H), 4.50 (s, 2H), 4.39 (dd, 4H), 3.72-3.70(m, 6H), 2.08 (m, 4H), 1.84(m, 2H). MS (ESI) m/z: Calculated: 410.1; Observed: 411.1 (M⁺+1).

Compound 54

4-((4-(5-benzylbenzofuran-2-yl)-3-fluorophenyl)methyl)morpholine-2-carboxylic acid

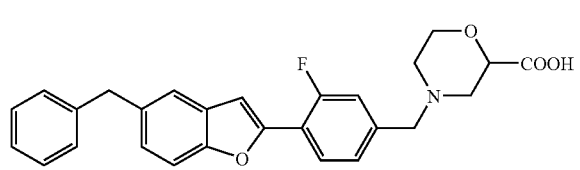

The title compound was prepared as Example Compound 1 (step 5 in Scheme 1) in the general method described above but using morpholine-2-carboxylic acid instead of azetidine-3-carboxylic acid (57% yield): ¹H NMR (400 MHz, CD₃OD) δ 8.09 (t, J=7.8, 1H), 7.46-7.42 (m, 4H), 7.28-7.14 (m, 7H), 4.38 (br d, J=9.5, 1H), 4.30-4.21 (m, 2H), 4.13-4.04 (m, 1H), 4.06 (s, 2H), 3.83 (br t, J=10.6, 1H), 3.53 (br d, J=12.4, 1H), 3.30-3.22 (m, 1H), 3.13-3.00 (m, 2H). MS (ESI) m/z: Calculated: 445.17; Observed: 445.90 (M⁺+1).

Compound 55

4-((4-(5-(cyclopentylmethoxy)benzofuran-2-yl)-3-fluorophenyl)methyl)morpholine-2-carboxylic acid

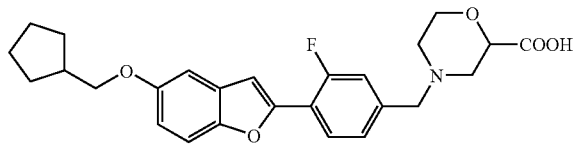

The title compound was prepared as Example Compound 1 (step 5 in Scheme 1) in the general method described above but using morpholine-2-carboxylic acid instead of azetidine-3-carboxylic acid (57% yield): ¹H NMR (400 MHz, CD₃OD) δ 8.06 (t, J=7.8, 1H), 7.44-7.42 (m, 3H), 7.24 (d, J=3.3, 1H), 7.13 (d, J=2.5, 1H), 6.95-6.92 (m, 1H), 4.38 (dd, J=9.5, 2.6, 1H), 4.21-4.09 (m, 3H), 3.88 (d, J=7.0, 2H), 3.81 (t, J=10.2, 1H), 3.45 (br d, J-11.4, 1H), 3.15 (br d, J=12.4, 1H), 3.03-2.91 (m, 2H), 2.41-2.34 (m, 1H), 1.90-1.83 (m, 2H), 1.71-1.57 (m, 4H), 1.46-1.37 (m, 2H). MS (ESI) m/z: Calculated: 453.20; Observed: 453.90 (M⁺+1).

Compound 56

1-(5-(5-benzylbenzofuran-2-yl)-2,3-dihydro-1H-inden-2-yl azetidine-3-carboxylic acid

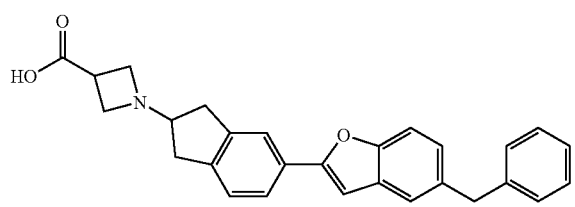

The title compound was prepared according the reductive amination procedure as described in step 5 of Scheme-i (69% yield). ¹H NMR (400 MHz, CD₃Cl₃) δ 7.78-7.68 (m, 2H), 7.45-7.22 (m, 8H), 7.22 (d, 1H), 6.94 (s, 1H), 4.73 (s, 1H), 4.05 (s, 2H), 3.52-3.20 (m, 2H), 3.29-2.62 (m, 7H), 2.48-2.31 (m, 2H). MS (ESI) m/z: Calculated: 423.5; Observed: 423.7 (M⁺+1).

Compound 57

3-(6-(5-(cyclopentylmethoxy)benzofuran-2-yl)-3,4-dihydroisoquinolin-2(1H)-yl)propanoic acid Tert-butyl 3-(6-(5-(cyclopentylmethoxy)benzofuran-2-yl)-3,4-dihydroisoquinolin-2(1H)-yl)propanoate (Step 3 in Scheme 8)

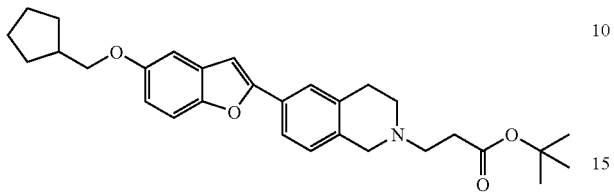

The title compound was prepared as Example Compound 37 (step 3 in Scheme 8) in the general method described above (73 mg, 40% yield): $^1$H NMR (400 MHz, CDCl$_3$) δ 7.57 (m, 2H), 7.36 (d, 1H), 7.06 (d, 1H), 7.01 (d, 1H), 6.85 (m, 2H), 3.85 (d, 2H), 3.69 (s, 2H), 2.96 (dd, 2H), 2.86 (dd, 2H), 2.79 (dd, 2H), 2.54 (dd, 2H), 2.38 (m, 1H), 1.66 (m, 2H), 1.59 (m, 4H), 1.45 (s, 9H), 1.39 (t, 2H). MS (ESI) m/z: Calculated: 475.27; Observed: 475.90 (M$^+$+1).

3-(6-(5-(cyclopentylmethoxy)benzofuran-2-yl)-3,4-dihydroisoquinolin-2(1H)-yl)propanoic acid (Step 4 in Scheme 8)

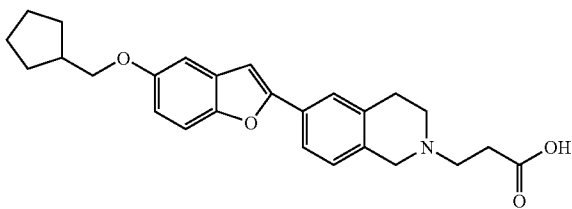

The title compound was prepared as Example Compound 37 (step 4 in Scheme 8) in the general method described above (19 mg, 72% yield): $^1$H NMR (400 MHz, CD$_3$OD) δ 7.78 (m, 2H), 7.38 (d, 1H), 7.30 (d, 1H), 7.17 (s, 1H), 7.09 (d, 1H), 6.88 (dd, 1H), 4.53 (s, 2H), 3.87 (d, 2H), 3.68 (m, 2H), 3.58 (dd, 2H), 3.27 (m, 1H), 2.93 (dd, 2H), 2.37 (m, 1H), 1.86 (m, 2H), 1.63 (m, 4H), 1.41 (m, 2H). MS (ESI) m/z: Calculated: 419.21; Observed: 420.2 (M$^+$+1).

Compound 58

3-(4-(5-cyclopentylbenzofuran-2-yl)-3-fluorobenzylamino)propanoic acid (Step 5 in Scheme 1)

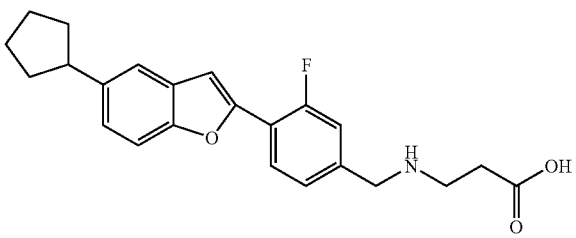

The title compound was prepared as Example Compound 1 (Step 5 in Scheme 1) in the general method described above (4.1 mg, 4.6% yield): $^1$H NMR (400 MHz, CD$_3$OD) δ 8.10 (dd, 1H), 7.50 (s, 1H), 7.42 (m, 3H), 7.25 (m, 2H), 4.30 (s, 2H), 3.25 (m, 2H), 3.10 (m, 1H), 2.25 (dd, 2H), 2.18 (m, 2H), 1.84 (m, 2H), 1.65 (m, 4H). MS (ESI) m/z: Calculated: 381.17; Observed: 381.80 (M$^+$+1).

Compound 59

3-(4-(5-benzylbenzofuran-2-yl)-3-fluorophenoxy)propane-1,2-diol 4-(5-benzylbenzofuran-2-yl)-3-fluorophenol (Step 4 in Scheme 1)

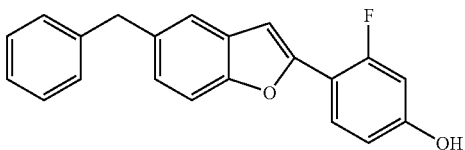

The title compound was prepared as the Example Compound 1 (step 4 in Scheme 1) in the general method described above except using 4-bromo-3-fluorophenol. The compound was used without further purification for the next step reaction.

3-(4-(5-benzylbenzofuran-2-yl)-3-fluorophenoxy)propane-1,2-diol (Step 2 in Scheme 9)

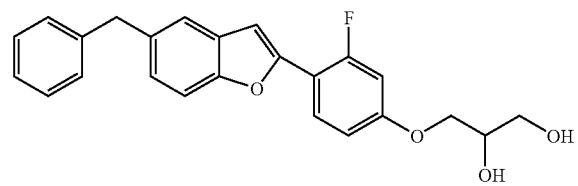

A mixture of 4-(5-benzylbenzofuran-2-yl)-3-fluorophenol (22 mg, 0.069 mmol), and 3-bromopropane-1,2-diol (48 mg, 0.31 mmol) and 2 N NaOH (200 µL) in i-PrOH (1 mL) was heated at 90° C. for overnight. After concentration of solvents under reduced pressure, the resulting residue was dissolved in DMSO and purified by reverse phase preparative HPLC (Phenomenex reverse phase Luna 5µ C18 (2) column, 60×21.2 mm ID, mobile phase: A=0.05% TFA in water; B=0.05% TFA in acetonitrile) to yield the desired final product (4.4 mg, 16% yield) as a white powder: $^1$H NMR (400 MHz, CD$_3$OD) δ 7.89 (m, 1H), 7.40 (m, 2H), 7.23 (m, 4H), 7.10 (m, 2H), 6.99 (m, 1H), 6.89 (m, 2H), 4.10 (m, 1H), 4.04 (s, 2H), 3.96 (m, 2H), 3.65 (m, 2H). MS (ESI) m/z: Calculated: 392.14; Observed: 393.20 (M$^+$+1).

Compound 60

1-((3-Fluoro-4-(5-(1-(methylsulfonyl)piperidine-4-yl)benzofuran-2-yl)phenyl)methyl)azetidine-3-carboxylic acid 4-(4-(2,2-Diethoxyethoxy)-1-(methylsulfonyl)piperidine

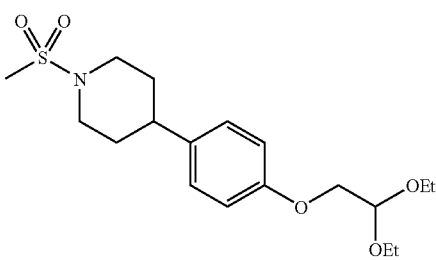

The title compound was prepared as Example Compound 1 (step 1 in Scheme 1) in the is general method described above (70% yield): $^1$H NMR (400 MHz, CDCl$_3$) δ 7.07 (d, 2H), 6.82 (d, 2H), 4.81 (t, 1H), 3.96 (d, 4H), 3.90 (t, 2H), 3.79-3.72 (m, 2H), 3.67-3.59 (m, 2H), 2.81 (s, 3H), 2.77 (t, 2H), 2.61 (m, 1H), 1.77-1.70 (m, 2H), 1.21 (t, 6H).

4-(Benzofuran-5-yl)-1-(methylsulfonyl)piperidine

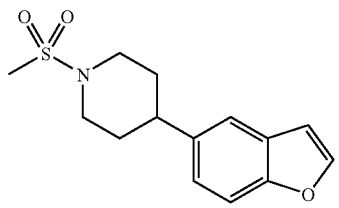

The title compound was prepared as Example Compound 1 (step 2 in Scheme 1) in the general method described above (20% yield): $^1$H NMR (400 MHz, CDCl$_3$) δ 7.45 (d, 1H), 7.42 (s, 1H), 7.13 (d, 1H), 6.62 (s, 1H), 4.03 (m, 4H), 2.83 (s, 3H), 2.78 (t, 1H), 1.82-1.75 (m, 4H).

5-(1-(Methylsulfonyl)piperidin-4-yl)benzofuran-2-yl-2-boronic acid

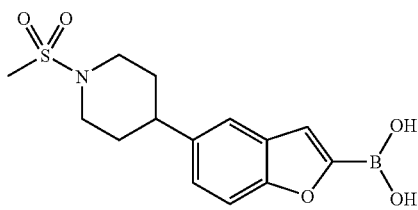

The title compound was prepared as Example Compound 1 (step 3 in Scheme 1) in the general method described above (84% yield): MS (ESI) m/z: Calculated: 323.1; Observed: 324.1 (M$^+$+1).

3-Fluoro-4-(5-(1-(methylsulfonyl)piperidin-4-yl)benzofuran-2-yl)benzaldehyde

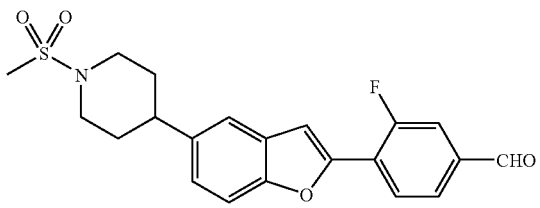

The title compound was prepared as Example Compound 1 (step 4 in Scheme 1) in the general method described above (62% yield): $^1$H NMR (400 MHz, CDCl$_3$) δ 10.03 (s, 1H), 8.21 (t, 1H), 7.79 (d, 1H), 7.72 (d, 1H), 7.51-7.21 (m, 4H), 3.98 (m, 4H), 2.84 (s, 3H), 2.76 (m, 1H), 2.05-1.81 (m, 4H).

1-((3-Fluoro-4-(5-(1-(methylsulfonyl)piperidine-4-yl)benzofuran-2-yl)phenyl)methyl) azetidine-3-carboxylic acid

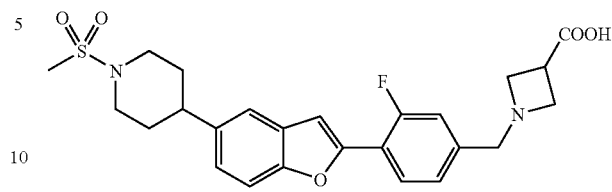

The title compound was prepared as Example Compound 1 (step 5 in Scheme 1) in the general method described above (70% yield): $^1$H NMR (400 MHz, DMSO-d$_6$) δ 8.21 (t, 1H), 7.84 (d, 1H), 7.77 (d, 1H), 7.51-7.21 (m, 4H), 4.85 (bs, 2H), 4.46 (s, 2H), 3.98 (m, 4H), 3.68 (m, 1H), 3.62 (m, 4H), 2.84 (s, 3H), 2.76 (m, 1H), 1.91-1.71 (m, 4H). MS (ESI) m/z: Calculated: 486.1; Observed: 486.9 (M$^+$+1).

Compound 61

1-(3-fluoro-4-(5-(tetrahydro-2H-pyran-4-yl)benzofuran-2-yl)phenyl)methyl)azetidine-3-carboxylic acid 4-(benzofuran-5-yl)-tetrahydro-2H-pyran-4-ol (Step 1 in Scheme 6)

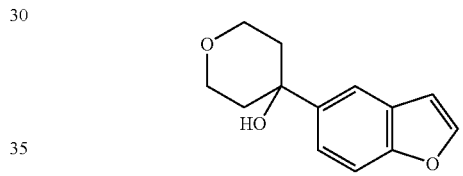

To a suspension of Mg (550 mg, 23.0 mmol) in dry THF (15mL), under nitrogen atmosphere was added 5-bromobenzofuran (3.9 g, 20.0 mmol) in one portion. A crystal of iodine was added and then the contents were refluxed for 3h. The reaction was then allowed to attain ambient temperature, and then cooled to −40° C. Pyran-4-one (3.0 g, 30.0 mmol) was added drop-wise and the resulting solution was allowed to reach room temperature. The reaction mixture was quenched by addition of 1N HCl (5 mL) and then was diluted with ether (30 mL). It was washed with water (2×15 mL) and the combined organic extract was washed with brine (15 mL), dried and concentrated under reduced pressure to give the crude carbinol as colorless oil. Purification by column chromatography using 5% EtOAc-hexanes afforded the desired product as white solid (41%). $^1$H NMR (400 MHz, CDCl$_3$) δ 7.74 (d, 1H), 7.64 (d, 1H), 7.51-7.44 (m, 2H), 6.78 (d, 1H), 4.00-3.88 (m, 4H), 2.25 (t, 2H), 1.78-1.74 (m, 2H).

5-(Tetrahydro-2H-pyran-4-yl)benzofuran (Step 2 in Scheme 6)

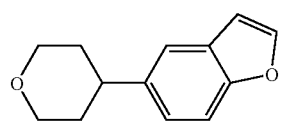

To a solution of 4-(benzofuran-5-yl)-tetrahydro-2H-pyran-4-ol (109 mg, 0.5 mmol) in DCM (5 mL) at 0° C. under nitrogen atmosphere was added triethylsilane (175 mg, 1.5 mmol) followed by TFA (570 mg, 5.0 mmol). After stirring for 15 min at the same temperature, the cooling bath was removed, and allowed the reaction mixture to reach room temperature. It was further stirred at room temperature for 6 h and then poured into crushed ice-water mixture (10 mL). It was extracted with DCM (3×10 mL), and the combined organic layer was washed with brine (10 mL), dried and evaporated. The crude compound was purified by column chromatography using 5% EtOAc-hexanes to afford the desired product (88%). $^1$H NMR (400 MHz, CDCl$_3$) δ 7.61 (d, 1H), 7.44 (d, 2H), 7.15 (d, 1H), 6.73 (d, 1H), 4.11 (dd, 2H), 3.56 (t, 2H), 2.89-2.81 (m, 1H), 1.93-1.79 (m, 4H).

5-(tetrahydro-2H-pyran-4-yl-benzofuran-2-yl-2-boronic acid (Step 3 in Scheme 1)

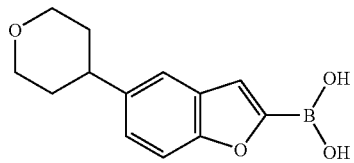

The title compound was prepared in the same manner as described in step 3 of Scheme 1(86%): $^1$H NMR (400 MHz, CDCl$_3$) δ 7.48-7.41 (m, 2H), 7.28 (d, 1H), 7.20 (d, 1H), 4.10 (t, 2H), 3.60 (t, 2H), 2.98-2.94 (m, 1H), 1.97-1.80 (m, 4H). MS (ESI) m/z: Calculated: 324.35; Observed: 325.1 (M$^+$+1).

3-Fluoro-4-(5-(tetrahydro-2H-pyran-4-yl-benzofuran-2-yl)benzaldehyde (Step 4 in Scheme 1)

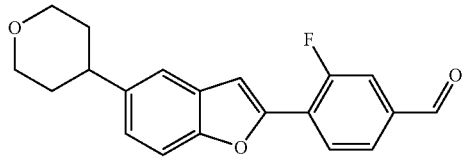

The title compound was prepared in the same manner as described in step 4 of Scheme 1 (68%): $^1$H NMR (400 MHz, CDCl$_3$) δ 10.01 (s, 1H), 8.04 (t, 1H), 7.80 (t, 1H), 7.74 (d, 1H), 7.52 (t, 2H), 7.40 (d, 1H), 7.22 (s, 1H), 4.10 (t, 2H), 3.60 (t, 2H), 2.98-2.94 (m, 1H), 1.97-1.80 (m, 4H). MS (ESI) m/z: Calculated: 324.35; Observed: 325.1 (M$^+$+1).

1-(3-fluoro-4-(5-(tetrahydro-2H-pyran-4-yl)benzofuran-2-yl)phenyl)methyl) azetidine-3-carboxylic acid (Step 5 in Scheme 1)

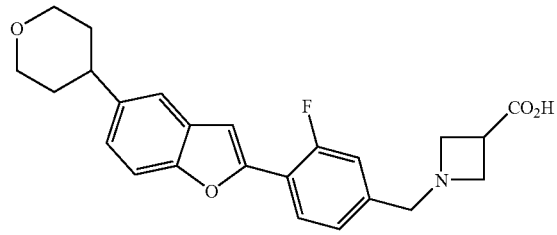

The title compound was prepared according the reductive amination procedure as described in step 5 of Scheme-1 (73% yield). $^1$H NMR (400 MHz, CD$_3$OD) δ 8.12 (t, 1H), 7.54 (s, 1H), 7.49 (d, 1H), 7.43 (s, 1H), 7.41 (d, 1H), 7.31-7.27 (m, 2H), 4.46 (s, 2H), 4.39-4.31 (m, 4H), 4.05 (d, 2H), 3.71-3.64 (m, 1H), 3.59 (t, 2H), 1.95-1.89 (m, 4H). MS (ESI) m/z: Calculated: 409.45; Observed: 410.0 (M$^+$+1).

Activity of Compounds of the Invention

The compounds of the invention made according to the synthesis noted above were assayed for their ability to modulate the S1P-1 receptor. Compounds were evaluated for the ability to induce S1P1-specific receptor internalization using standard in-vitro receptor internalization assays and their utility as immunoregulatory agents was demonstrated by their activity as agonists of the S1P1 receptor measured in the receptor internalization assay (>50% of S1P control at 10 nM or 300 nM). The compounds accordingly are expected to be useful as S1P-1 receptor modulators, e.g., in the treatment of a variety of S1P-1 receptor-mediated clinical conditions. Such conditions include transplant rejection (solid organ transplant and islet cells); transplant rejection (tissue); cancer; autoimmune/inflammatory diseases; rheumatoid arthritis; lupus; insulin dependent diabetes (Type I); non-insulin dependent diabetes (Type II); multiple sclerosis; psoriasis; ulcerative colitis; inflammatory bowel disease; Crohn's disease; acute and chronic lymphocytic leukemias and lymphomas.

To further demonstrate the suitability of compounds of the invention as S1P-1 receptor modulators for treating conditions such as transplant rejection; cancer; autoimmune/inflammatory diseases; rheumatoid arthritis; lupus; diabetes; multiple sclerosis; psoriasis; ulcerative colitis; inflammatory bowel disease; Crohn's disease; acute and chronic lymphocytic leukemias and lymphomas where immunosuppression is central (of which reduction of lymphopenia is therefore a well-established indicator), compounds of the invention were evaluated in laboratory animals as described below.

Protocol

Mice

C57BL/6J mice (B6, Jackson Laboratories, Bar Harbor, Me.) were maintained in a specific pathogen-free environment under a microisolator containment system. Both adult male and female age-matched mice were used for all experiments, which were reviewed and approved by the Animal Care and Use Committee at the University of Virginia. Whenever the protocol stated Mice were anesthetized via intraperitoneal injections of ketamine hydrochloride (125 mg/kg; Sanofi Winthrop Pharmaceuticals, New York, N.Y.), xylazine (12.5 mg/kg Tranqui Ved; Phoenix Scientific, St. Joseph, Mo.), and atropine sulfate (0.025 mg/kg; Fujisawa USA, Deerfield, Ill.).

Flow Cytometry Preparation and Analysis

Blood was harvested from at least six mice for each time point of 0, 4, 8, 24, 48, 72 hours following one day, 3 days or 7 days daily dosing with the test compound. Following terminal bleeds brain and certain other tissues were harvested from all animals undergoing treatment. Cell counts were determined from whole blood, yielding cell counts in thousands of cells per microliter (K/IL).

To identify and quantify lymphocyte subsets, cell suspensions were analyzed by flow cytometry. Following red blood cell lysis, cells were stained with anti-mouse monoclonal antibodies against CD3, CD4, CD8, CD19, and NK1.1 (BD Biosciences, San Jose, Calif.). Cells were analyzed via four-color flow cytometry on a FACSCalibur (BD Biosciences) in the University of Virginia Cancer Center Core Facility. Lymphocyte subsets, including B cells, total T cells, CD4 T cells, CD8 T cells, double-positive thymocytes, double-negative thymocytes, NK cells, and NK/T cells, were analyzed. The size of each cell population was calculated as the product of the total lymphocyte count recorded by the Hemavet or hemocytometer and the percentage of positive lymphocytes recorded by the flow cytometer. All data were analyzed with BD Biosciences Cell Quest analysis software.
Statistical Analysis
Statistical significance was determined using Student's t-test to compare all time points to -24 hour group.
The compounds tested:
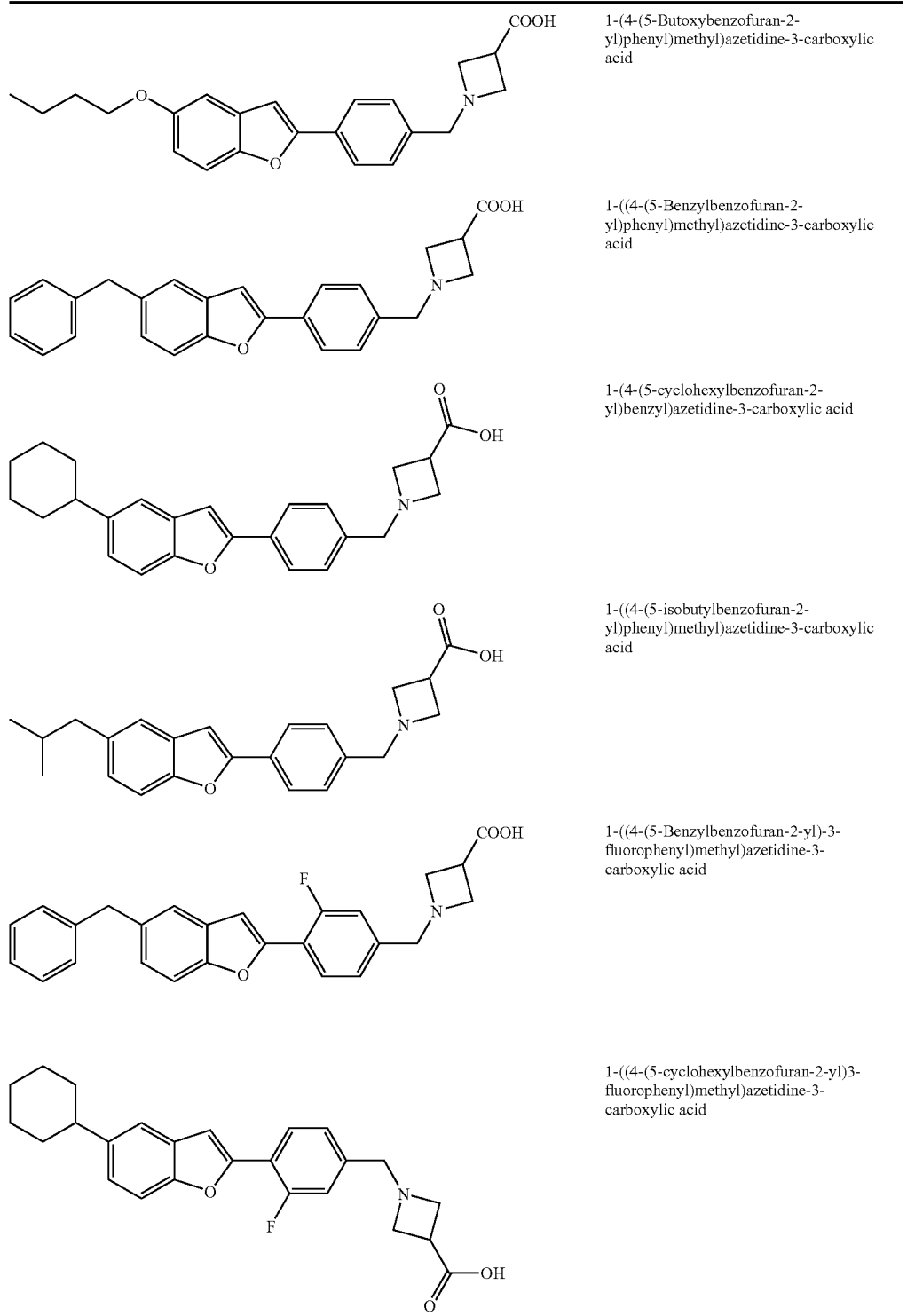

-continued

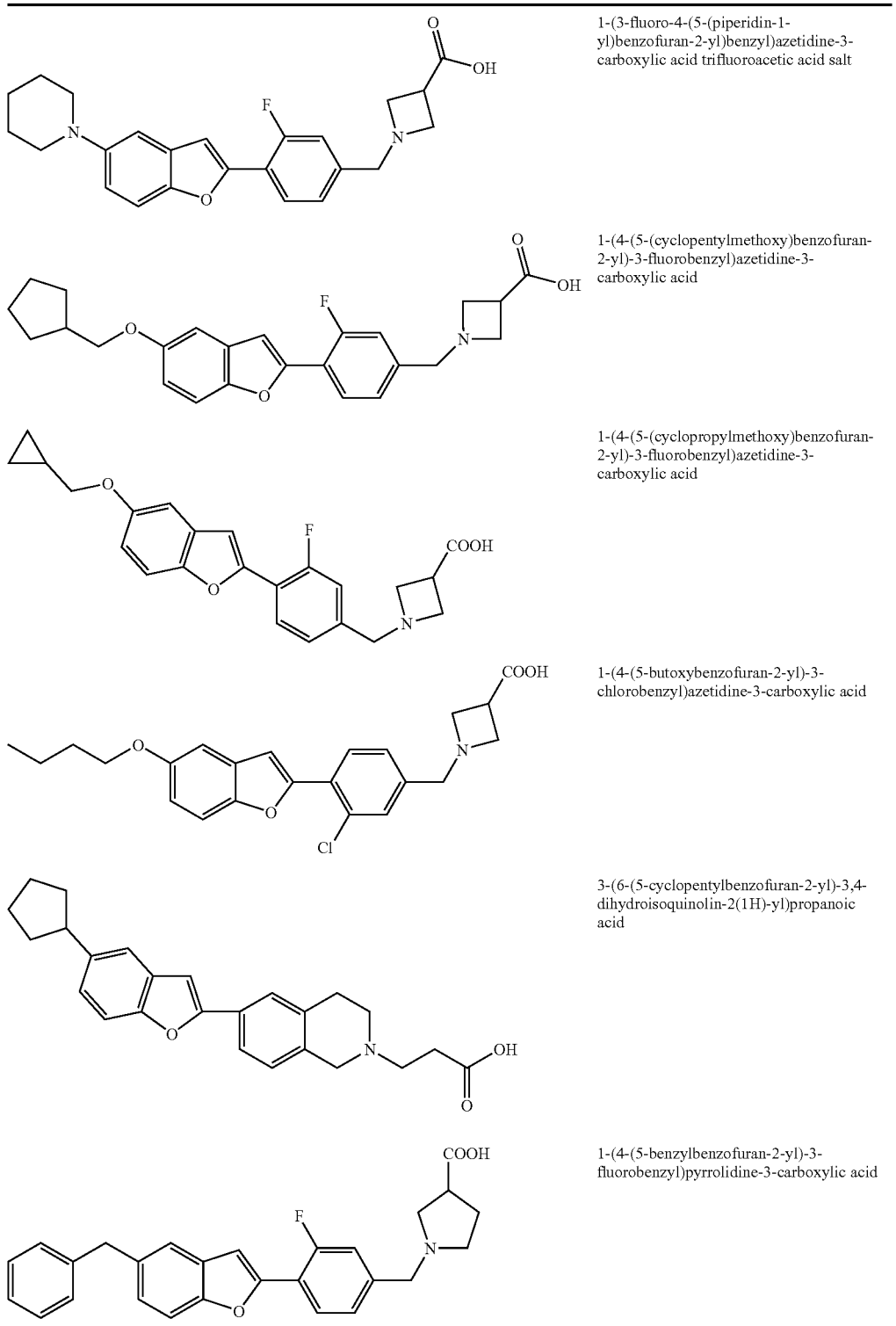

showed a reduction in lymphopenia ranging from 35% to 90% compared to baseline at dosages of 0.3 to 10 mg/kg. The final two compounds in the above table did not show lymphopenia reduction under the conditions tested. As such, the compounds of the invention are expected to be useful drugs for treating conditions such as transplant rejection; cancer; autoimmune/inflammatory diseases; rheumatoid arthritis; lupus; diabetes; multiple sclerosis; psoriasis; ulcerative colitis; inflammatory bowel disease; Crohn's disease; acute and chronic lymphocytic leukemias and lymphomas where immunosuppression is central.

Equivalents

Those skilled in the art will recognize, or be able to ascertain using no more than routine experimentation, numerous equivalents to the specific procedures described herein. Such equivalents are considered to be within the scope of the invention. Various substitutions, alterations, and modifications may be made to the invention without departing from the spirit and scope of the invention. Other aspects, advantages, and modifications are within the scope of the invention. The contents of all references, issued patents, and published patent applications cited throughout this application are hereby incorporated by reference. The appropriate components, processes, and methods of those patents, applications and other documents may be selected for the invention and embodiments thereof.

What is claimed is:

1. A compound having the formula

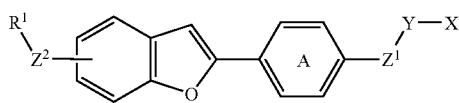

and pharmaceutically acceptable salts thereof, wherein pheny ring A is optionally substituted with one, two or three substituents selected from the group consisting of halogen, hydroxyl, $SR^2$, $S(O)_2R^2$, $S(O)_2NR^2$, $NHS(O)_2R^2$, $COR^2$, $CO_2R^2$, cyano, amino, $C_{1-5}$ alkylamino, arylamino, heteroarylamino, $C_{1-6}$ alkyl, $C_{1-5}$ alkylthio, $C_{1-5}$ alkoxy, halogen-substituted $C_{1-6}$ alkyl, and halogen-substituted $C_{1-5}$ alkoxy;

$R^2$ is selected from the group consisting of hydrogen, hydroxyl, amino, $C_{1-5}$ alkylamino, arylamino, $C_{1-6}$ alkyl, $C_{1-5}$ alkoxy, $C_{1-5}$ alkylthio, halogen-substituted $C_{1-6}$ alkyl, halogen-substituted $C_{1-5}$ alkoxy, aryl, and heteroaryl;

the benzofuran ring is optionally substituted with 1 to 5 substituents selected from the group consisting of $C_{1-6}$ alkyl, $C_{1-5}$ alkylthio, $C_{1-5}$ alkoxy, halogen, hydroxyl, cyano, halogen-substituted $C_{1-6}$ alkyl and halogen-substituted $C_{1-5}$ alkoxy;

X is selected from the group consisting of $WC(O)OR^{6a}$, $WP(O)R^{6b}R^{6c}$, $WS(O)_2OH$, $WCONHSO_3H$ and 1H-tetrazol-5-yl;

W is a direct bond, oxygen or $C_{1-4}$ alkyl having one or more substituents independently selected from the group consisting of halogen, hydroxyl, cyano, amino, alkylamino, arylamino, heteroarylamino groups, $C_{1-4}$ alkoxy and $CO_2H$;

$R^{6a}$ is hydrogen or $C_{1-4}$ alkyl;

$R^{6b}$ and $R^{6c}$ are independently hydrogen, hydroxyl, $C_{1-4}$ alkyl or halogen substituted $C_{1-4}$ alkyl;

Y is formula (a) where the left and right asterisks indicate the point of attachment

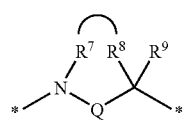

(a)

wherein

Q is selected from the group consisting of a direct bond, $C=O$, $C=S$, $SO_2$, and $(CR^{10}R^{11})_m$;

m is 0, 1, 2 or 3;

$R^7$ and $R^8$ are joined together with the atoms to which they are attached to form a 4 to 7-membered ring, optionally having a heteroatom;

$R^9$ is selected from the group consisting of hydrogen, halogen, hydroxyl, cyano, $C_{1-6}$ alkyl, $C_{1-5}$ alkylthio, $C_{1-5}$ alkoxy, halogen-substituted $C_{1-6}$ alkyl and halogen-substituted $C_{1-5}$ alkoxy;

$R^{10}$ and $R^{11}$ are independently selected from the group consisting of hydrogen, halogen, hydroxyl, cyano, $C_{1-6}$ alkyl, $C_{1-5}$ alkoxy, $C_{1-5}$ alkylthio, halogen-substituted $C_{1-6}$ alkyl and halogen-substituted $C_{1-5}$ alkoxy;

$Z^1$ and $Z^2$ are independently selected from the group consisting of O, $NR^3$, S, S(O), $S(O)_2NR^3$, $(CR^4R^5)_n$, $C=O$, $C=S$, $C=N-R^3$, and a direct bond, where $R^3$ is selected from the group consisting of hydrogen, hydroxyl, $C_{1-6}$ alkyl, $C_{1-5}$ alkoxy, $C_{1-5}$ alkylthio, halogen-substituted $C_{1-6}$ alkyl and halogen-substituted $C_{1-5}$ alkoxy, aryl, and heteroaryl, or when $Z^2$ is a direct bond, $R^3$ is a $C_3$-$C_6$ ring optionally containing a heteroatom;

$R^4$ and $R^5$ are independently selected from the group consisting of hydrogen, halogen, hydroxyl, cyano, $C_{1-6}$ alkyl, $C_{1-5}$ alkoxy, $C_{1-5}$ alkylthio, halogen-substituted $C_{1-6}$ alkyl and halogen-substituted $C_{1-5}$ alkoxy, aryl, and heteroaryl or together with the carbon atom to which they are attached form $C=O$;

n is 0, 1, 2 or 3; and $R^1$ is selected from the group consisting of $C_{1-6}$ alkyl, $C_{2-6}$ alkenyl, $C_{2-6}$ alkynyl, $C_{3-6}$ cycloalkyl, $C_{1-5}$ alkoxy, $C_{1-5}$ alkylamino, aryl, and heteroaryl wherein the $C_{1-6}$ alkyl, $C_{2-6}$ alkenyl, $C_{2-6}$ alkynyl, $C_{3-6}$ cycloalkyl, $C_{1-5}$ alkoxy, $C_{1-5}$ alkylamino, aryl, and heteroaryl groups are optionally substituted with a substituent selected from the group consisting of hydroxyl, halogen, cyano, amino, alkylamino, aryl amino, and heteroarylamino and wherein the aryl and heteroaryl groups are optionally substituted with 1 to 5 substituents selected from the group consisting of hydroxyl, halogen, cyano, $C_{1-6}$ alkyl, $C_{1-5}$ alkylthio, $C_{1-5}$ alkoxy, and $C_{3-6}$ cycloalkyl.

2. The compound of claim 1, wherein $Z^1$ and $Z^2$ are independently selected from the group consisting of O, $(CR^4R^5)_n$, and a direct bond.

3. The compound of claim 2, wherein $R^4$ and $R^5$ are hydrogen.

4. The compound of claim 1, wherein $R^1$ is selected from the group consisting of $C_{1-6}$ alkyl, $C_{3-6}$ cycloalkyl, $C_{1-5}$ alkoxy, aryl and heteroaryl.

5. The compound of claim 1, wherein the pharmaceutically acceptable salt is selected from the group consisting of hydrochloride, maleate, citrate, fumarate, succinate, tartarate, mesylate, sodium, potassium, magnesium, and calcium salts.

6. A compound having the formula

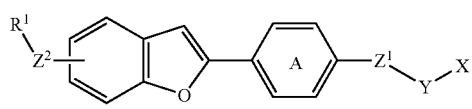

wherein
the benzofuran ring is optionally substituted with 1 to 5 substituents selected from the group consisting of $C_{1-6}$ alkyl, $C_{1-5}$ alkylthio, $C_{1-5}$ alkoxy, halogen, hydroxyl, cyano, halogen-substituted $C_{1-6}$ alkyl and halogen-substituted $C_{1-5}$ alkoxy;
pheny ring A is optionally substituted with one, two or three substituents selected from the group consisting of halogen, hydroxyl, $SR^2$, $S(O)_2R^2$, $S(O)_2NR^2$, $NHS(O)_2R^2$, $COR^2$, $CO_2R^2$, cyano, amino, $C_{1-5}$ alkylamino, arylamino, heteroarylamino, $C_{1-6}$ alkyl, $C_{1-5}$ alkylthio, $C_{1-5}$ alkoxy, halogen-substituted $C_{1-6}$ alkyl, and halogen-substituted $C_{1-5}$ alkoxy;
$R^2$ is selected from the group consisting of hydrogen, hydroxyl, amino, $C_{1-5}$ alkylamino, arylamino, $C_{1-6}$ alkyl, $C_{1-5}$ alkoxy, $C_{1-5}$ alkylthio, halogen-substituted $C_{1-6}$ alkyl, halogen-substituted $C_{1-5}$ alkoxy, aryl and heteroaryl;
X is $-C(O)OR^{6a}$, where $R^{6a}$ is hydrogen or $C_{1-4}$ alkyl;
Y is formula (a)

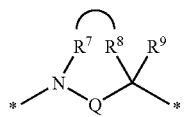

(a)

wherein
Q is $(CR^{10}R^{11})_m$;
m is 0, 1, 2, 3 or 4;
$R^7$ and $R^8$ taken with the atoms to which they are attached, form a 4 to 7-membered ring, optionally having a heteroatom;
$R^9$ is selected from the group consisting of hydrogen, halogen, hydroxyl, and cyano;
$Z^1$ and $Z^2$ are independently O or $(CR^4R^5)_n$, where $R^4$ and $R^5$ are independently hydrogen, halogen, hydroxyl, cyano, $C_{1-6}$ alkyl, or $C_{1-5}$ alkoxy;
n is 0, 1, 2 or 3; and
$R^1$ is selected from the group consisting of $C_{1-6}$ alkyl, $C_{2-6}$ alkenyl, $C_{2-6}$ alkynyl, $C_{3-6}$ cycloalkyl, $C_{1-5}$ alkoxy, $C_{1-5}$ alkylamino, aryl, and heteroaryl wherein the $C_{1-6}$ alkyl, $C_{2-6}$ alkenyl, $C_{2-6}$ alkynyl, $C_{3-6}$ cycloalkyl, $C_{1-5}$ alkoxy, and $C_{1-5}$ alkylamino groups are optionally substituted with a substituent selected from the group consisting of hydroxyl, halogen, cyano, amino, alkylamino, arylamino, and heteroarylamino and wherein the aryl and heteroaryl groups are optionally substituted with one to five substituents selected from the group consisting of hydroxyl, halogen, cyano, $C_{1-6}$ alkyl, $C_{1-5}$ alkylthio, $C_{1-5}$ alkoxy, and $C_{3-6}$ cycloalkyl or a pharmaceutically acceptable salt thereof.

7. The compound of claim 6, wherein $R^1$ is selected from the group consisting of $C_{1-6}$ alkyl, $C_{3-6}$ cycloalkyl, $C_{1-5}$ alkoxy, aryl, and heteroaryl.

8. The compound of claim 6, wherein the pharmaceutically acceptable salt is selected from the group consisting of hydrochloride, maleate, citrate, fumarate, succinate, tartarate, mesylate, sodium, potassium, magnesium, and calcium salts.

9. A pharmaceutical composition comprising the compound of claim 1 in a therapeutically effective amount.

10. A compound selected from the group consisting of
1-(4-(5-Phenylbenzofuran-2-yl)benzyl)azetidine-3-carboxylic acid;
1-((4-(5-Butylbenzofuran-2-yl)phenyl)methyl)azetidine-3-carboxylic acid;
1-(4-(5-Butoxybenzofuran-2-yl)phenyl)methyl)azetidine-3-carboxylic acid;
1-((4-(5-Benzylbenzofuran-2-yl)phenyl)methyl)azetidine-3-carboxylic acid;
1-((4-(7-Benzylbenzofuran-2-yl)phenyl)methyl)azetidine-3-carboxylic acid;
1-(4-(5-cyclohexylbenzofuran-2-yl)benzyl)azetidine-3-carboxylic acid;
1-(4-(5-cyclohexylbenzofuran-2-yl)benzyl)piperidine-4-carboxylic acid;
1-((4-(5-Butylbenzofuran-2-yl)phenyl)methyl)piperidine-4-carboxylic acid;
1-((4-(5-Benzylbenzofuran-2-yl)phenyl)methyl)piperidine-4-carboxylic acid;
1-((4-(5-isobutylbenzofuran-2-yl)phenyl)methyl)azetidine-3-carboxylic acid;
1-((4-(5-phenethylbenzofuran-2-yl)phenyl)methyl)azetidine-3-carboxylic acid;
1-(4-(5-(pyridin-3-yl)benzofuran-2-yl)benzyl)azetidine-3-carboxylic acid;
1-(4-(5-isobutylbenzofuran-2-yl)benzyl)piperidine-4-carboxylic acid;
1-((4-(5-Benzylbenzofuran-2-yl)2-fluorophenyl)methyl)azetidine-3-carboxylic acid;
1-((4-(5-Benzylbenzofuran-2-yl)-3-fluorophenyl)methyl)azetidine-3-carboxylic acid;
1-(4-(5-Butoxybenzofuran-2-yl)phenyl)methyl)piperidine-4-carboxylic acid;
1-(4-(5-(6-methylpyridin-2-yl)benzofuran-2-yl)benzyl)azetidine-3-carboxylic acid;
1-(4-(5-phenoxybenzofuran-2-yl)benzyl)azetidine-3-carboxylic acid;
1-((4-(5-Isopentylbenzofuran-2-yl)phenyl)methyl)azetidine-3-carboxylic acid;
1-((4-(6-Butoxybenzofuran-2-yl)phenyl)methyl)azetidine-3-carboxylic acid;
1-((4-(5-Butoxybenzofuran-2-yl)3-fluorophenyl)methyl)azetidine-3-carboxylic acid;
1-((4-(5-Butoxybenzofuran-2-yl)-3-methoxyphenyl)methyl)azetidine-3-carboxylic acid;
1-((4-(5-cyclohexylbenzofuran-2-yl)3-fluorophenyl)methy)azetidine-3-carboxylic acid;
1-((4-(5-(thiophen-2-yl)benzofuran-2-yl)phenyl)methyl)azetidine-3-carboxylic acid;
1-(4-(5-cyclopentylbenzofuran-2-yl)benzyl)azetidine-3-carboxylic acid;
1-(3-fluoro-4-(5-(piperidin-1-yl)benzofuran-2-yl)benzyl)azetidine-3-carboxylic acid trifluoroacetic acid salt;
1-((4-(5-benzylbenzofuran-2-yl)-3-methoxyphenyl)methyl)azetidine-3-carboxylic acid;
1-(4-(5-benzylbenzofuran-2-yl)-3-chlorobenzyl)azetidine-3-carboxylic acid;
1-(4-(5-(cyclopentylmethoxy)benzofuran-2-yl)-3-fluorobenzyl)azetidine-3- carboxylic acid;
1-(4-(5-(cyclopentylmethoxy)benzofuran-2-yl)benzyl)azetidine-3-carboxylic acid;
1-(4-(5-benzylbenzofuran-2-yl)-3-cyanobenzyl)azetidine-3-carboxylic acid;
1-(4-(5-benzylbenzofuran-2-yl)-3-fluorobenzyl)pyrrolidine-3-carboxylic acid;
1-(4-(5-cyclopentylbenzofuran-2-yl)-3-fluorobenzyl)azetidine-3-carboxylic acid;
1-(4-(5-benzylbenzofuran-2-yl)-3-methylbenzyl)azetidine-3-carboxylic acid;

1-(4-(5-cyclopentylbenzofuran-2-yl)-3-methoxybenzyl) azetidine-3-carboxylic acid;

1-(4-(5-benzylbenzofuran-2-yl)-3,5-difluorobenzyl)azetidine-3-carboxylic acid;

1-(4-(5-(cyclopropylmethoxy)benzofuran-2-yl)-3-fluorobenzyl)azetidine-3-carboxylic acid;

1-(4-(5-butoxybenzofuran-2-yl)-3-chlorobenzyl)azetidine-3-carboxylic acid;

1-(3-chloro-4-(5-cyclopentylbenzofuran-2-yl)benzyl)azetidine-3-carboxylic acid;

4-(4-(5-benzylbenzofuran-2-yl)-3-fluorobenzyl)morpholine-2-carboxylic acid;

4-(4-(5-(cyclopentylmethoxy)benzofuran-2-yl)-3-fluorobenzyl)morpholine-2-carboxylic acid; and 1-(3-fluoro-4-(5-(1-(methylsulfonyl)piperidin-4-yl)benzofuran-2-yl)benzyl)azetidine-3-carboxylic acid;

or pharmaceutically acceptable salts thereof.

11. The compound of claim 1 wherein $R^1$ is selected from the group consisting of $C_{1-6}$ alkyl, $C_{3-6}$ cycloalkyl, aryl and heteroaryl wherein the aryl is phenyl, wherein the heteroaryl is pyridinyl, methylpyridinyl, or thiophenyl;

$Z^1$ and $Z^2$ are independently selected from the group consisting of a direct bond, O, and $(CR^4R^5)_n$;

$R^4$ and $R^5$ are hydrogen;

n is 1 or 2;

phenyl ring A is optionally substituted with 1 or 2 substituents selected from the group consisting of $C_{1-5}$ alkoxy, $C_{1-6}$ alkyl, cyano, and halogen;

Q is $(CR^{10}R^{11})_m$;

m is 1;

$R^7$ and $R^8$ taken with the atoms to which they are attached form a ring; wherein the ring is selected from the group consisting of azetidine, piperidine, pyrrolidine, and morpholine;

$R^9$ is hydrogen;

$R^{10}$ and $R^{11}$ are independently selected from the group consisting of hydrogen and $C_{1-6}$ alkyl.

* * * * *